(12) United States Patent
Weingarten et al.

(10) Patent No.: US 7,687,659 B2
(45) Date of Patent: Mar. 30, 2010

(54) PROCESS FOR THE SEPARATION OF PROBUCOL DERIVATIVES

(75) Inventors: M. David Weingarten, Cumming, GA (US); Christopher M. Chappelow, Midland, MI (US)

(73) Assignee: Salutria Pharmaceuticals LLC, Alpharetta, GA (US)

( * ) Notice: Subject to any disclaimer, the term of this patent is extended or adjusted under 35 U.S.C. 154(b) by 829 days.

(21) Appl. No.: 11/409,539

(22) Filed: Apr. 21, 2006

(65) Prior Publication Data

US 2006/0258883 A1  Nov. 16, 2006

Related U.S. Application Data

(60) Provisional application No. 60/674,001, filed on Dec. 27, 2005, provisional application No. 60/705,837, filed on Aug. 5, 2005.

(51) Int. Cl.
*C07C 69/00* (2006.01)
(52) U.S. Cl. ...................................... 560/138
(58) Field of Classification Search .................. None
See application file for complete search history.

(56) References Cited

U.S. PATENT DOCUMENTS

| 5,262,439 | A | 11/1993 | Parthasarathy et al. |
| 6,121,319 | A | 9/2000 | Somers |
| 6,147,250 | A | 11/2000 | Somers |
| 6,323,359 | B1 | 11/2001 | Jass |
| 6,548,699 | B1 | 4/2003 | Somers |
| 6,602,914 | B2 | 8/2003 | Meng |
| 6,617,352 | B2 | 9/2003 | Somers |
| 6,828,447 | B2 | 12/2004 | Meng |
| 6,852,878 | B2 | 2/2005 | Meng et al. |
| 6,881,860 | B2 | 4/2005 | Luchoomun et al. |
| 6,960,683 | B2 | 11/2005 | Meng |
| 7,087,645 | B2 | 8/2006 | Glass et al. |
| 7,273,948 | B2 | 9/2007 | Weingarten et al. |
| 7,294,737 | B2 | 11/2007 | Weingarten |
| 2002/0193446 | A1 | 12/2002 | Meng |
| 2004/0204485 | A1 | 10/2004 | Sikorski et al. |
| 2004/0266879 | A1 | 12/2004 | Sikorski et al. |
| 2005/0090487 | A1 | 4/2005 | Somers |
| 2005/0171028 | A1 | 8/2005 | Meng et al. |
| 2005/0228192 | A1* | 10/2005 | Jass et al. ................... 560/135 |
| 2005/0267187 | A1 | 12/2005 | Weingarten |
| 2006/0025481 | A1 | 2/2006 | Strange |
| 2006/0079713 | A1 | 4/2006 | Meng |

FOREIGN PATENT DOCUMENTS

| FR | 2130975 | | 10/1972 |
| FR | 2133024 | | 10/1972 |
| FR | 2130975 | A5 | 11/1972 |
| FR | 2133024 | A5 | 11/1972 |
| FR | 2134810 | | 11/1972 |
| FR | 2134810 | A5 | 12/1972 |
| FR | 2140769 | | 12/1972 |
| FR | 2140771 | | 12/1972 |
| FR | 2140769 | A5 | 1/1973 |
| FR | 2140771 | A5 | 1/1973 |
| FR | 2168137 | A1 | 8/1973 |

* cited by examiner

*Primary Examiner*—Paul A Zucker
(74) *Attorney, Agent, or Firm*—King & Spalding

(57) ABSTRACT

Provided are methods for the separation of mono-substituted probucol derivatives from a mixture of both mono- and di-substituted probucol derivatives. In particular, methods are provided for the separation of mono-carboxy substituted probucol derivatives from a mixture of mono- and di-carboxy substituted probucol derivatives.

78 Claims, 7 Drawing Sheets

PROCESS FOR THE SEPARATION OF PROBUCOL DERIVATIVES

CROSS REFERENCE TO RELATED APPLICATIONS

This application claims the benefit of priority to U.S. Provisional Application No. 60/674,001, filed Dec. 27, 2005, and U.S. Provisional Application No. 60/705,837, filed Aug. 5, 2005, the disclosures of which are incorporated herein by reference.

FIELD OF THE INVENTION

Methods are provided for the separation of mono-carboxy substituted probucol derivatives from di-carboxy substituted probucol derivatives.

BACKGROUND

Derivatives of probucol have been developed as therapeutics, for example, for the treatment of cardiovascular disease and as anti-inflammatory agents. Probucol contains two hydroxyl groups and can be modified to form mono-substituted or di-substituted derivatives. In particular, mono-substituted derivatives, for example, mono-ethers and mono-esters of probucol have been found to have useful therapeutic properties. Mono-esters and ethers of probucol have been reported to be useful in the treatment of inflammatory diseases such as rheumatoid arthritis, osteoarthritis, asthma, and dermatitis. See, for example, U.S. Pat. No. 6,147,250. Methods for treating transplant rejection using mono-substituted derivatives of probucol also have been reported. See U.S. Patent Publication No. 2004/138147. Of particular interest are monoester derivatives of probucol that include a carboxyl group, such as the following compound, which has been shown, when dosed orally, to block VCAM-1 expression, reduce atherosclerosis and have potent anti-oxidant activity:

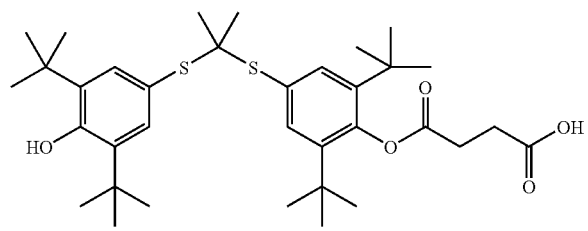

U.S. Pat. No. 5,262,439 discloses that carboxylic acid derivatives of probucol compounds can be prepared by treating probucol compounds with an excess of dicarboxylic acid anhydride and catalytic amounts of 4-dimethylamino pyridine at a temperature sufficient to ensure that the dicarboxylic acid anhydride is liquid.

U.S. Pat. No. 6,147,250 discloses that monoesters of probucol can be prepared by treating probucol in tetrahydrofuran with sodium hydride and an acid chloride or acid anhydride. In one example using this process, a monoester of probucol is prepared in approximately 14% yield following purification by chromatographic methods.

U.S. Pat. No. 6,323,359 discloses methods of manufacturing probucol derivatives. The '359 patent discloses the use of alkali metal hydroxide, alkali metal alkoxide, alkali ammonium alkoxide, and alkyl ammonium hydroxide to form salts of the probucol derivative compounds and then reacting the salts with a dicarboxylic acid anhydride.

U.S. Patent Publication No. 2004/0204485 discloses processes for the preparation of esters and ethers of probucol by reacting probucol or a free hydroxyl-containing probucol derivative with a Grignard reagent or a lithium reagent to form a magnesium or lithium salt, followed by a reaction with an ester-forming or ether-forming compound. The method described for separating the mono-esters from the di-esters is similar to the '359 patent.

U.S. Patent Publication No. 2005/0267187 discloses additional processes for the preparation of esters and ethers of probucol and also uses a method described for separating the mono-esters from the di-esters similar to the '359 patent.

A series of French patents have disclosed that certain probucol derivatives are hypocholesterolemic and hypolipemic agents: Fr 2.168.137 (bis-4-hydroxyphenylthioalkane esters); Fr 2140771 (tetralinyl phenoxy alkanoic esters of probucol); Fr 2.140.769 (benzofuryloxyalkanoic acid derivatives of probucol); Fr 2.134.810 (bis-(3-alkyl-5-alkyl-4-thiazole-5-carboxy)phenylthio)alkanes); Fr 2.133.024 (bis-(4-nicotinoyloxyphenylthio)-propanes); and Fr 2.130.975 ((bis-(4-phenoxyalkanoyloxy)-phenylthio)alkanes). French Patent Publication No. 2,168,137 describes the production of diesters of probucol by reacting probucol with a halide or anhydride of an organic acid in an inert solvent with heat and in the presence of a base such as an alkaline hydroxide or carbonate, or a tertiary amine (for example, triethylamine). The O-metal salt derivative of probucol is also suggested to be useful as the reaction intermediate.

A number of methods for the synthesis and isolation of mono-substituted probucol derivatives have been described in the art. In general, the synthesis of the mono-substituted derivative also produces the di-substituted derivative. Of particular challenge is the separation of the mono-substituted derivative from the di-substituted derivative from the mixture resulting from the synthesis steps.

It is an object of the invention to provide efficient methods of separating mono-carboxy substituted probucol derivatives from di-carboxy substituted probucol derivatives.

SUMMARY OF THE INVENTION

It has been discovered that a 4-(carboxylic acid bearing) probucol derivative can be separated from a mixture comprising the 4-(carboxylic acid bearing) probucol derivative and 4,4'-di(carboxylic acid bearing) probucol derivative which optionally includes probucol, by extraction with at least one organic solvent from an aqueous solution in which the mixture is partially acidified or partially basified (i.e., partially neutralized). The 4-(carboxylic acid bearing) probucol derivative is preferentially extracted into the organic layer. If the 4-(carboxylic acid bearing) probucol derivative is provided in the form of a salt, an amount of acid is added to partially convert the salt to the free carboxylic acid form. If the 4-(carboxylic acid bearing) probucol derivative is provided as the free carboxylic acid, then, generally, a small amount of base is used to form the partial salt form.

DETAILED DESCRIPTION OF THE INVENTION

Figure 1:
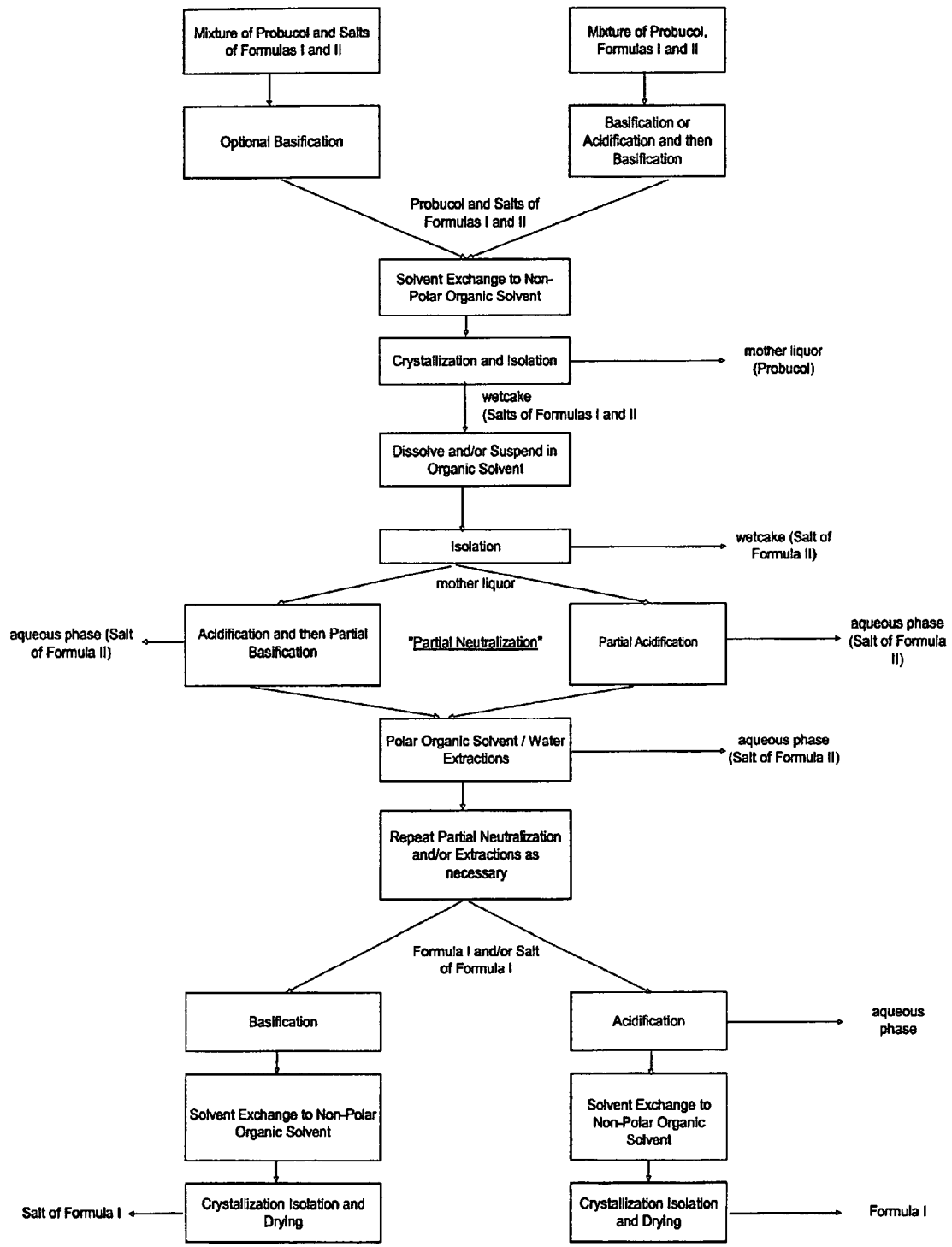
FIGS. 1, 2, 3, 4, 5, and 6 schematically show particular, non-limiting embodiments of the invention.
Figure 2:
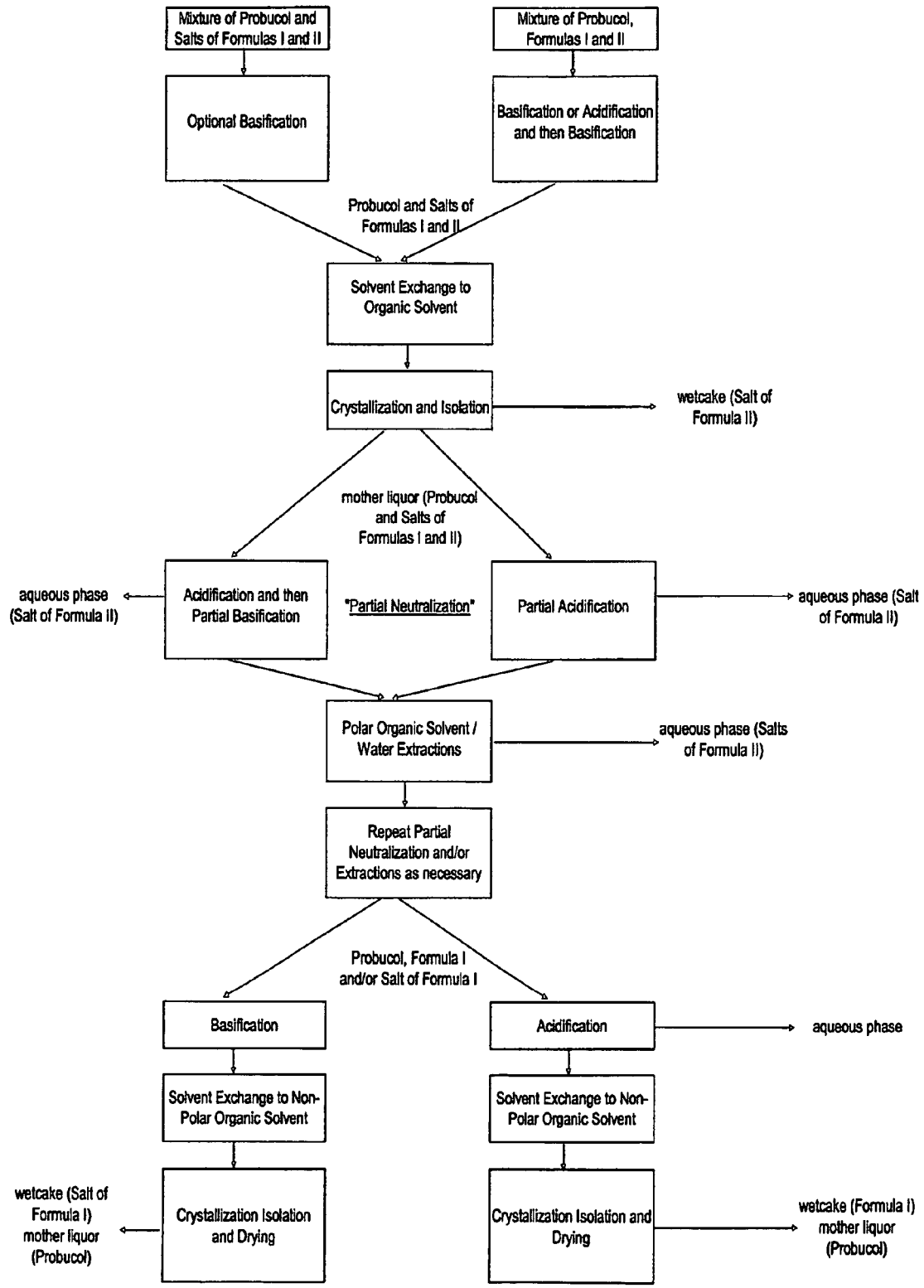
Figure 3:
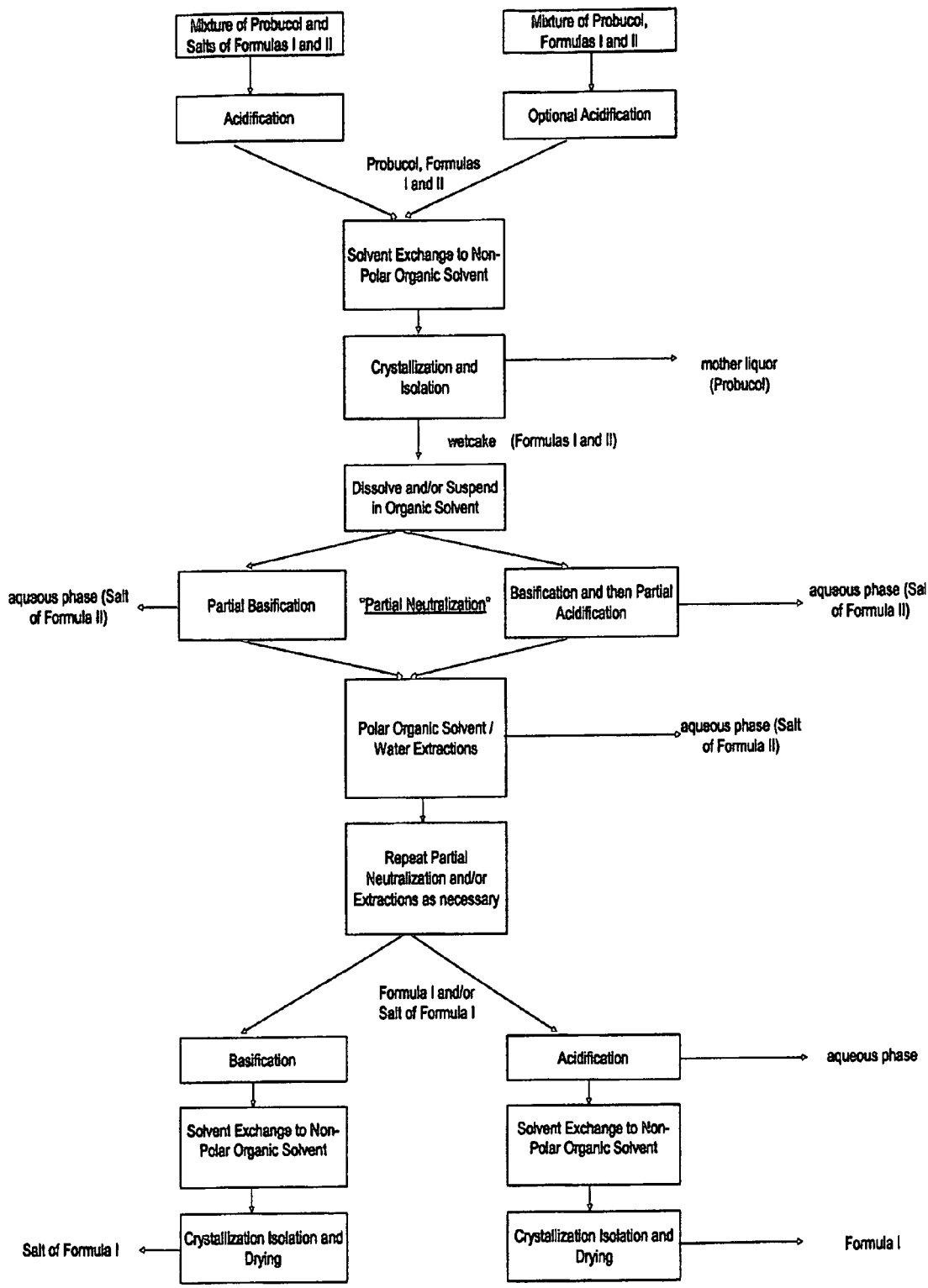
Figure 4:
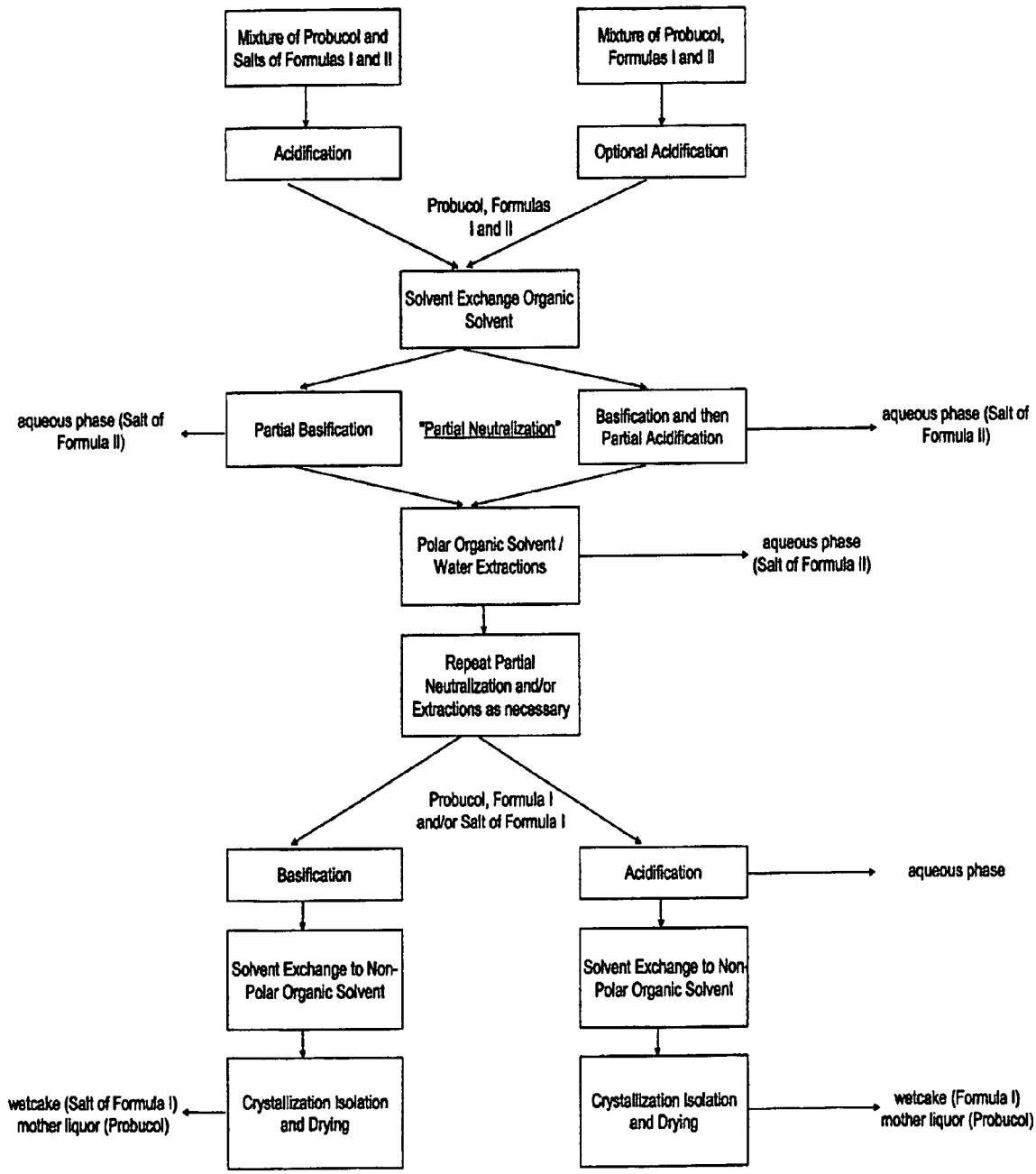
Figure 5:
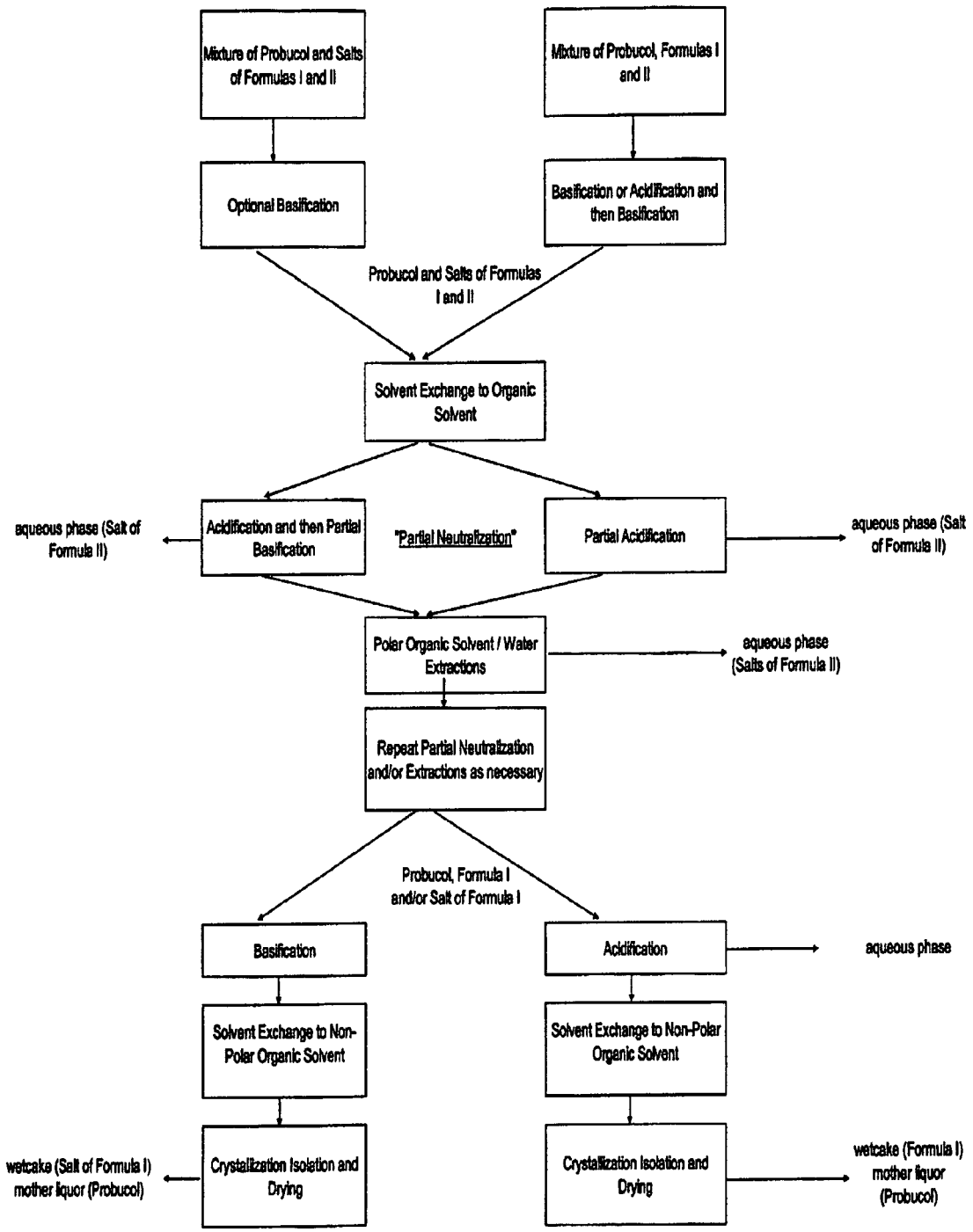
Figure 6:
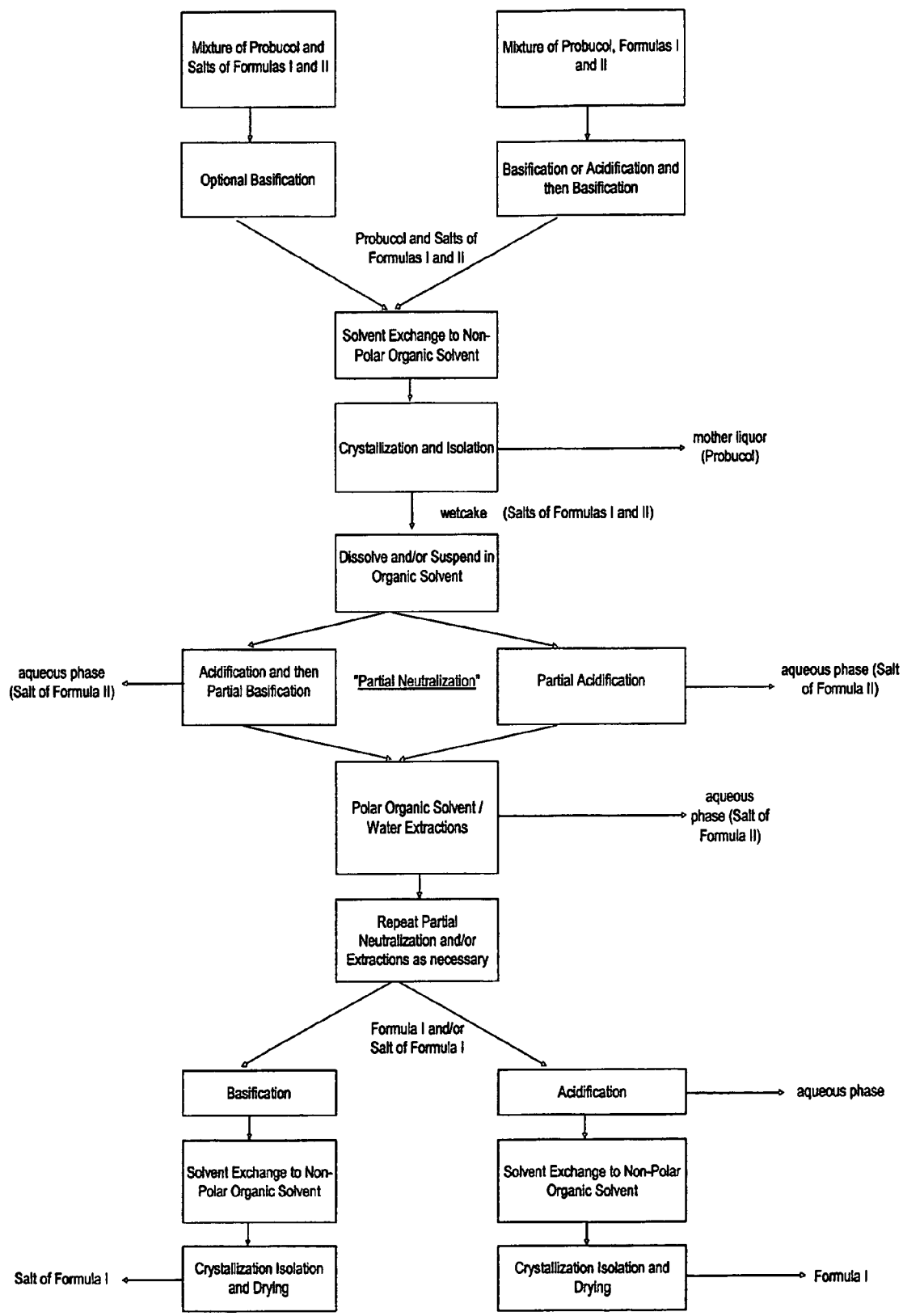

This invention addresses the need for an improved and more efficient process for separating a mono-carboxy substituted probucol derivative from a di-carboxy-substituted probucol derivative, in particular from mixtures resulting from manufacturing processes of mono-carboxy substituted probucol derivatives.

It has been discovered that a 4-(carboxylic acid bearing) probucol derivative can be separated in high purity from a mixture comprising the 4-(carboxylic acid bearing) probucol derivative and 4,4'-di(carboxylic acid bearing) probucol derivative which optionally includes probucol, by extraction with at least one organic solvent from an aqueous solution in which the mixture is partially acidified or partially basified (i.e., partially neutralized). The 4-(carboxylic acid bearing) probucol derivative is preferentially extracted into the organic layer. If the 4-(carboxylic acid bearing) probucol derivative is provided in the form of a salt, an amount of acid is added to partially convert the salt to the free carboxylic acid form. If the 4-(carboxylic acid bearing) probucol derivative is provided as the free carboxylic acid, then a small amount of base is used to form the partial salt form. The process of adding a small amount of acid or base as needed to produce the 4-(carboxylic acid bearing) probucol derivative partially in the form of the free carboxylic acid, and partially in the salt form is referred to herein as "partial neutralization".

The methods disclosed herein can be used after manufacturing processes known in the art for making mono-carboxy substituted probucol derivatives. One example includes the method of manufacturing described in U.S. Pat. No. 6,147,250, wherein monoesters of probucol are synthesized by treating probucol in tetrahydrofuran with sodium hydride and an acid chloride or acid anhydride. Another example is disclosed in U.S. Pat. No. 6,323,359, wherein the use of alkali metal hydroxide, alkali metal alkoxide, alkali ammonium alkoxide, and alkyl ammonium hydroxide to form alkali metal salts of the probucol derivative compounds and then reacting the salts with a dicarboxylic acid anhydride. In another example, U.S. Patent Publication No. 2004/0204485 describes methods of preparing compounds by reacting probucol or probucol derivatives with a Grignard reagent or a lithium reagent to produce a magnesium salt or lithium salt of probucol or the probucol derivative, respectively, followed by the addition of an ester or ether forming reagent.

U.S. Patent Publication No. 2005/0267187 discloses additional processes for the preparation of esters and ethers of probucol and also uses a method described for separating the mono-esters from the di-esters similar to the '359 patent.

In one embodiment, a process for separating a compound of Formula I and/or a salt of a compound of Formula I,

I

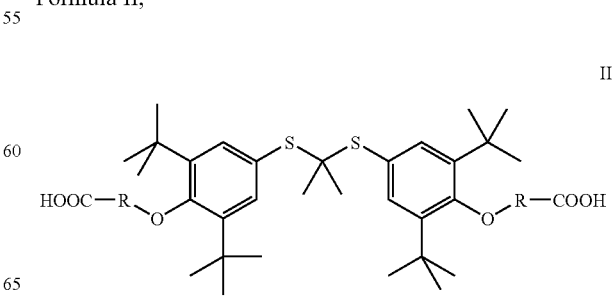

wherein R is a linker or is selected from the group consisting of —C(O)(CH$_2$)$_2$—, —CH$_2$—, —(CH$_2$)$_2$— and —(CH$_2$)$_3$—, from a mixture is provided, said mixture comprising:
said compound of Formula I;
said salt of a compound of Formula I;
a compound of Formula II and/or a salt of a compound of Formula II,

II

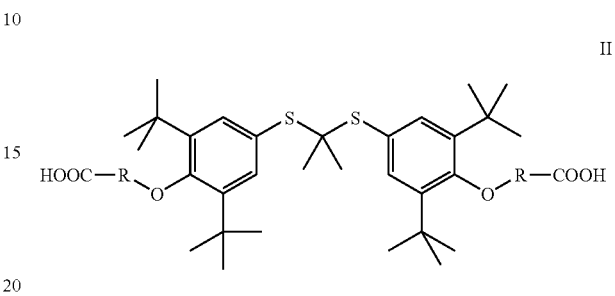

wherein R is a linker or is selected from the group consisting of —C(O)(CH$_2$)$_2$—, —CH$_2$—, —(CH$_2$)$_2$— and —(CH$_2$)$_3$—;
an organic phase;
an aqueous phase; and
optionally probucol; the process comprising:
isolating said organic phase comprising said compound of Formula I and/or said salt of a compound of Formula I.

In another embodiment, a process for separating a compound of Formula I and/or a salt of a compound of Formula I,

I

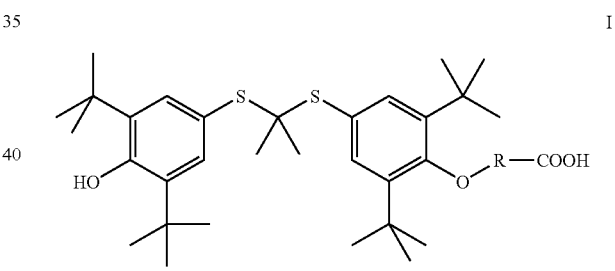

wherein R is a linker or is selected from the group consisting of —C(O)(CH$_2$)$_2$—, —CH$_2$—, —(CH$_2$)$_2$— and —(CH$_2$)$_3$—, from a mixture is provided, said mixture comprising:
said compound of Formula I;
said salt of a compound of Formula I;
a compound of Formula II and/or a salt of a compound of Formula II,

II wherein R is a linker or is selected from the group consisting of —C(O)(CH$_2$)$_2$—, —CH$_2$—, —(CH$_2$)$_2$— and —(CH$_2$)$_3$—;
an organic phase;
an aqueous phase; and
optionally probucol; the process comprising:

isolating said organic phase comprising:
at least a first organic solvent and a second organic solvent; and
said compound of Formula I and/or said salt of a compound of Formula I.

The first organic solvent may be a straight chain, branched or cyclic hydrocarbon that is saturated, unsaturated or partially unsaturated, for example, benzene, toluene, xylene, mesitylene, naphthalene, pentane, hexane, heptane, octane, nonane, decane, undecane, dodecane, tridecane, tetradecane, pentadecane, hexadecane, heptadecane, eicosane, cyclohexane, or petroleum ether, and mixtures thereof. The second organic solvent may be an ether, an ester, an alcohol, an amide, a nitrile, or a ketone, for example, tetrahydrofuran, ethyl acetate, isopropyl acetate, methyl alcohol, ethyl alcohol, isopropyl alcohol, acetonitrile, dimethylformamide, acetone, 2-butanone, and mixtures thereof.

The mixture of a compound of Formula I and a salt of a compound of Formula I can be obtained by partial neutralization, for example, by partial basification of the free acid form of said compound of Formula I or, for example, by partial acidification of said salt of a compound of Formula I.

In another embodiment, a process of separating a compound of Formula I and/or a salt of a compound of Formula I,

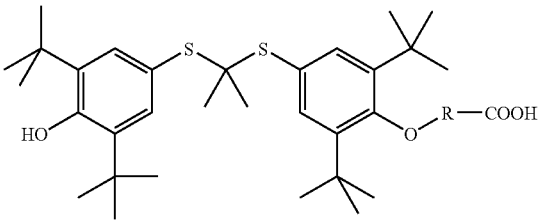

I wherein R is a linker or is selected from the group consisting of —C(O)(CH$_2$)$_2$—, —CH$_2$—, —(CH$_2$)$_2$— and —(CH$_2$)$_3$—, from a mixture is provided, said mixture comprising:
said compound of Formula I;
a compound of Formula II,

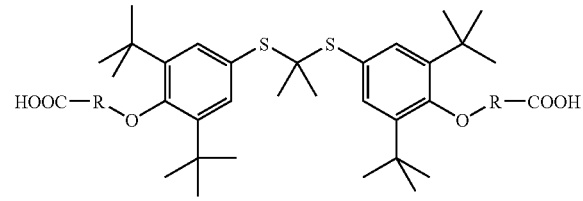

II wherein R is a linker or is selected from the group consisting of —C(O)(CH$_2$)$_2$—, —CH$_2$—, —(CH$_2$)$_2$— and —(CH$_2$)$_3$—; and
an organic phase; said process comprising:

partially basifying said mixture (for example, addition of an effective amount of base to afford both said compound of Formula I and salt of a compound of Formula I);
isolating said organic phase comprising said compound of Formula I and/or said salt of a compound of Formula I.

In another embodiment, a process of separating a compound of Formula I and/or a salt of a compound of Formula I,

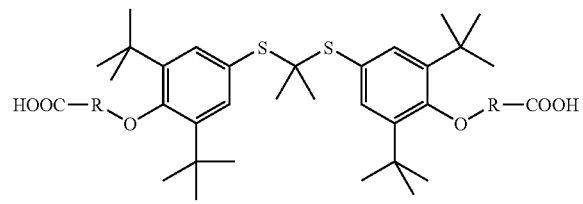

I wherein R is a linker or is selected from the group consisting of —C(O)(CH$_2$)$_2$—, —CH$_2$—, —(CH$_2$)$_2$— and —(CH$_2$)$_3$—, from a mixture is provided, said mixture comprising:
said salt of a compound of Formula I;
a salt of a compound of Formula II,

II wherein R is a linker or is selected from the group consisting of —C(O)(CH$_2$)$_2$—, —CH$_2$—, —(CH$_2$)$_2$— and —(CH$_2$)$_3$—; and
an organic phase; said process comprising:

partially acidifying said mixture (for example, addition of an effective amount of acid to afford both the compound of Formula I and said salt of said compound of Formula I); and
isolating said organic phase comprising said compound of Formula I and/or said salt of the compound of Formula I.

Adding an effective amount of an acid or base to afford both the compound of Formula I and a salt of a compound of Formula I (respectively, partially acidifying or partially basifying) is herein referred to as "partially neutralizing" affording a mixture that is "partially neutralized".

Moles of base added to a mixture comprising a compound of Formula I to afford partial neutralization may be accomplished, for example, by adding less than one molar equivalent of base per molar equivalent of total free acid groups in the mixture. In one embodiment, the moles of base added is, for example, about 0.1-5%, 0.1-10%, 10-20%, 10-30%, 10-90%, 20-70%, or 70-90% or about 1%, 5%, 10%, 20%, 30%, 40%, 50%, 60%, 70%, 80% or 90% of the total moles of free acid groups.

Moles of acid added to a mixture comprising a salt of a compound of Formula I to afford partial neutralization may be accomplished, for example, by adding less than one molar equivalent of acid per molar equivalent of total free acid salt groups in the mixture. In one embodiment, the moles of acid added is, for example, about 99.9-95%, 99.9-90%, 90-80%, 90-70%, 90-10%, 80-30%, or 30-10% or about 99%, 95%, 90%, 80%, 70%, 60%, 50%, 40%, 30%, 20% or 10% of the total moles of free acid salt groups.

The extent of partial neutralization needed (the amount of acid or base added) to achieve the desired separation can be adjusted based on factors such as choice of solvent(s), temperature, acid(s) and/or base(s) used, purity of starting mixture, and presence or absence of salt (for example, NaCl). When a first solvent is a straight chain, branched or cyclic hydrocarbon that is saturated, unsaturated or partially unsaturated (for example, heptanes, toluene), the isolation/separation of the 4-(carboxylic acid bearing) probucol derivative compound of Formula I and/or its salts from the 4,4'-(carboxylic acid bearing) probucol derivative can be improved by the use of a second solvent (for example, acetone, 2-butanone) that is both miscible in water and miscible in the first solvent.

In another embodiment, a process for separating a compound of Formula I and/or a salt of a compound of Formula I,

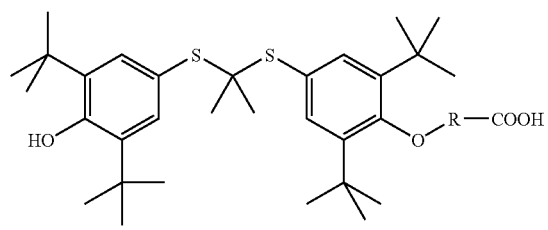

I wherein R is a linker or is selected from the group consisting of —C(O)(CH$_2$)$_2$—, —CH$_2$—, —(CH$_2$)$_2$— and —(CH$_2$)$_3$—, from a mixture is provided, said mixture comprising:
said compound of Formula I;
said salt of a compound of Formula I;
a compound of Formula II and/or a salt of a compound of Formula II

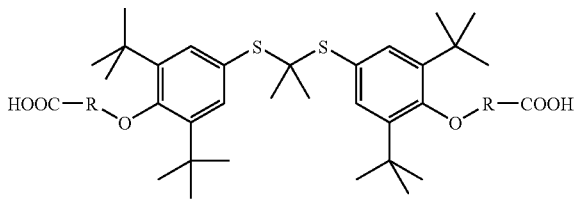

II wherein R is a linker or is selected from the group consisting of —C(O)(CH$_2$)$_2$—, —CH$_2$—, —(CH$_2$)$_2$— and —(CH$_2$)$_3$—;
an organic phase; and
an aqueous phase;

the process comprising:
removing from said mixture, said aqueous phase comprising:
said compound of Formula II and/or said salt of a compound of Formula II, thus leaving the organic phase comprising:
said compound of Formula I and/or said salt of a compound of Formula I; isolating said compound of Formula I and/or said salt of a compound of Formula I from said organic phase.

In another embodiment, a process for separating a compound of Formula I and/or a salt of a compound of Formula I,

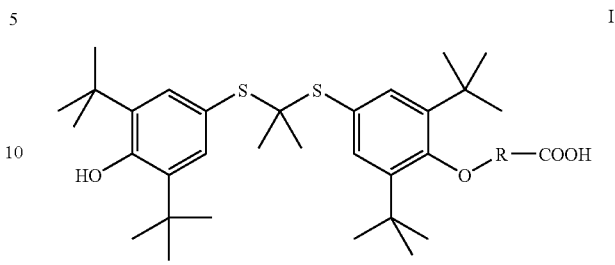

I wherein R is a linker or is selected from the group consisting of —C(O)(CH$_2$)$_2$—, —CH$_2$—, —(CH$_2$)$_2$— and —(CH$_2$)$_3$—, from a first mixture is provided, said first mixture comprising:
said compound of Formula I;
a compound of Formula II,

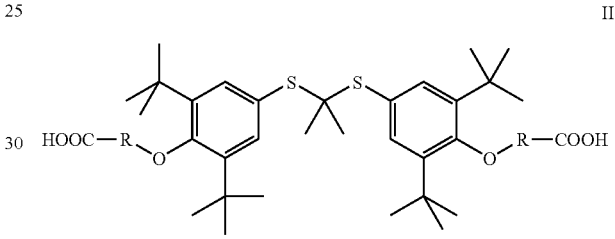

II wherein R is a linker or is selected from the group consisting of —C(O)(CH$_2$)$_2$—, —CH$_2$—, —(CH$_2$)$_2$— and —(CH$_2$)$_3$—; and
probucol; said process comprising:

removing said probucol from said first mixture to afford a second mixture, said second mixture comprising:
said compound of Formula I; and
said compound of Formula II;

partially neutralizing said second mixture, optionally adding at least one aqueous solvent, and optionally adding at least one organic solvent, thus affording a partially neutralized third mixture, said partially neutralized third mixture comprising:
an aqueous phase;
an organic phase;
said compound of Formula I;
said salt of a compound of Formula I; and
said compound of Formula II and/or a salt of a compound of Formula II;

removing from said partially neutralized third mixture, said aqueous phase comprising:
said compound of Formula II and/or said salt of a compound of Formula II, thus leaving the organic phase comprising:
said compound of Formula I and/or said salt of a compound of Formula I; isolating said compound of Formula I and/or said salt of a compound of Formula I from said organic phase.

In another embodiment, a process for separating a compound of Formula I and/or a salt of a compound of Formula I,

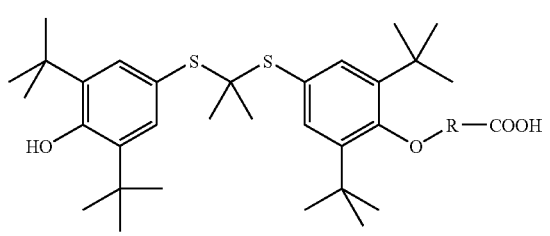

wherein R is a linker or is selected from the group consisting of —C(O)(CH$_2$)$_2$—, —CH$_2$—, —(CH$_2$)$_2$— and —(CH$_2$)$_3$—, from a first mixture, said first mixture comprising:

said salt of a compound of Formula I;
a salt of a compound of Formula II,

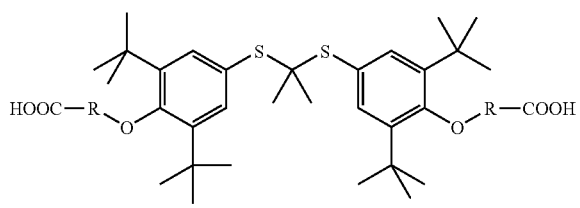

wherein R is a linker or is selected from the group consisting of —C(O)(CH$_2$)$_2$—, —CH$_2$—, —(CH$_2$)$_2$— and —(CH$_2$)$_3$—; and
probucol; said process comprising:

removing said probucol from said first mixture to afford a second mixture, said second mixture comprising:
said salt of a compound of Formula I; and
said salt of a compound of Formula II;

partially neutralizing said second mixture, optionally adding at least one aqueous solvent, and optionally adding at least one organic solvent, thus affording a partially neutralized third mixture, said partially neutralized third mixture comprising:
an aqueous phase;
an organic phase;
a compound of Formula I;
said salt of a compound of Formula I; and
a compound of Formula II and/or said salt of a compound of Formula II;

removing from said partially neutralized third mixture, said aqueous phase comprising:
said compound of Formula II and/or said salt of a compound of Formula II, thus leaving the organic phase comprising:
said compound of Formula I and/or said salt of a compound of Formula I; isolating said compound of Formula I and/or said salt of a compound of Formula I from said organic phase.

In another embodiment, a process for separating a compound of Formula I and/or a salt of a compound of Formula I,

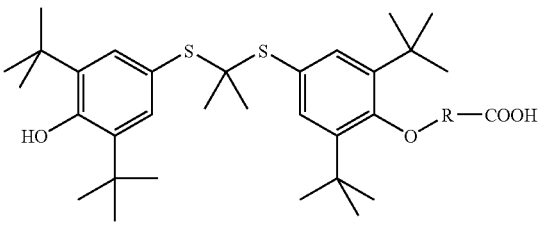

wherein R is a linker or is selected from the group consisting of —C(O)(CH$_2$)$_2$—, —CH$_2$—, —(CH$_2$)$_2$— and —(CH$_2$)$_3$—, from a first mixture, said first mixture comprising:

said compound of Formula I;
a compound of Formula II,

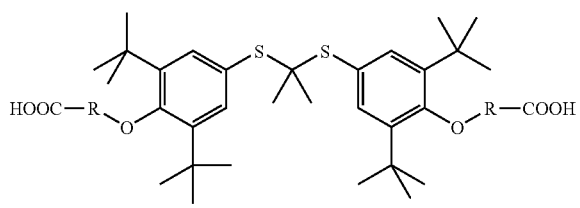

wherein R is a linker or is selected from the group consisting of —C(O)(CH$_2$)$_2$—, —CH$_2$—, —(CH$_2$)$_2$— and —(CH$_2$)$_3$—; and
probucol; said process comprising:

partially neutralizing said first mixture, optionally adding at least one aqueous solvent, and optionally adding at least one organic solvent, thus affording a partially neutralized second mixture, said partially neutralized second mixture comprising:
an aqueous phase;
an organic phase;
said compound of Formula I;
said salt of a compound of Formula I;
said compound of Formula II and/or a salt of a compound of Formula II; and
probucol;

removing from said partially neutralized second mixture the aqueous phase comprising:
said compound of Formula II and/or said salt of a compound of Formula II, thus leaving the organic phase comprising:
said compound of Formula I and/or said salt of a compound of Formula I; and
probucol;

isolating said compound of Formula I and/or said salt of a compound of Formula I.

In another embodiment, a process for separating a compound of Formula I and/or a salt of a compound of Formula I,

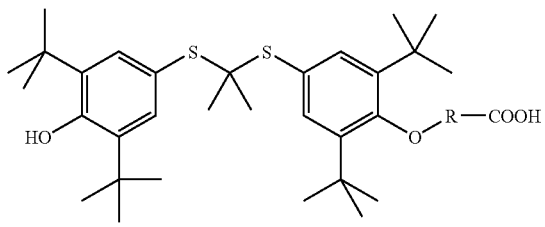

I wherein R is a linker or is selected from the group consisting of —C(O)(CH$_2$)$_2$—, —CH$_2$—, —(CH$_2$)$_2$— and —(CH$_2$)$_3$—, from a first mixture, said first mixture comprising:
said salt of compound of Formula I;
a salt of compound of Formula II,

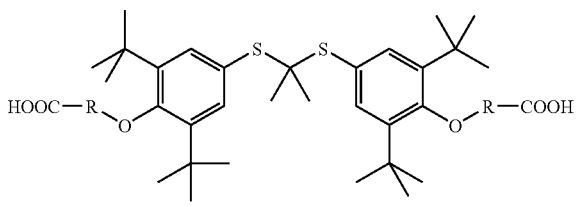

II wherein R is a linker or is selected from the group consisting of —C(O)(CH$_2$)$_2$—, —CH$_2$—, —(CH$_2$)$_2$— and —(CH$_2$)$_3$—; and
probucol; said process comprising:

partially neutralizing said first mixture, optionally adding at least one aqueous solvent, and optionally adding at least one organic solvent, thus affording a partially neutralized second mixture, said partially neutralized second mixture comprising:
an aqueous phase;
an organic phase;
said compound of Formula I;
said salt of a compound of Formula I;
a compound of Formula II and/or said salt of a compound of Formula II; and probucol;

removing from said partially neutralized second mixture the aqueous phase comprising:
said compound of Formula II and/or said salt of a compound of Formula II, thus leaving the organic phase comprising:
said compound of Formula I and/or said salt of a compound of Formula I; and probucol;

isolating said compound of Formula I and/or said salt of a compound of Formula I.

In all circumstances that the invention is used to isolate Formula I and/or its salts from Formula II and/or its salts, the same method can be used to isolate Formula III and/or its salts from Formula IV and/or its salts.

Formula III is described as

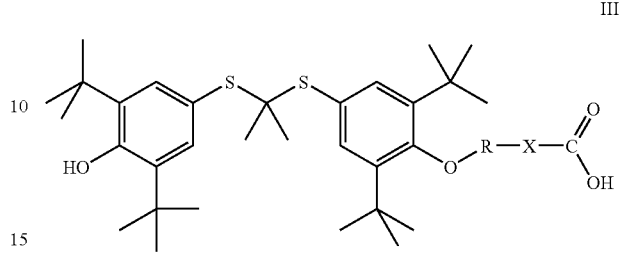

III wherein R is a bond or —C(O)—, and X is selected from the group consisting of a straight chain, branched or cyclic hydrocarbon that can be saturated, unsaturated or partially unsaturated and having 1, 2, 3, 4, 5, 6, 7, 8, 9 or 10 carbon atoms; aryl; heteroaryl; heterocycle; alkaryl; arylalkyl; or alkarylkyl; all of which can be optionally substituted.

Formula IV is described as:

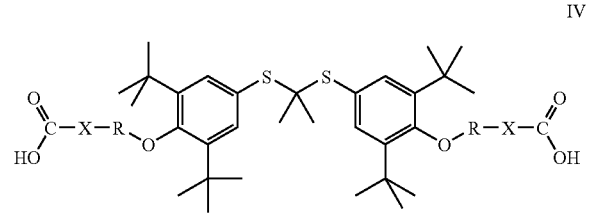

IV wherein R is a bond or —C(O)—, and X is selected from the group consisting of a straight chain, branched or cyclic hydrocarbon that can be saturated, unsaturated or partially unsaturated having 1, 2, 3, 4, 5, 6, 7, 8, 9 or 10 carbon atoms; aryl; heteroaryl; heterocycle; alkaryl; arylalkyl; or alkarylkyl; all of which can be optionally substituted.

In all circumstances that the invention is used to isolate Formula I and/or its salts from Formula II and/or its salts, the same method can be used to isolate probucol monosuccinate and/or its salts from probucol disuccinate and/or its salts.

probucol monosuccinate (also referred herein as "MSP"):

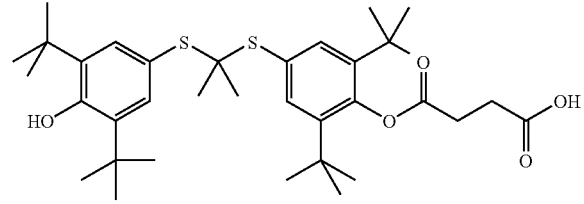

probucol disuccinate (also referred to herein as "DSP"):

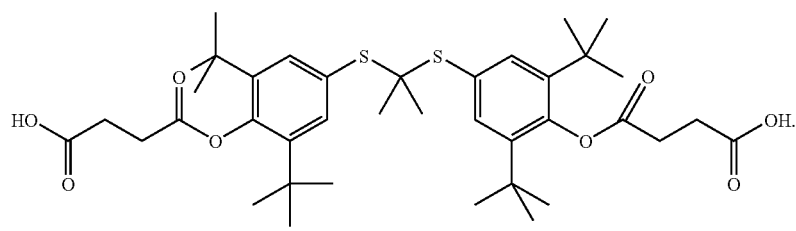

Figure 7:
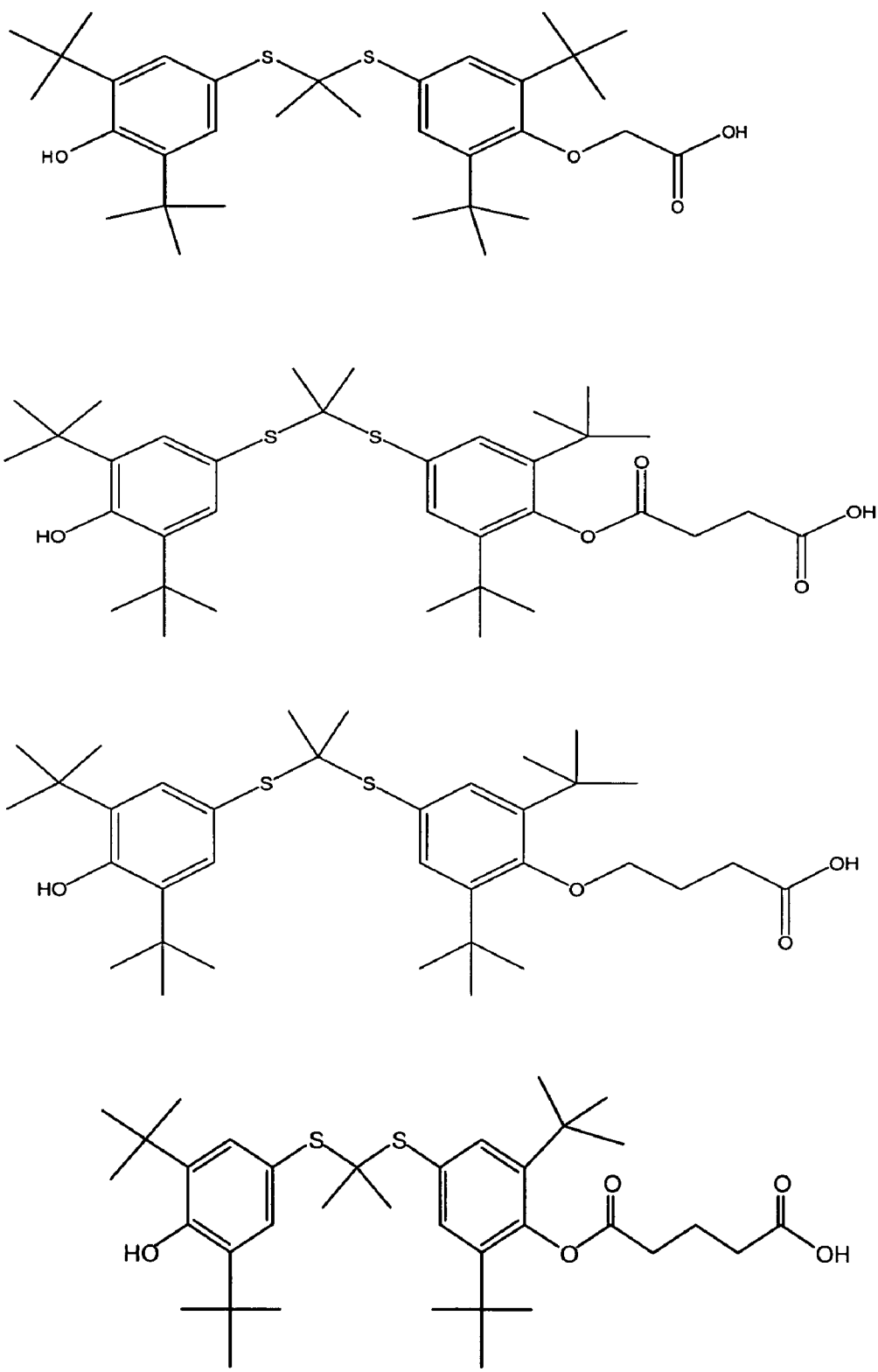
FIG. 7 shows non-limiting examples of 4-(carboxylic acid bearing) probucol derivatives that may be separated using the methods disclosed herein.

FIGS. 1, 2, 3, 4, 5, and 6 schematically show particular, non-limiting embodiments of the invention. The invention disclosed herein may be particularly useful in separating the compounds shown in FIG. 7 and/or salts thereof from their di-carboxy substituted counterparts.

DEFINITIONS

The following definitions are provided in order to aid those skilled in the art in understanding the detailed description of the present invention.

The terms "alkyl" or "alk", alone or in combination, unless otherwise specified, means a saturated straight or branched primary, secondary, or tertiary hydrocarbon, for example, 1, 2, 3, 4, 5, 6, 7, 8, 9, 10, 11, 12, 13, 14, 15 or 16 carbon atoms, including, but not limited to methyl, ethyl, propyl, isopropyl, butyl, isobutyl, t-butyl, and sec-butyl. The alkyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

The term "alkenyl", alone or in combination, means a non-cyclic alkyl, for example, of 2 to 10 carbon atoms having one or more unsaturated carbon-carbon bonds. The alkenyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

The term "alkynyl", alone or in combination, means an alkyl, for example, of 2 to 10 carbon atoms having one or more triple carbon-carbon bonds, including but not limited to ethynyl and propynyl. The alkynyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

The term "aryl", alone or in combination, means a carbocyclic aromatic system containing, for example, one, two or three rings wherein such rings may be attached together in a pendent manner or may be fused. The "aryl" group can be optionally substituted where possible with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthio, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art. In addition, adjacent groups on an "aryl" ring may combine to form a 5- to 7-membered saturated or partially unsaturated carbocyclic, aryl, heteroaryl or heterocyclic ring, which in turn may be substituted as above.

The term "acyl", alone or in combination, means a group of the formula —C(O)R', wherein R' is for example alkyl, alkenyl, alkynyl, aryl, or aralkyl group.

The terms "carboxylic acid", "carboxy", "COOH" and "C(O)OH" are used interchangeably.

The terms "halo" and "halogen" and "halide", alone or in combination, means chloro, bromo, iodo or fluoro.

The term "amino", alone or in combination, means a group of the formula NR'R", wherein R' and R" are independently selected, for example, from a group consisting of a bond, hydrogen, alkyl, aryl, alkaryl, and aralkyl, wherein said alkyl, aryl, alkaryl and aralkyl may be optionally substituted where possible as defined above.

The term "nitro", alone or in combination, denotes the radical —NO$_2$.

The term "substituted", means that one or more hydrogen on the designated atom or substituent is replaced with a selection from the indicated group, provided that the designated atom's normal valency is not exceeded, and the that the substitution results in a stable compound. When a subsitutent is "oxo" (keto) (i.e., =O), then 2 hydrogens on the atom are replaced. If the term is used without an indicating group, the indicating group is selected from the group consisting of protected hydroxyl, alkyl, alkenyl, acyl, nitro, protected amino, halo, protected carboxy, epoxide, and cyano.

The terms "heteroaryl", alone or in combination, includes an aryl as defined herein containing at least one heteroatom selected from sulfur, oxygen, nitrogen or phosphorus. The heteroaryl may optionally be substituted as that term is used herein and/or substituted with a protecting group as that term is used herein. In addition, adjacent groups on the heteroaryl may combine to form a 5- to 7-membered carbocyclic, aryl, heteroaryl, which in turn may be substituted as above. Non-limiting examples of heteroaryls are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl, wherein said heteroaryl can be optionally substituted.

The term "heterocyclic" alone or in combination refers to a nonaromatic cyclic group that can include alkyl moieties which may be substituted, and wherein there is at least one heteroatom, such as oxygen, sulfur, nitrogen, or phosphorus in the ring. Nonlimiting examples are morpholine, piperidine, piperazine, pyrrolidine, azetidine, and tetrahydrofuran. The heterocyclic group can be optionally substituted with any soluble atom or group, including but not limited to one or more moieties selected from the group consisting of hydroxyl, halo, alkyl, aryl, alkenyl, alkynyl, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, T., et al., "Protective Groups in Organic Synthesis," John Wiley and Sons, Third Edition, 1998, hereby incorporated by reference.

The term "polar or charged functionality" means a polar or charged group which maybe attached in place of one or more hydrogen atoms. Non limiting examples include carboxy, hydroxy, amino, epoxide, etc.

The terms "protecting group" or "protected" means a substituent that protects various sensitive or reactive groups present, so as to prevent said groups from interfering with a reaction. Such protection may be carried out in a well-known manner as taught by Greene, T. M. and Wuts, P. G. M., in *Protective Groups in Organic Synthesis*, John Wiley and Sons, Third Edition, 1999; Kocienski, P. J., in *Protecting Groups*, Thieme Medical Publications, $2^{nd}$ Edition, 2000; or similar texts. The protecting group may be removed after the reaction in any manner known by those skilled in the art. Non-limiting examples of protecting groups include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl. For example, a protected carboxy could be selected from one of the following:

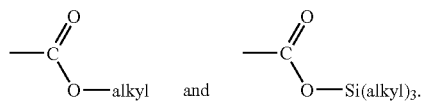

The term "linker" as used herein refers to a divalent organic linking group which does not adversely react with flanking molecules —O— or —CO$_2$H. In non-limiting embodiments, the linker may be an aliphatic, alkyl, aromatic, alkenyl, alkynyl, ester, amine, amide, heterocyclic, heteroaromatic, alkaryl, aralkyl, acyl.

EXAMPLES

The following examples are provided to illustrate the present invention and are not intended to limit the scope thereof. Those skilled in the art will readily understand that known variations of the conditions and processes of the following procedures can be used and are within the scope of the invention. The materials required for the embodiments and the examples are either known in the literature, readily commercially available, or can be made by known methods from known starting materials by those skilled in the art.

Example 1

Ex-1A: A 1 L 2-neck round bottom flask equipped with an addition funnel, temperature probe and N$_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 192.6 g anhydrous THF was added over 30 min. The temperature over the addition was maintained between 40-45° C. After the addition was complete the reaction mixture was allowed to stir for 40 min. Analysis by HPLC indicated 58.3% MSP, 12.0% DSP and 27.5% probucol.

The reaction was quenched by the slow addition of 98.0 g (370 mmol) of 4 N HCl and 148.5 g of water at 40-50° C. After the quench, the reaction mixture was cooled to 20° C. and the phases were separated. The organic layer was washed with 160 g of water. The organic layer was washed a second time with 160 g of water. Analysis by HPLC of the organic phase (414.01 g) indicated 58.7% MSP, 12.6% DSP, and 26.1% probucol.

Ex-1B: To 47.31 g of the organic solution obtained from Ex-1A were added 3.45 g (14.4 mmol) of 5 N NaOH and 20 mL water. The solution was concentrated via distillation at 70° C. to remove the tetrahydrofuran and then cooled to ambient temperature. Ethyl acetate (50 mL) and toluene (50 mL) were added and the layers were cut. Analysis by HPLC of the organic phase indicated 48% MSP, 0.25% DSP, and 52% probucol, and the aqueous layer contained 68% MSP, 22% DSP, and 6% probucol.

Example 2

Ex-2: To 43.92 g of the organic solution obtained from Ex-1A were added 1.94 g (8.1 mmol) of 5 N NaOH and 20 mL water. The solution was concentrated via distillation at 70° C. to remove the tetrahydrofuran and then cooled to ambient temperature. Ethyl acetate (50 mL) and toluene (50 mL) were added and the layers were cut. Analysis by HPLC of the organic phase indicated 66% MSP, 1.4% DSP, and 32% probucol.

Example 3

Ex-3: To 32.11 g of the organic solution obtained from Ex-1A were added 7.42 mL (7.42 mmol) of 1 N LiOH and 20 mL water. The solution was concentrated via distillation at 70° C. to remove the tetrahydrofuran and then cooled to ambient temperature. Ethyl acetate (50 mL) and toluene (50 mL) were added and the layers were cut. Analysis by HPLC of the organic phase indicated 66% MSP, 1.9% DSP, and 32% probucol. The aqueous layer was extracted with additional ethyl acetate (25 mL) and toluene (25 mL). Analysis by HPLC of the organic phase indicated 67% MSP, 1% DSP, and 32% probucol, and the aqueous phase contained 22% MSP, 65% DSP, and 0.3% probucol.

Example 4

Ex-4: To 41.26 g of the organic solution obtained from Ex-1A were added 1.91 g (7.96 mmol) of 5 N NaOH and 20 mL water. The solution was concentrated via distillation at 70° C. to remove the tetrahydrofuran and then cooled to ambient temperature. Toluene (50 mL) was added and the layers were cut. Analysis by HPLC of the organic phase indicated 66% MSP, 1.3% DSP, and 32% probucol, and the aqueous phase contained 26% MSP, 66% DSP, and 0.3% probucol.

Example 5

Ex-5: To 46.62 g of the organic solution obtained from Ex-1A were added 2.03 g (8.46 mmol) of 5 N NaOH and 20 mL water. Toluene (50 mL) was added and the layers were cut. Analysis by HPLC of the organic phase indicated 66% MSP, 1.8% DSP, and 32% probucol, and the aqueous phase contained 31% MSP, 57% DSP, and 0.6% probucol.

Example 6

Ex-6A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 194.7 g anhydrous THF was added over 30 min. The temperature over the addition was maintained between 40-45° C. After the addition was complete the reaction mixture was allowed to stir for 1 hour. Analysis by HPLC indicated 56.7% MSP, 11.0% DSP and 30.2% probucol.

The reaction was quenched by the slow addition of 98.1 g (370 mmol) of 4 N HCl and 148.0 g of water at 40-50° C. After the quench, the reaction mixture was cooled to 20° C. and the phases were separated. The organic layer was washed with 160 g of water. The organic layer (401.37 g) was washed a second time with 160 g of water. Analysis by HPLC of the organic phase indicated 58.0% MSP, 12.7% DSP, and 26% probucol.

Ex-6B: To 42.61 g of the organic solution obtained from Ex-6A were added 13.5 mL (13.5 mmol) of 1 N LiOH and 4 mL water. The solution was concentrated via distillation at 70° C. to remove the tetrahydrofuran and then cooled to ambient temperature. Ethyl acetate (37 g) was added and the layers were cut. Analysis by HPLC of the organic phase indicated 48% MSP, 1.7% DSP, and 50% probucol, and the aqueous layer contained 64% MSP, 18% DSP, and 15% probucol.

Example 7

Ex-7: To 39.47 g of the organic solution obtained from Ex-6A were added 10 mL (10.0 mmol) of 1 N LiOH and 6 mL water. The solution was concentrated via distillation at 70° C. to remove the tetrahydrofuran and then cooled to ambient temperature. Ethyl acetate (37 g) was added and the layers were cut. Analysis by HPLC of the organic phase indicated 58% MSP, 2% DSP, and 39% probucol, and the aqueous layer contained 58% MSP, 30% DSP, and 5% probucol.

Example 8

Ex-8: To 40.18 g of the organic solution obtained from Ex-6A were added 6.3 mL (6.3 mmol) of 1 N LiOH and 12 mL water. The solution was concentrated via distillation at 70° C. to remove the tetrahydrofuran and then cooled to ambient temperature. Ethyl acetate (37 g) was added and the layers were cut. Analysis by HPLC of the organic phase indicated 63% MSP, 6% DSP, and 30% probucol, and the aqueous layer contained 27% MSP, 56% DSP, and 1% probucol.

Example 9

Ex-9: To 52.74 g of the organic solution obtained from Ex-6A were added 16.7 mL (16.7 mmol) of 1 N LiOH and 4 mL water. Ethyl acetate (37 g) was added and the layers were cut. Analysis by HPLC of the organic phase indicated 54% MSP, 4% DSP, and 40% probucol, and the aqueous layer contained 62% MSP, 21% DSP, and 12% probucol.

Example 10

Ex-10: To 36.87 g of the organic solution obtained from Ex-6A were added 2.94 g (12.25 mmol) of 5 N KOH and 15 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 45% MSP, 0.7% DSP, and 54% probucol, and the aqueous layer contained 66% MSP, 20% DSP, and 10% probucol.

Example 11

Ex-11: To 34.34 g of the organic solution obtained from Ex-6A were added 2.19 g (9.13 mmol) of 5 N KOH and 15 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 57% MSP, 1.6% DSP, and 41% probucol, and the aqueous layer contained 60% MSP, 29% DSP, and 5% probucol.

Example 12

Ex-12: To 29.93 g of the organic solution obtained from Ex-6A were added 1.48 g (6.17 mmol) of 5 N KOH and 15 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 63% MSP, 3% DSP, and 33% probucol, and the aqueous layer contained 39% MSP, 49% DSP, and 1.5% probucol.

Example 13

Ex-13: To 37.05 g of the organic solution obtained from Ex-6A were added 1.18 g (4.92 mmol) of 5 N KOH and 15 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 62% MSP, 8.8% DSP, and 29% probucol, and the aqueous layer contained 22% MSP, 55% DSP, and 1% probucol.

Example 14

Ex-14: To 32.92 g of the organic solution obtained from Ex-6A were added 1.0 g (4.17 mmol) of 5 N NaOH and 15 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 62% MSP, 8.5% DSP, and 29% probucol, and the aqueous layer contained 21% MSP, 55% DSP, and 0.8% probucol.

Example 15

Ex-15: To 30.30 g of the organic solution obtained from Ex-6A were added 3.89 mL (3.89 mmol) of 1 N LiOH and 11 mL water. The solution was concentrated via distillation at 70° C. to remove the tetrahydrofuran and then cooled to ambient temperature. Ethyl acetate (26 g) was added and the layers were cut. Analysis by HPLC of the organic phase indicated 62% MSP, 8.8% DSP, and 29% probucol, and the aqueous layer contained 18% MSP, 57% DSP, and 0.7% probucol.

Example 16

Ex-16: 6.65 g of the organic solution obtained from Ex-6A was concentrated via distillation at 70° C. to remove the tetrahydrofuran and then diluted with heptanes to the original volume. The resulting solution was again concentrated to ⅕ volume at 70° C. and diluted to the original volume with heptanes. The resulting slurry was filtered at 70° C. Analysis by HPLC of the wetcake indicated 36% MSP, 51% DSP, and 11% probucol. The hot filtrate was then allowed to cool to ambient temperature overnight without stirring and was then filtered. Analysis by HPLC of the wetcake indicated 91% MSP, 2.3% DSP, and 3% probucol, and the filtrate contained 21% MSP, 0% DSP, and 77% probucol.

Example 17

Ex-17A: A 500 gallon jacketed reactor equipped with baffles, a condenser and a pitched-blade turbine agitator was charged with 150 kg (290 mol) probucol and 220 kg THF. To this solution, at 20° C., was added 397 kg (560 mol) of 1.41 M benzylmagnesium chloride in THF at such a rate that the maximum temperature was less than 37° C. After the addition was complete, the mixture was heated to about 40° C. and a solution of 29.5 kg (295 mol) succinic anhydride in 298 kg THF was added over 20 min. The temperature over the addition was maintained at 40-45° C. After the addition was complete the reaction mixture was allowed to stir for 30 min. Analysis by HPLC indicated 60.4% MSP, 12.6% DSP, and 25.4% probucol. An additional charge of 2.9 kg (29.5 mol) succinic anhydride in 29.8 kg THF was loaded to the reactor over 10 min. After the addition was complete the reaction mixture was allowed to stir for 15 min. Analysis by HPLC indicated 62.4% MSP, 16.4% DSP, and 19.7% probucol. The reaction was quenched with the slow addition of 161 kg of 13.7 wt % HCl at a temperature of 40-50° C. After the quench, the reaction mixture was cooled to 25° C. The mixture was allowed to settle for 30 min and 220 kg of aqueous phase was removed (the aqueous layer was pH 0). The organic layer was washed with 147 kg of 20% brine, and 137 kg of aqueous phase was removed. The organic layer was washed with 147 kg of 20% brine, and 154 kg of aqueous phase was removed. To the organic layer were added 113 kg of 20% brine and 75 kg of 17.0 wt % NaOH. The mixture was allowed to settle for 2 hours and 100 kg of aqueous phase was removed (the aqueous layer was pH 9.8).

The volume of the organic phase was reduced by about ½ via atmospheric distillation and 532 kg of distillate was removed overhead. The distillation was continued while adding 719 kg of heptanes, and an additional 777 kg of distillate was collected. GC analysis at the end of the distillation indicated that the THF concentration was less than 2 wt % relative to heptanes. An additional 612 kg of heptanes was added over 90 min while maintaining the internal temperature above 70° C. The mixture was allowed to cool to 20° C. over 70 min and then held at this temperature for about 1 hour. The slurry was cooled to 5° C. and 57 kg of water was added. The slurry was allowed to stir for 90 min. The slurry was filtered in a 30" diameter centrifuge with a 1-3 micron polypropylene filter cloth. Each centrifuge load of wetcake was rinsed with 23 kg of ambient temperature heptanes, and 1045 kg of combined mother liquor and rinse was collected. A total of 293 kg of MSP/DSP sodium salt wetcake (containing water and heptanes) was collected in 4 loads. The average wetcake composition by HPLC was 76.6% MSP, 21.8% DSP, and 1.5% probucol. HPLC analysis of the mother liquor indicated 96.8% probucol, and 3.2% MSP.

Ex-17B: A 300 gallon jacketed reactor equipped with baffles, a condenser, and a pitched-blade turbine agitator was charged with 291 kg of MSP/DSP sodium salt wetcake (containing water and heptanes) obtained from Ex-17A. The wetcake was slurried in 1045 kg of toluene and heated to 75° C. for about 30 min. The mixture was cooled to 45° C. and held for 40 min. The slurry was filtered at 45° C. in a 30 gallon Nutsche pressure filter with a 1-3 micron polypropylene filter cloth. The filtrate from the Nutsche was transferred to a 500 gallon jacketed reactor equipped with baffles, a condenser, and a pitched-blade turbine agitator. A total of 46 kg of wetcake was collected in 4 loads. The average wetcake composition of the first 3 loads was 22.2% MSP, 77.5% DSP, and 0.3% probucol. The final load of wetcake was rinsed with 65 kg of toluene. The composition of the final load of wetcake was 3.1% MSP and 96.9% DSP. The combined rinse and filtrate contained 87.2% MSP and 12.8% DSP, as measured by HPLC.

The filtrate was transferred back to the 300 gallon jacketed reactor and heated to 45° C., and then filtered in a 30" diameter centrifuge with a 1-3 micron polypropylene cloth. The filtrate from the centrifuge was transferred to the 500 gallon jacketed reactor. A total of 66 kg of wetcake was collected in 2 loads. The final load of wetcake was rinsed with 9 kg of toluene. The average centrifuge wetcake composition was 24.7% MSP, 75% DSP, 0.3% probucol. The combined rinse and filtrate contained 95.4% MSP, 3.2% DSP, and 1.4% probucol.

The filtrate was partially acidified by adding 39.9 kg (150 mol) of 13.7 wt % HCl and 234 kg of water. After stirring for 1 hour at 25° C., the mixture was allowed to settle for 1.5 hours and 296 kg of aqueous phase was removed (pH of the aqueous layer was 7.4). To the organic phase were added 190 kg of water and 190 kg acetone. After stirring for 1 hour at 50° C., the mixture was allowed to settle for 3 hours and 241 kg of aqueous phase was removed. To the organic phase were added 325 kg of water and 168 kg acetone. After stirring for 30 min at 50° C., the mixture was allowed to settle for 30 min and 392 kg of aqueous phase was removed. The composition of the remaining organic phase by HPLC was 96.9% MSP, 1.65% DSP, and 1.3% probucol.

To the organic phase was added 340 kg of water. After stirring for 30 min at 50° C., the mixture was allowed to settle for 2 hours and 403 kg of aqueous phase was removed. To the organic phase were added 303 kg of water and 45 kg of acetone. After stirring for 40 min at 50° C., the mixture was allowed to settle for 75 min and 353 kg of aqueous phase was removed. To the organic phase were added 179 kg of water and 1.9 kg (8 mol) of 17 wt % NaOH. After stirring for 35 min at 25° C., the mixture was allowed to settle for 1 hour and 192 kg of aqueous phase was removed. To the organic phase was added 340 kg of water. After stirring for 30 min at 25° C., the mixture was allowed to settle for 1 hour and 484 kg of aqueous phase was removed. The composition of the remaining organic phase by HPLC was 98.5% MSP, 0.15% DSP, and 1.35% probucol.

To the organic phase were added 576 kg of water and 0.8 kg (3.4 mol) of 17 wt % NaOH. After stirring for 30 min at 25° C., the mixture was allowed to settle for 2 hours and 597 kg of aqueous phase was removed. The composition of the remaining organic phase by HPLC was 98.5% MSP, 0.12% DSP, and 1.36% probucol.

To the organic phase was added 170 kg of water. After stirring for 30 min at 25° C., the mixture was allowed to settle for 1 hour and 144 kg of aqueous phase was removed. The composition of the remaining organic phase by HPLC was 98.5% MSP, 0.12% DSP, and 1.35% probucol.

The organic phase was acidified by adding 20 kg (75 mol) of 13.7 wt % HCl and 168 kg of water. After stirring for 1 hour at 25° C., the mixture was allowed to settle for 1 hour and 211 kg of aqueous phase was removed (pH of the aqueous layer was 0.8). The organic phase was washed with 159 kg of water, and 268 kg of aqueous phase was removed. The organic phase was concentrated by atmospheric distillation until about 636 kg of distillate had been collected. The distillation was continued while adding 272 kg of heptanes, and an additional 135 kg of distillate was collected. GC analysis at the end of the distillation indicated that the toluene concentration was less than 40 wt % relative to heptanes. The temperature was adjusted to 80° C. and the mixture was diluted with an additional 499 kg of heptanes.

The mixture was cooled below 5° C. and the resulting slurry was held for 12 hours. The slurry was filtered in a 30" diameter centrifuge with a 1-3 micron polypropylene filter cloth. Each centrifuge load of wetcake was rinsed with 45 kg of cold heptanes, and the 500 gallon jacketed reactor was rinsed with 289 kg of heptanes. A total of 1181 kg of combined mother liquor and rinse was collected. A total of 122 kg of wetcake was collected in 4 loads. The average wetcake composition by HPLC was 99.8% MSP, 0.15% DSP and 0.03% probucol. The wetcake was dried under vacuum for 8.5 hours at 60° C. in a conical agitated dryer to give 78.2 kg of dry MSP.

Ex-17C: A 200 gallon jacketed reactor equipped with baffles, a condenser, and a retreat-curve agitator was charged with 78.2 kg of MSP obtained from Ex-17B and 164 kg of acetone. The mixture was stirred at 40° C. for 1 hour until the solid was completely dissolved. The solution was transferred through a 0.2 micron polish filter to a 300 gallon jacketed reactor equipped with baffles, a condenser, and a retreat-curve agitator. To the solution was added 18.2 kg of water. The solution was cooled and nucleation occurred at about –4° C. The slurry was held below –5° C. for about 3 hours and then an additional 156 kg of water was added over about 12 min. The slurry was warmed to 25° C. and filtered in a 30" diameter centrifuge with a 1-3 micron polypropylene filter cloth. A total of 255 kg of mother liquor was collected. A total of 121 kg of wetcake was collected in 3 loads. The wetcake was dried under vacuum for 40 hours at 40-70° C. in a conical agitated dryer, to give 67.5 kg of MSP.

Example 18

Ex-18A: A 500 gallon jacketed reactor equipped with baffles, a condenser, and a pitched-blade turbine agitator was charged with 150 kg (290 mol) probucol and 180 kg THF. To this solution, at 20° C., was added 397 kg (560 mol) of 1.41 M benzylmagnesium chloride in THF at such a rate that the maximum temperature was less than 41° C. After the addition was complete, the mixture was heated to about 40° C. and a solution of 29.9 kg (299 mol) succinic anhydride in 303 kg THF was added over 35 min. The temperature over the addition was maintained at 40-45° C. After the addition was complete the reaction mixture was allowed to stir for 30 min. Analysis by HPLC indicated 57.3% MSP, 12.3% DSP, and 28.8% probucol. The reaction was quenched with the slow addition of 181 kg of 13.7 wt % HCl at a temperature of 40-50° C. After the quench, the reaction mixture was allowed to cool to 20-25° C. The mixture was allowed to settle for 30 min and 246 kg of aqueous phase was removed (the aqueous layer was pH 0). The organic layer was washed with 299 kg of water, and 392 kg of aqueous phase was removed. The organic layer was washed with 331 kg of 2% brine, and 485 kg of aqueous phase was removed. To the organic layer were added 407 kg of 10% brine and 84 kg of 17.0 wt % NaOH. The mixture was allowed to settle for 120 min and 429 kg of aqueous phase was removed (the aqueous layer was pH 12.8).

The volume of the organic phase was reduced by about ½ via atmospheric distillation and 355 kg of distillate was collected overhead. The distillation was continued while adding 485 kg of heptanes, and an additional 540 kg of distillate was collected. GC analysis at the end of the distillation indicated that the THF concentration was less than 2.2 wt % relative to heptanes.

An additional 612 kg of heptanes was added over 75 min maintaining the internal temperature above 70° C. The mixture was allowed to cool to 20° C. over 70 min and then held at this temperature for about 2.5 hours. The slurry was filtered in a 30" diameter centrifuge with a 1-3 micron polypropylene filter cloth. Each centrifuge load of wetcake was rinsed with 45 kg of ambient temperature heptanes, and 867 kg of combined mother liquor and rinse was collected. A total of 243 kg of MSP/DSP sodium salt wetcake (containing water and heptanes) was collected in 3 loads. The average wetcake composition by HPLC was 81.0% MSP, 17.2% DSP, and 1.8% probucol. HPLC analysis of the mother liquor indicated 99.8% probucol.

Ex-18B: A 300 gallon jacketed reactor equipped with baffles, a condenser, and a pitched-blade turbine agitator was charged with 243 kg of MSP/DSP sodium salt wetcake (containing water and heptanes) obtained from Ex-18A. The wetcake was slurried in 862 kg of ethyl acetate and heated to 70° C. for about 15 min. The mixture was cooled to 25° C. and held for 2 hours. The slurry was filtered in a 30" diameter centrifuge with a 1-3 micron polypropylene filter cloth. Each centrifuge load of wetcake was rinsed with 23 kg of ethyl acetate. A total of 55 kg of wetcake was collected in 2 loads, the average composition by HPLC was 3.7% MSP and 96.2% DSP. The composition of the combined mother liquor and rinse was 92.2% MSP, 1.1% DSP, and 6.7% probucol. The elevated probucol concentration was attributed to contamination of either the equipment or sample with heptane filtrate from the previous process step.

A total of 1003 kg of ethyl acetate mother liquor and rinse was loaded to a 500 gallon jacketed reactor equipped with baffles, a condenser, and a pitched-blade turbine agitator. The estimated weight of MSP sodium salt in the filtrate was 106 kg (166 mol), assuming a 57% yield of MSP from probucol, up to this point in the process. About ⅔ of the solvent was removed by vacuum distillation at 200 mmHg. The distillation was continued while adding 670 kg of toluene, and a total of 1296 kg of distillate was collected. GC analysis at the end of the distillation indicated that the ethyl acetate concentration was less than 2 wt % relative to toluene.

The mixture was diluted with an additional 621 kg of toluene and then partially acidified by adding 40.4 kg (152 mol) of 13.7 wt % HCl and 161 kg of water. After stirring for 1 hour at 25° C., the mixture was allowed to settle for 30 min and 200 kg of aqueous phase was removed (pH of the aqueous layer was 7.5). To the organic phase were added 303 kg of water and 300 kg acetone. After stirring for 30 min at 50° C., the mixture was allowed to settle for 1 hour. An attempt was made to separate the phases, but the material that was drained from the reactor was an emulsion. The collected material was reloaded to the reactor along with the initial aqueous phase. 18.0 kg of 13.7 wt % HCl and 27 kg of water were added. After stirring for 1 hour at 25° C., the mixture was allowed to settle for 30 min and 419 kg of aqueous phase was removed (pH of the aqueous layer was 1.1). The organic phase was washed with 170 kg of water, and 205 kg of aqueous phase was removed.

To the organic phase were added 312 kg of water, 90 kg of acetone, and 3.9 kg (16.6 mol) of 17 wt % NaOH. After stirring at 50° C. for 1 hour, the mixture was an emulsion. The mixture was re-acidified by adding 14 kg of 13.7 wt % HCl and 9 kg of water. After stirring for 1 hour at 25° C., the mixture was allowed to settle for 30 min and 416 kg of aqueous phase was removed (pH of the aqueous layer was 1.0). The organic phase was washed with 170 kg of water, and 204 kg of aqueous phase was removed.

To the organic phase were added 312 kg of water, 90 kg of acetone, and 0.9 kg (3.8 mol) of 17 wt % NaOH. After stirring for 30 min at 50° C., the mixture was allowed to settle for 30 min and 362 kg of aqueous phase was removed. The composition of the remaining organic phase by HPLC was 97.3% MSP, 0.6% DSP, and 2.1% probucol.

To the organic phase were added 312 kg of water, 48 kg of acetone, and 0.5 kg (2.1 mol) of 17 wt % NaOH. After stirring for 30 min at 50° C., the mixture was allowed to settle for 30 min and 366 kg of aqueous phase was removed. The composition of the remaining organic phase by HPLC was 97.7% MSP, 0.23% DSP, and 2.1% probucol.

To the organic phase were added 303 kg of water and 57 kg of acetone. After stirring for 30 min at 50° C., the mixture was allowed to settle for 35 min and 357 kg of aqueous phase was removed. The composition of the remaining organic phase by HPLC was 97.7% MSP, 0.19% DSP, and 2.1% probucol.

To the organic phase were added 312 kg of water, 57 kg of acetone, and 0.4 kg (1.7 mol) of 17 wt % NaOH. After stirring for 30 min at 50° C., the mixture was allowed to settle for 30 min and 365 kg of aqueous phase was removed. The composition of the remaining organic phase by HPLC was 97.8% MSP, 0.06% DSP, and 2.1% probucol.

The organic phase was acidified by adding 16 kg (60 mol) of 13.7 wt % HCl and 160 kg of water. After stirring for 135 min at 25° C., the mixture was allowed to settle for 30 min and 218 kg of aqueous phase was removed (pH of the aqueous layer was 0.7). The organic phase was washed with 151 kg of water, and 178 kg of aqueous phase was removed. The organic phase was concentrated by atmospheric distillation until about 757 kg of distillate had been collected. The distillation was continued while adding 433 kg of heptanes, and an additional 449 kg of distillate was collected. GC analysis at the end of the distillation indicated that the toluene concentration was less than 40 wt % relative to heptanes. The temperature was adjusted to 80° C. and the mixture was diluted with an additional 499 kg of heptanes.

The mixture was cooled below 5° C. and the resulting slurry was held for 3 hours and then filtered in a 30" diameter centrifuge using a 1-3 micron polypropylene filter cloth. Each centrifuge load of wetcake was rinsed with 45 kg of cold heptanes, and a total of 808 kg of combined mother liquor and rinse was collected. A total of 141 kg of wetcake was collected in 3 loads. The average wetcake composition by HPLC was 99.86% MSP, 0.054% DSP, 0.08% probucol. The wetcake was dried under vacuum for 6 hours at 75° C. in a conical agitated dryer to give 98.7 kg of dry MSP.

Ex-18C: A 200 gallon jacketed reactor equipped with baffles, a condenser, and a retreat-curve agitator was charged with 98.2 kg of MSP obtained from Ex-18B and 207 kg of acetone. The mixture was stirred at 40° C. for 1 hour until the solid was completely dissolved. The solution was transferred through a 0.2 micron polish filter to a 300 gallon jacketed reactor equipped with baffles, a condenser, and a retreat-curve agitator. To the solution was added 23 kg of water. The solution was cooled and nucleation occurred at about −6° C. The slurry was held below −5° C. for about 3.5 hours and then an additional 197 kg of water was added over 15 min. The slurry was warmed to 25° C. and filtered in a 30" diameter centrifuge with a 1-3 micron polypropylene filter cloth. The 300 gallon jacketed reactor was rinsed with a mixture of 113 kg of water and 113 kg of acetone. A total of 583 kg of mother liquor was collected. A total of 138 kg of wetcake was collected in 3 loads. The wetcake was dried under vacuum for 22 hours at 65-75° C. in a conical agitated dryer, to give 90.9 kg of MSP.

Example 19

Ex-19A: A 500 gallon jacketed reactor equipped with baffles, a condenser and a pitched-blade turbine agitator was charged with 150 kg (290 mol) probucol and 179 kg THF. To this solution, at 20° C., was added 397 kg (560 mol) of 1.41 M benzylmagnesium chloride in THF at such a rate that the maximum temperature was less than 40° C. After the addition was complete, the mixture was heated to about 40° C. and a solution of 29.5 kg (295 mol) succinic anhydride in 298 kg THF was added over 30 min. The temperature over the addition was maintained at 40-45° C. After the addition was complete the reaction mixture was allowed to stir for 75 min. Analysis by HPLC indicated 60.1% MSP, 12.7% DSP, and 25.6% probucol. The reaction was quenched with the slow addition of 177 kg of 13.7 wt % HCl at a temperature of 40-50° C. After the quench, the reaction mixture was allowed to cool to 20-25° C. The mixture was allowed to settle for 30 min and 246 kg of aqueous phase was removed (the aqueous layer was pH<0). The organic layer was washed with 303 kg of 3% brine, and 355 kg of aqueous phase was removed. The organic layer was washed with 303 kg of 3% brine, and 424 kg of aqueous phase was removed. To the organic layer were added 405 kg of 10% brine and 88 kg of 17.0 wt % NaOH. The mixture was allowed to settle for 2 hours and 436 kg of aqueous phase was removed (the aqueous layer was pH 12.8).

The volume of the organic phase was reduced by about 12 via atmospheric distillation, and 408 kg of distillate was collected overhead. The distillation was continued while adding 590 kg of heptanes, and an additional 620 kg of distillate was collected. GC analysis at the end of the distillation indicated that the THF concentration was less than 2 wt % relative to mixed heptanes.

An additional 612 kg of heptanes was added over 65 min maintaining the internal temperature above 70° C. The mixture was allowed to cool to 20° C. over 70 min and then held at this temperature for about 2 hours. The slurry was filtered in a 30" diameter centrifuge with a 1-3 micron polypropylene filter cloth. Each centrifuge load of wetcake was rinsed with a different amount of ambient temperature heptanes ranging from 23 kg to 68 kg, and 917 kg of combined mother liquor and rinse was collected. A total of 233 kg of MSP/DSP sodium salt wetcake (containing water and heptanes) was collected in 4 loads. The average wetcake composition by HPLC was 81.6% MSP, 17.0% DSP, and 1.4% probucol. HPLC analysis of the mother liquor indicated 99.8% probucol.

Ex-19B: A 300 gallon jacketed reactor equipped with baffles, a condenser, and a pitched-blade turbine agitator was charged with 228 kg of MSP/DSP sodium salt wetcake (containing water and heptanes) obtained from Ex-19A. The wetcake was slurried in 863 kg of ethyl acetate and heated to 70° C. for about 20 min. The mixture was cooled to 25° C. and held for 2 hours. The slurry was filtered in a 30" diameter centrifuge with a 1-3 micron polypropylene filter cloth. Each centrifuge load of wetcake was rinsed with 23 kg of ethyl acetate. A total of 55 kg of wetcake was collected in 2 loads, the average composition by HPLC was 3.7% MSP and 96.3% DSP. The composition of the combined mother liquor and rinse was 97.5% MSP, 1.0% DSP, and 1.5% probucol.

A total of 1016 kg of ethyl acetate mother liquor and rinse was loaded to a 500 gallon jacketed reactor equipped with baffles, a condenser, and a pitched-blade turbine agitator. The estimated weight of MSP sodium salt in the filtrate was 108 kg (168 mol), assuming a 58% yield of MSP from probucol, up to this point in the process. About ⅔ of the solvent was removed by vacuum distillation at 200 mmHg. The distillation was continued while adding 670 kg of toluene, and a total of 1265 kg of distillate was collected. GC analysis at the end of the distillation indicated that the ethyl acetate concentration was less than 2 wt % relative to toluene.

The mixture was diluted with an additional 621 kg of toluene and the temperature was adjusted to 50° C. The toluene solution was completely acidified by adding 66 kg (248 mol) of 13.7 wt % HCl and 119 kg of water. After stirring for 1 hour at 25° C., the mixture was allowed to settle for 30 min and 190 kg of aqueous phase was removed (pH of the aqueous layer was 0.6). The organic phase was washed with 181 kg of water, and 185 kg of aqueous phase was removed.

After charging 312 kg of water and 240 kg of acetone to the organic phase, the mixture was heated to 50° C. and 2.2 kg of 17.0 wt % NaOH was added. After stirring for 30 min at 50° C., the mixture was allowed to settle for 1 hour and 349 kg of aqueous phase was removed (pH of the aqueous layer was 7.5). The composition of the remaining organic phase by HPLC was 98.2% MSP, 0.3% DSP, and 1.5% probucol. The composition of the aqueous phase was 10% MSP and 90% DSP An additional 303 kg of water and 57 kg of acetone was charged to the organic phase. After stirring for 30 min at 50° C., the mixture was allowed to settle for 1 hour and 350 kg of aqueous phase was removed. The composition of the remaining organic phase by HPLC was 98.4% MSP, 0.07% DSP, and 1.5% probucol.

The organic phase was acidified by adding 14 kg of 13.7 wt % HCl and 142 kg of water. After stirring for 1 hour at 25° C., the mixture was allowed to settle for 30 min and 188 kg of aqueous phase was removed (pH of the aqueous layer was 0.6). The organic phase was washed with 152 kg of water, and 176 kg of aqueous phase was removed. The organic phase was concentrated by atmospheric distillation until about 804 kg of distillate had been collected.

The distillation was continued while adding 408 kg of heptanes, and an additional 464 kg of distillate was collected. GC analysis at the end of the distillation indicated that the toluene concentration was less than 40 wt % relative to heptanes. The temperature was adjusted to 80° C. and the mixture was diluted with an additional 499 kg of heptanes.

The mixture was cooled below 5° C. and the resulting slurry was held for 1 hour. The slurry was filtered in a 30" diameter centrifuge with a 1-3 micron polypropylene filter cloth. Each centrifuge load of wetcake was rinsed with 45 kg of cold heptanes, and 796 kg of combined mother liquor and rinse was collected. A total of 146 kg of wetcake was collected in 4 loads. The average wetcake composition by HPLC was 99.89% MSP, 0.075% DSP, and 0.04% probucol. The wetcake was dried under vacuum for 12.5 hours at 75° C. in a conical agitated dryer to give 103.8 kg of dry MSP.

Ex-19C: A 200 gallon jacketed reactor equipped with baffles, a condenser, and a retreat-curve agitator was charged with 101.3 kg of MSP obtained from Ex-19B and 214 kg of acetone. The mixture was stirred at 40° C. for 1 hour until the solid was completely dissolved. The solution was transferred through a 0.2 micron polish filter to a 300 gallon jacketed reactor equipped with baffles, a condenser, and a retreat-curve agitator. To the solution was added 24 kg of water. The solution was cooled and nucleation occurred at about −6° C. The slurry was held below −5° C. for about 3 hours and then an additional 204 kg of water was added over 15 min. The slurry was warmed to 25° C. and filtered in a 30" diameter centrifuge with a 1-3 micron polypropylene filter cloth. The 300 gallon jacketed reactor was rinsed with a mixture of 113 kg of water and 113 kg of acetone. A total of 597 kg of mother liquor was collected. A total of 154 kg of wetcake was collected in 3 loads. The wetcake was dried under vacuum for 26 hours at 75° C. in a conical agitated dryer, to give 103.8 kg of MSP.

Example 20

Ex-20A: A 500 gallon jacketed reactor equipped with baffles, a condenser and a pitched-blade turbine agitator was charged with 150 kg (290 mol) probucol and 179 kg THF. To this solution, at 20° C., was added 397 kg (560 mol) of 1.41 M benzylmagnesium chloride in THF at such a rate that the maximum temperature was less than 41° C. After the addition was complete, the mixture was heated to about 40° C. and a solution of 29.5 kg (295 mol) succinic anhydride in 298 kg THF was added over 30 min. The temperature over the addition was maintained at 40-45° C. After the addition was complete the reaction mixture was allowed to stir for 100 min. Analysis by HPLC indicated 61.2% MSP, 13.4% DSP, and 23.9% probucol.

The reaction was quenched with the addition of 180 kg of 13.7 wt % HCl at a temperature of 40-50° C. After the quench, the reaction mixture was allowed to cool to 25° C. The mixture was allowed to settle for 30 min and 245 kg of aqueous phase was removed (the aqueous layer was pH 0). The organic layer was washed with 303 kg of 3% brine, and 357 kg of aqueous phase was removed. The organic layer was washed with 303 kg of 3% brine, and 422 kg of aqueous phase was removed. To the organic layer were added 405 kg of 10% brine and 90 kg of 17.0 wt % NaOH. The mixture was allowed to settle for 2 hours and 422 kg of aqueous phase was removed (the aqueous layer was pH 12.9).

The volume of the organic phase was reduced by about ½ via atmospheric distillation, and 429 kg of distillate was collected overhead. The distillation was continued while adding 500 kg of heptanes, and an additional 526 kg of distillate was collected. GC analysis at the end of the distillation indicated that the THF concentration was less than 4 wt % relative to heptanes. An additional 612 kg of heptanes was added over 80 min maintaining the internal temperature above 70° C. The mixture was allowed to cool to 20° C. over 70 min and then held at this temperature for about 2 hours. The slurry was filtered in a 30" diameter centrifuge with a 1-3 micron polypropylene filter cloth.

Due to poor filtration, the isolated wetcake and mother liquors were recombined into the 500 gallon jacketed reactor.

The slurry was concentrated via atmospheric distillation with 345 kg of distillate collected overhead. GC analysis at the end of the distillation indicated that the THF concentration was less than 0.5 wt % relative to heptanes. An additional 216 kg of heptanes was added over 15 min maintaining the internal temperature above 70° C. The mixture was allowed to cool to 20° C. over 70 min and then held at this temperature for about 3.5 hours. The slurry was filtered in a 30" diameter centrifuge with a 1-3 micron polypropylene filter cloth. Each centrifuge load of wetcake was rinsed with a different amount of ambient temperature heptanes ranging from 23 kg to 45 kg, and 833 kg of combined mother liquor and rinse was collected. A total of 221 kg of MSP/DSP sodium salt wetcake (containing water and heptanes) was collected in 3 loads. The average wetcake composition by HPLC was 81.2% MSP, 17.8% DSP, and 0.9% probucol. HPLC analysis of the mother liquor indicated 99.8% probucol, and 0.05% MSP.

Ex-20B: A 300 gallon jacketed reactor equipped with baffles, a condenser, and a pitched-blade turbine agitator was charged with 218 kg of MSP/DSP sodium salt wetcake (containing water and heptanes) obtained from Ex-20A. The wetcake was slurried in 862 kg of ethyl acetate and heated to 70° C. for 20 min. The mixture was cooled to 25° C. and held for 2 hours. The slurry was filtered in a 30" diameter centrifuge with a 1-3 micron polypropylene filter cloth. Each centrifuge load of wetcake was rinsed with 23 kg of ethyl acetate. A total of 62 kg of wetcake was collected in 3 loads, the average composition by HPLC was 10% MSP and 90% DSP. The composition of the combined mother liquor and rinse was 96.6% MSP, 1.1% DSP, and 2.3% probucol. The elevated probucol concentration was attributed to contamination of either the equipment or sample with heptane filtrate from the previous process step.

A total of 970 kg of ethyl acetate mother liquor and rinse was loaded to a 500 gallon jacketed reactor equipped with baffles, a condenser, and a pitched-blade turbine agitator. The estimated weight of MSP sodium salt in the filtrate was 108 kg (168 mol), assuming a 58% yield of MSP from probucol, up to this point in the process. About ⅔ of the solvent was removed by vacuum distillation at 200 mmHg. The distillation was continued while adding 767 kg of toluene, and a total of 1427 kg of distillate was collected. GC analysis at the end of the distillation indicated that the ethyl acetate concentration was less than 2 wt % relative to toluene.

The mixture was diluted with an additional 621 kg of toluene and then completely acidified by adding 66 kg (248 mol) of 13.7 wt % HCl and 118 kg of water. After stirring for 1 hour at 25° C., the mixture was allowed to settle for 30 min and 188 kg of aqueous phase was removed (pH of the aqueous layer was 0.9). The organic phase was washed with 181 kg of water, and 182 kg of aqueous phase was removed.

After charging 312 kg of water and 239 kg of acetone to the organic phase, the mixture was heated to 50° C. and 2.4 kg (10 mol) of 17.0 wt % NaOH was added. After stirring for 30 min at 50° C., the mixture was allowed to settle for 1 hour and 347 kg of aqueous phase was removed. The composition of the remaining organic phase by HPLC was 99.6% MSP and 0.3% DSP. The composition of the aqueous phase was 27.3% MSP and 70.1% DSP. After charging 312 kg of water and 57 kg of acetone to the organic phase, the mixture was heated to 50° C. and 0.4 kg (1.7 mol) of 17.0 wt % NaOH was added. After stirring for 30 min at 50° C., the mixture was allowed to settle for 30 min and 277 kg of aqueous phase was removed. The weight of aqueous phase collected was lower than expected, due to incomplete phase separation. When the reactor agitator was re-started, the remaining mixture formed an emulsion. The composition of the emulsion by HPLC was 98.4% MSP, 0.10% DSP, and 1.5% probucol.

The organic phase (emulsion) was acidified by adding 11 kg (41 mol) of 13.7 wt % HCl and 160 kg of water. After stirring for 1 hour at 25° C., the mixture was allowed to settle for 30 min and 378 kg of aqueous phase was removed (pH of the aqueous layer was 1.0). The composition of the remaining organic phase was 98.6% MSP, 0.06% DSP, and 1.4% probucol.

The organic phase was washed with 151 kg of water, and 173 kg of aqueous phase was removed. The organic phase was concentrated by atmospheric distillation until about 766 kg of distillate had been collected. The distillation was continued while adding 431 kg of heptanes, and an additional 442 kg of distillate was collected. GC analysis at the end of the distillation indicated that the toluene concentration was less than 40 wt % relative to heptanes. The temperature was adjusted to 80° C. and the mixture was diluted with an additional 499 kg of heptanes.

The mixture was cooled below 5° C. and the resulting slurry was held for 1 hour and then filtered in a 30" diameter centrifuge using a 1-3 micron polypropylene filter cloth. Each centrifuge load of wetcake was rinsed with 45 kg of cold heptanes, and a total of 805 kg of combined mother liquor and rinse was collected. A total of 142 kg of wetcake was collected in 3 loads. The average wetcake composition by HPLC was 99.86% MSP, 0.09% DSP, and 0.05% probucol. The wetcake was dried under vacuum for 12.5 hours at 75° C. in conical agitated dryer to give 89.3 kg of dry MSP.

Ex-20C: A 200 gallon jacketed reactor equipped with baffles, a condenser, and a retreat-curve agitator was charged with 89.1 kg of MSP obtained from Ex-20B and 187 kg of acetone. The mixture was stirred at 40° C. for 1 hour until the solid was completely dissolved. The solution was transferred through a 0.2 micron polish filter to a 300 gallon jacketed reactor equipped with baffles, a condenser, and a retreat-curve agitator. To the solution was added 21 kg of water. The solution was cooled and nucleation occurred at about −6° C. The slurry was held below −5° C. for about 3 hours and then an additional 179 kg of water was added over 15 min. The slurry was warmed to 25° C. and filtered in a 30" diameter centrifuge with a 1-3 micron polypropylene filter cloth. The 300 gallon jacketed reactor was rinsed with a mixture of 113 kg of water and 113 kg of acetone. A total of 534 kg of mother liquor was collected. A total of 132 kg of wetcake was collected in 3 loads. The wetcake was dried under vacuum for 26 hours at 75° C. in a conical agitated dryer, to give 83.1 kg of MSP.

Example 21

Ex-21: A 500 mL straight-walled, jacketed reactor equipped with a condenser, mechanical agitator, addition funnel, and $N_2$ bubbler was charged with 40.1 g (77.6 mmol) probucol and 52.9 g THF. To this solution was added 92.1 g (147.4 mmol) of 1.6 M benzylmagnesium chloride in THF at such a rate that the maximum temperature was less than 43° C. After the addition was complete, the temperature of the mixture was adjusted to about 40° C. and a solution of 8.2 g (81.9 mmol) succinic anhydride in 79.9 g THF was added over 30 min. The temperature over the addition was maintained at 40-45° C. After the addition was complete the reaction mixture was allowed to stir for 15 min. Analysis by HPLC indicated 56.9% MSP, 14.0% DSP, and 28.4% probucol.

The reaction was quenched with the slow addition of 37.8 g (142 mmol) of 4 N HCl at a temperature of 40-50° C. After the quench, the mixture cooled to 20° C. and the phases were separated (aqueous layer pH was 0-1). The organic layer was washed with 45.4 g of 20% brine. To the organic layer were added 35.7 g of 20% brine and 18.5 g (78.6 mmol) of 5N NaOH. The mixture was stirred at 20° C. for 15 min and the layers were separated (aqueous layer pH was 11).

The organic layer was concentrated by distillation at atmospheric pressure until 106 mL of distillate had been collected (reactor temperature was 72° C.). The distillation was continued while adding 160 mL of heptanes, and an additional 150 mL of distillate was collected (final reactor temperature was 83° C.). An additional 240 mL of heptanes was added over 10 min while maintaining the reactor temperature above 75° C. The slurry was cooled to 20° C. over about 1 hour and held at this temperature for 50 min. The slurry was filtered and the wetcake was washed with 106.2 g of heptanes. A total of 66.6 g of MSP/DSP sodium salt wetcake (containing water and heptanes) was collected, the composition by HPLC was 79.1% MSP, 20.1% DSP and 0.8% probucol. HPLC analysis of the filtrate indicated 2.2% MSP and 97.4% probucol.

Example 22

Ex-22: A 500 mL round bottom flask equipped with a condenser, mechanical agitator, addition funnel, and $N_2$ bubbler was charged with 40.0 g (77.4 mmol) probucol and 60 mL THF. To this solution was added 108 mL (152.3 mmol) of 1.41 M benzylmagnesium chloride in THF at such a rate that the maximum temperature was less than 43° C. After the addition was complete, the temperature of the mixture was adjusted to about 40° C. and a solution of 8.1 g (80.9 mmol) succinic anhydride in 95 mL THF was added over 30 min. The temperature over the addition was maintained at 39-41° C. After the addition was complete the reaction mixture was allowed to stir for 15 min. Analysis by HPLC indicated 61.3% MSP, 12.2% DSP, and 25.3% probucol.

The reaction was quenched with the slow addition of 48.0 g (180 mmol) of 4 N HCl at a temperature of 37-44° C. After the quench, the mixture cooled to 20° C. and the phases were separated (aqueous layer pH was 0-1). The organic layer was washed twice with 80 mL of water. To the organic layer were added 100 mL of 10% brine and 25.7 g (109 mmol) of 5N NaOH. The mixture was stirred at 20° C. for 15 min and the layers were separated (aqueous layer pH was 13).

The organic layer was concentrated by distillation at atmospheric pressure until 103 mL of distillate had been collected (reactor temperature was 70° C.). The distillation was continued while adding 160 mL of heptanes, and an additional 157 mL of distillate was collected (final reactor temperature was 75° C.). An additional 240 mL of heptanes was added while maintaining the reactor temperature at 70-75° C. The slurry was allowed to cool to 25° C. over about 1 hour and held at this temperature for 16 hours. The slurry was filtered and the wetcake was washed with 120 mL of heptanes. A total of 75.1 g of MSP/DSP sodium salt wetcake (containing water and heptanes) was collected, the composition by HPLC was 82.9% MSP, 16.3% DSP, and 0.8% probucol. HPLC analysis of the filtrate indicated >99.9% probucol.

Example 23

Ex-23A: A 500 mL round bottom flask equipped with a condenser, mechanical agitator, addition funnel, and $N_2$ bubbler was charged with 52.5 g of MSP/DSP sodium salt wetcake (wet with water and heptanes) obtained in a manner similar to Ex-22. The wetcake composition by HPLC was 77.9% MSP, 20.5% DSP and 1.5% probucol. The wetcake was slurried in 300 mL of toluene and heated to 80° C. for about 15 min. After adding 1 mL of water to the slurry, the mixture was allowed to cool to 25° C. and held for 2 hours. The slurry was filtered and the wetcake was washed with 60 mL of toluene. The composition of the wetcake by HPLC was 1.3% MSP and 98.6% DSP. The composition of the combined filtrate and rinse was 96.8% MSP, 1.1% DSP, and 2.1% probucol.

Ex-23B: A 1 liter round bottom flask equipped with a condenser, mechanical agitator, addition funnel, and $N_2$ bubbler was charged with 317.6 g of toluene filtrate obtained from Ex-23A. To this solution were added 75.0 g of water and 32.0 g of 1 N HCl. The mixture was stirred for 15 min and the layers were separated (pH of the aqueous layer was 8). The organic phase was washed with 101 g of water.

After charging 99.8 g of water and 100.0 g of acetone to the organic phase, the mixture was heated to 50° C. and stirred for 10 min. The layers were separated. The composition of the aqueous phase was 14.1% MSP and 84.8% DSP. The composition of the remaining organic phase was 97.4% MSP, 0.2% DSP, and 2.1% probucol. After charging 100.1 g of water and 10.0 g of acetone to the organic phase, the mixture was heated to 50° C. and stirred for 10 min. The layers were separated. The composition of the aqueous phase was 30.1% MSP and 66.5% DSP. The composition of the remaining organic phase was 97.6% MSP, 0.03% DSP and 2.2% probucol. The organic phase was allowed to cool to 25° C. and then acidified by adding 19 mL of 1 N HCl. After stirring for 15 min, the layers were separated. The organic phase was washed with 20 mL of water. The composition of the organic phase by HPLC was 97.8% MSP, 0.02% DSP, and 2.1% probucol.

The organic phase was concentrated by atmospheric distillation until about 311 mL of distillate had been collected. The distillation was continued while adding 30 mL of heptanes, and an additional 26 mL of distillate was collected. An additional 220 mL of heptanes was added while maintaining the temperature above 85° C. The mixture was allowed to cool to 25° C., nucleation was observed at about 48° C. The slurry was cooled below 3° C. over 30 min and held for 1 hour. The slurry was filtered and the wetcake was washed with 60 mL of cold heptanes. The wetcake was dried overnight in a vacuum oven at 55° C., analysis by HPLC indicated 99.9% MSP, 0.03% DSP, and 0.09% probucol.

Example 24

Ex-24: A 250 mL round bottom flask equipped with a condenser, mechanical agitator, addition funnel, and $N_2$ bubbler was charged with 26 g of MSP/DSP sodium salt wetcake (wet with water and heptanes) obtained in a manner similar to Ex-22. The wetcake composition by HPLC was 83.5% MSP, 16.2% DSP, and 0.3% probucol. The wetcake was slurried in 80.7 g of ethyl acetate and heated to 70° C. for about 30 min. The mixture was cooled to 25° C. and held for 30 min. The slurry was filtered. The wetcake was not rinsed. The composition of the wetcake by HPLC was 20.7% MSP and 79.3% DSP. The composition of the filtrate was 99.0% MSP, 0.8% DSP, and 0.1% probucol.

Example 25

Ex-25A: A sample of toluene filtrate containing MSP sodium salt (obtained in a manner similar to Ex-23A) was concentrated on a rotary evaporator, and the resulting solid was dried in a vacuum oven at 50° C. HPLC analysis of the dried MSP sodium salt indicated 98.2% MSP, 0.8% DSP, and 1.0% probucol.

Ex-25B: 0.6072 g of MSP sodium salt obtained from Ex-25A, 6.43 g of toluene, 1.81 g of water, and 0.56 g of 1 N HCl were charged to a 20 mL vial. The mixture was stirred for 20 min the layers were separated (pH of the aqueous layer was 8). The organic phase was washed with 2.03 g of water. The layers did not separate cleanly, and only 0.93 g of aqueous was collected. To the organic phase was added 1.0 g water and 1.99 g acetone. The mixture was stirred at 55° C. and then allowed to settle. The layers did not separate cleanly. HPLC analysis indicated the aqueous phase contained 44.7% MSP and 54.4% DSP.

Example 26

Ex-26: 0.5919 g of MSP sodium salt obtained from Ex-25A, 6.30 g of toluene, 1.65 g of water, and 0.66 g of 1 N HCl were added to a 20 mL vial. The mixture was stirred for 20 min the layers were separated (pH of the aqueous layer was 8). The organic phase was washed with 2.01 g of water. The layers separated cleanly. To the organic phase was added 2.05 g water and 1.99 g acetone. The mixture was stirred at 25° C. and allowed to settle. HPLC analysis indicated the aqueous phase contained 74.0% MSP and 25.0% DSP. The mixture was heated to 55° C. and allowed to settle. HPLC analysis indicated the aqueous phase contained 28.6% MSP and 70.4 DSP. Without separating the layers, an additional 1.5 g of acetone was added. Analysis of the aqueous phase at 25° C. indicated 68.8% MSP and 30.2% DSP. Analysis of the aqueous phase at 50° C. indicated 29.0% MSP and 70.0% DSP. Analysis of the organic phase indicated 98.8% MSP, 0.2% DSP, and 1.0% probucol. The layers were separated and 2.0 g of water was added to the organic phase. After stirring the mixture at ambient temperature, the organic phase contained 99.0% MSP, 0.03% DSP, and 1.0% probucol.

Example 27

Ex-27: 0.5983 g of MSP sodium salt obtained from Ex-25A, 6.37 g of toluene, 1.58 g of water, and 0.74 g of 1 N HCl were charged to a 20 mL vial. The mixture was stirred for 20 min the layers were separated (pH of the aqueous layer was 7). The organic phase was washed with 2.01 g of water. The layers separated cleanly. To the organic phase was added 2.02 g water and 2.00 g acetone. The mixture was stirred at 25° C. and allowed to settle. HPLC analysis indicated the aqueous phase contained 90.2% MSP and 8.9% DSP. The mixture was heated to 55° C. and allowed to settle. HPLC analysis indicated the aqueous phase contained 80.2% MSP and 18.7% DSP. Without separating the layers, an additional 1.5 g of acetone was added. Analysis of the aqueous phase at 25° C. indicated 75.2% MSP and 23.3% DSP.

Example 28

Ex-28: 0.5950 g of MSP sodium salt obtained from Ex-25A, 6.35 g of toluene, 1.47 g of water, and 0.85 g of 1 N HCl. The mixture was stirred for 20 min the layers were separated (pH of the aqueous layer was 6). The organic phase was washed with 2.15 g of water. The layers separated cleanly. To the organic phase was added 1.99 g water and 2.00 g acetone. The mixture was stirred at 25° C. and allowed to settle. HPLC analysis indicated the aqueous phase contained 100% MSP. The mixture was heated to 55° C. and allowed to settle. HPLC analysis indicated the aqueous phase contained 100% MSP.

Example 29

Ex-29A: A 500 mL round bottom flask was charged with 385 g of ethyl acetate filtrate containing MSP sodium salt obtained in a similar manner to Ex-23. The composition by HPLC was 97.9% MSP, 1.1% DSP, and 1.0% probucol. The filtrate contained approximately 11 wt % MSP (68.6 mmol) on a free acid basis. The filtrate was acidified by adding 17.6 mL of 4 N HCl (70.4 mmol) and 50 mL of water. The pH of the aqueous layer was 1-2. The aqueous layer was removed and the organic phase was washed with 75 mL of water. The acidified ethyl acetate organic phase was concentrated by distillation at atmospheric pressure until 284 g of distillate was collected. The distillation was continued while adding 250 mL of heptanes, and an additional 250 mL of distillate was collected. The final reactor temperature was 94° C. An additional 310 mL of heptanes was added and the mixture was cooled to 50° C. Some solids precipitated out of solution. All solids were dissolved by adding 120 mL of acetone to the mixture.

Ex-29B: A 250 mL round bottom flask was charged with 114 g of the heptanes/acetone solution obtained from Ex-29A. The solution contained 10.8 g of MSP (17.5 mmol) based on HPLC assay. While stirring the solution at 50° C., 30 g of 0.5% brine and 1.675 g (1.61 mmol) of 1 N NaOH were added. The mixture was stirred for 15 min and the layers were allowed to settle. HPLC analysis indicated the organic layer contained 99.7% MSP and 0.3% DSP, and the aqueous layer contained 33% MSP and 67% DSP. The layers separated cleanly, and the pH of the aqueous layer was 8.

After removing the aqueous layer (37.7 g), an additional 8.7 g of acetone was added to the remaining organic phase. While stirring the solution at 50° C., 29 g of 0.5% brine was added. The mixture was stirred for 15 min and the layers were allowed to settle. HPLC analysis indicated the organic layer contained 99.93% MSP and 0.07% DSP, and the aqueous layer contained 52% MSP and 48% DSP.

After removing the aqueous layer (36.2 g), an additional 8.8 g of acetone was added to the remaining organic phase. HPLC analysis of the stirred solution indicated 99.1% MSP, 0.1% DSP and 0.8% probucol. The filtrate was acidified by adding 1.0 mL of 4 N HCl (4 mmol) and 15 mL of water. The pH of the aqueous layer was 1-2. After removing the aqueous layer (19.9 g), an additional 4 g of acetone and 15.5 g of water were added to the remaining organic phase. After stirring and settling, the aqueous phase was removed (20.0 g) and an additional 4 g of acetone was added to the remaining organic phase.

Example 30

Ex-30: A 29.2 g sample of toluene filtrate containing MSP sodium salt (obtained in a manner similar to Ex-23A) was charged to a 100 mL round bottom flask. The composition of the filtrate by HPLC was 95.7% MSP, 1.6% DSP and 2.7% probucol. Based on HPLC assay, the filtrate contained 6.75 wt % MSP (3.19 mmol) on a free acid basis. The filtrate was partially acidified by adding 7.1 g water and 2.9 g (2.85 mmol) 1 N HCl. The mixture was stirred at ambient temperature for 15 min and the layers were separated. To the organic phase were added 4.4 g water and 4.4 g acetone. The mixture was stirred at 50° C. for 15 min and allowed to settle. HPLC analysis indicated the organic layer contained 96.7% MSP, 0.5% DSP, and 2.9% probucol, and the aqueous layer contained 17.9% MSP and 81.0% DSP.

Without separating the layers, an additional 4.4 g of water was added. The mixture was stirred at 50° C. and allowed to settle. HPLC analysis indicated the aqueous layer contained 17.2% MSP and 82.0% DSP. Without separating the layers, an additional 4.3 g of acetone was added. The mixture was stirred at 50° C. and allowed to settle. HPLC analysis indicated the organic layer contained 96.9% MSP, 0.2% DSP, and 2.9% probucol, and the aqueous layer contained 13.3% MSP and 85.7% DSP.

The aqueous layer was removed, and 4.4 g of water was added to the remaining organic layer. The mixture was stirred at 50° C. and allowed to settle. HPLC analysis indicated the organic layer contained 97.1% MSP, 0.01% DSP, and 2.9% probucol. Without separating the layers, an additional 2.0 g of acetone was added. The mixture was stirred at 50° and allowed to settle. HPLC analysis indicated the organic layer contained 97.1% MSP, 0.03% DSP, and 2.9% probucol.

Example 31

Ex-31: A 20.8 g sample of toluene filtrate containing MSP sodium salt (obtained in a manner similar to Ex-23A) was charged to a 100 mL round bottom flask. The composition of the filtrate by HPLC was 95.9% MSP, 1.3% DSP and 2.8% probucol. Based on HPLC assay, the filtrate contained 7.18 wt % MSP (2.42 mmol) on a free acid basis. The filtrate was partially acidified by adding 5.5 g water and 2.2 g (2.17 mmol) 1 N HCl. The mixture was stirred at ambient temperature for 5 min and the layers were allowed to settle. The pH of the aqueous layer was 0-1. Without removing the aqueous layer, the mixture was stirred for an additional 10 min and then allowed to settle. The pH of the aqueous layer was 7-8. The aqueous layer was removed and 3.3 g water and 3.3 g acetone were added to the organic layer. The mixture was stirred at 50° C. and allowed to settle. HPLC analysis indicated the organic layer contained 96.8% MSP, 0.3% DSP, and 2.8% probucol, and the aqueous layer contained 46.3% MSP and 52.8% DSP.

The aqueous layer was removed, and 3.3 g of water and 0.6 g of acetone were added to the remaining organic layer. The mixture was stirred at 50° C. and allowed to settle. HPLC analysis indicated the organic layer contained 97.1% MSP, 0.02% DSP, and 2.8% probucol.

Example 32

Ex-32: 4.534 g of toluene filtrate containing MSP sodium salt (obtained in a manner similar to Ex-23A) was charged to a 20 mL vial. The composition of the filtrate by HPLC was 99.4% MSP, 0.5% DSP and 0.1% probucol. Based on HPLC assay, the filtrate contained 16.2 wt % MSP (1.19 mmol MSP) on a free acid basis. 2.8 g of toluene, 1.11 g water, and 0.849 g (0.84 mmol) 1 N HCl were then added. The mixture was stirred for 15 min the layers were separated (pH of the aqueous layer was 8-9). To the organic phase were added 1.52 g water and 1.47 g acetone. The mixture was stirred at 25° C. and then allowed to settle. The layers separated very slowly. HPLC analysis indicated the organic layer contained 99.6% MSP, 0.3% DSP, and 0.1% probucol, and the aqueous layer contained 91.3% MSP and 8.7% DSP.

Example 33

Ex-33: 4.9589 g of toluene filtrate containing MSP sodium salt (obtained in a manner similar to Ex-23A) was charged to a 20 mL vial. The composition of the filtrate by HPLC was 99.4% MSP, 0.5% DSP and 0.1% probucol. Based on HPLC assay, the filtrate contained 16.2 wt % MSP (1.30 mmol MSP) on a free acid basis. 3.0 g of toluene, 1.00 g water, and 1.057 g (1.04 mmol) 1 N HCl were then added. The mixture was stirred for 15 min the layers were separated (pH of the aqueous layer was 8). To the organic phase were added 1.80 g water and 1.58 g acetone. The mixture was stirred at 25° C. and then allowed to settle. The layers separated very slowly. HPLC analysis indicated the organic layer contained 99.7% MSP, 0.25% DSP, and 0.1% probucol, and the aqueous layer contained 91.2% MSP and 8.8% DSP.

Example 34

Ex-34: 4.8540 g of toluene filtrate containing MSP sodium salt (obtained in a manner similar to Ex-23A) was charged to a 20 mL vial. The composition of the filtrate by HPLC was 99.4% MSP, 0.5% DSP and 0.1% probucol. Based on HPLC assay, the filtrate contained 16.2 wt % MSP (1.27 mmol MSP) on a free acid basis. 3.0 g of toluene, 1.00 g water, and 1.161 g (1.14 mmol) 1 N HCl were then added. The mixture was stirred for 15 min the layers were separated (pH of the aqueous layer was 7-8). To the organic phase was added 1.60 g water and 1.6 g acetone. The mixture was stirred at 25° C. and then allowed to settle. The layers separated cleanly. HPLC analysis indicated the organic layer contained 99.6% MSP, 0.3% DSP, and 0.1 probucol, and the aqueous layer contained 27.7% MSP and 72.3% DSP. The aqueous layer was removed and 1.6 g water and 0.28 g acetone were added to the remaining organic layer. The mixture was stirred at 25° C. and then allowed to settle. The layers separated cleanly. HPLC analysis indicated the organic layer contained 99.8% MSP, 0.1% DSP and 0.1% probucol.

Example 35

Ex-35: 4.7728 g of toluene filtrate containing MSP sodium salt (obtained in a manner similar to Ex-23A) was charged to a 20 mL vial. The composition of the filtrate by HPLC was 99.4% MSP, 0.5% DSP and 0.1% probucol. Based on HPLC assay, the filtrate contained 16.2 wt % MSP (1.25 mmol MSP) on a free acid basis. 2.9 g of toluene, 1.00 g water, and 1.196 g (1.18 mmol) 1 N HCl were then added. The mixture was stirred at 25° C. and then allowed to settle. The layers separated cleanly. HPLC analysis indicated the organic layer contained 99.4% MSP, 0.5% DSP, and 0.1% probucol, and the aqueous layer contained 93.1% MSP and 7.0% DSP.

Example 36

Ex-36: 117.7 g of a toluene/MSP free acid solution was charged to a 250 mL round bottom flask. The composition of the filtrate by HPLC was 98.1% MSP, 1.0% DSP and 1.0% probucol. Based on HPLC assay, the filtrate contained 8.2 wt % MSP (14.85 mmol MSP). To this solution were added 30 mL of water and 30 mL of acetone. The mixture was heated to 50° C. and 0.322 g (0.309 mmol) of 1 N NaOH was added. The mixture was allowed to settle and the layers were analyzed. HPLC analysis indicated the organic layer contained 99.0% MSP and 1.0% DSP, and the aqueous layer contained 95% MSP and 5% DSP. The pH of the aqueous layer was 7.2.

Without separating the layers, an additional 0.153 g (0.147 mmol, 0.456 mmol total) of 1 N NaOH was added and the mixture was stirred at 50° C. HPLC analysis indicated the organic layer contained 99.2% MSP and 0.8% DSP, and the aqueous layer contained 33% MSP and 67% DSP. The layers separated cleanly, and the pH of the aqueous layer was 7.8.

Without separating the layers, an additional 0.158 g (0.152 mmol, 0.608 mmol total) of 1 N NaOH was added and the mixture was stirred at 50° C. HPLC analysis indicated the organic layer contained 99.5% MSP and 0.5% DSP, and the aqueous layer contained 18% MSP and 82% DSP. The layers separated cleanly.

Without separating the layers, an additional 0.150 g (0.144 mmol, 0.752 mmol total) of 1 N NaOH was added and the mixture was stirred at 50° C. HPLC analysis indicated the organic layer contained 99.6% MSP and 0.4% DSP, and the aqueous layer contained 23% MSP and 77% DSP. The layers separated cleanly.

Without separating the layers, an additional 0.144 g (0.138 mmol, 0.890 mmol total) of 1 N NaOH was added and the mixture was stirred at 50° C. HPLC analysis indicated the organic layer contained 99.8% MSP and 0.2% DSP, and the aqueous layer contained 44% MSP and 56% DSP. The layers separated cleanly.

Without separating the layers, an additional 0.135 g (0.130 mmol, 1.020 mmol total) of 1 N NaOH was added and the mixture was stirred at 50° C. HPLC analysis indicated the organic layer contained 99.85% MSP and 0.15% DSP, and the aqueous layer contained 19% MSP and 81% DSP. The layers separated more slowly, with a slight white rag layer.

Without separating the layers, an additional 0.142 g (0.136 mmol, 1.156 mmol total) of 1 N NaOH was added and the mixture was stirred at 50° C. HPLC analysis indicated the organic layer contained 99.88% MSP and 0.12% DSP. The layers separated slowly, with a large white rag layer.

Without separating the layers, an additional 0.160 g (0.154 mmol, 1.310 mmol total) of 1 N NaOH was added and the mixture was stirred at 50° C. HPLC analysis indicated the organic layer contained 99.90% MSP and 0.10% DSP. The layers separated very slowly, with a large white rag layer.

Example 37

Ex-37A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-50° C. After the addition was complete, the temperature of the mixture was adjusted to 41° C. and a solution of 17.1 g (171 mmol, 1.1 eq) succinic anhydride in 173 g anhydrous THF was added over 30 min. The temperature over the addition was maintained between 40-45° C. After the addition was complete the reaction mixture was allowed to stir for 45 min. Analysis by HPLC indicated 59.4% MSP, 12.9% DSP and 25.6% probucol.

The reaction was quenched by the slow addition of 98.4 g (370 mmol) of 4 N HCl and 148.3 g of water at 40-50° C. After the quench, the reaction mixture was cooled to 20° C. and the phases were separated. The organic layer was washed with 150.0 g of 3% brine. The organic layer was washed a second time with 150.4 g of 3% brine and then treated with 39.8 mL (197.5 mmol) of 5 N NaOH and 200 mL of 10% brine. The reaction mixture was stirred at 20° C. for 45 min and the layers were separated (aqueous layer pH was 12.8).

The organic layer was concentrated to 250.0 g by distillation at 90° C. After charging 265.0 g of heptanes, the organic layer was concentrated to 206.5 g by distillation at 90° C. An additional 252.2 g of heptanes was added at 90° C. and the resulting slurry was slowly cooled to 20° C. and stirred for an additional 1 hour. The slurry was filtered and then washed with 75.0 g of heptanes. The wetcake was washed a second time with 75.0 g of heptanes. A total of 137.0 g of wetcake was collected. Analysis by HPLC indicated 81.2% MSP, 17.5% DSP and 0.7% probucol. Analysis by HPLC of the filtrate indicated 0.4% MSP and 99.4% probucol.

Ex-37B: A 1 L round bottom flask equipped with a stir bar and a $N_2$ bubbler was charged with 136.21 g of MSP/DSP sodium salt wetcake (containing water and heptanes) obtained from Ex-37A. Ethyl acetate (436.8 g) was then added and the resulting slurry was heated to 70° C. for about 1 hour. The mixture was cooled to 25° C. and held for 1.5 hours. The slurry was filtered and then rinsed with 40 mL of ethyl acetate. The composition of the wetcake by HPLC was 2.0% MSP and 98% DSP. The composition of the combined mother liquor and rinse was 98.0% MSP, 1.0% DSP, and 1.0% probucol.

The estimated weight of MSP in the filtrate was 57.73 g (91.95 mmol), assuming a 59.4% yield of MSP from probucol, up to this point in the process. The mixture was then completely acidified by adding 25.5 mL of 4 N HCl and 76.5 mL of water. After stirring for 15 min at 25° C., the aqueous phase was removed (pH of the aqueous layer was 1.23). The organic phase was washed twice with 100 mL of water (pH of the aqueous layer following second wash was 3.51). The composition of the final organic phase by HPLC was 98.0% MSP, 1% DSP, and 1% probucol.

The organic phase was charged to a 1 L round bottom flask and about ⅔ of the solvent was removed by vacuum distillation at 350 mmHg. The mixture was diluted to the original volume with fresh heptanes and the distillation was repeated. Heptanes was then added to obtain a 12 wt % MSP solution (91.95 mmol). GC analysis indicated that the ethyl acetate concentration was less than 2 wt % relative to heptanes.

The MSP free acid/heptanes solution was then transferred to a 2 L round bottom flask and the solution was heated to 50° C. To the solution were added 132.8 g of acetone, 167 g of 0.5% brine, and 5.52 mL (5.52 mmol) of 1 N NaOH. After 15 min the mixture was allowed to settle and the layers were analyzed. HPLC analysis indicated the organic layer contained 98.1% MSP, 1% DSP, and 0.9% probucol, and the aqueous layer contained 74.0% MSP and 26.0% DSP. The pH of the aqueous layer was 6.52.

Without separating the layers, an additional 2.76 mL (2.76 mmol, 8.28 mmol total) of 1 N NaOH was added while the mixture was stirred at 50° C. HPLC analysis indicated the organic layer contained 98.0% MSP, 0.8% DSP, and 0.8% probucol, and the aqueous layer contained 28% MSP and 71% DSP. The pH of the aqueous layer was 7.11.

Without separating the layers, an additional 1.84 mL (1.84 mmol, 10.12 mmol total) of 1 N NaOH was added while the mixture was stirred at 50° C. HPLC analysis indicated the organic layer contained 98.6% MSP, 0.5% DSP, and 0.8% probucol, and the aqueous layer contained 18% MSP and 81% DSP. The pH of the aqueous layer was 7.43.

Without separating the layers, an additional 1.38 mL (1.38 mmol, 11.5 mmol total) of 1 N NaOH was added while the mixture was stirred at 50° C. HPLC analysis indicated the organic layer contained 98.9% MSP, 0.3% DSP, and 0.7% probucol, and the aqueous layer contained 21% MSP and 78% DSP. The pH of the aqueous layer was 7.65. The layers were cut. To the organic solution at 50° C. were added 132.8 g of acetone and 167 g of 0.5% brine. HPLC analysis indicated the organic layer contained 99% MSP, 0.1% DSP, and 0.8% probucol, and the aqueous layer contained 63% MSP and 37% DSP. The pH of the aqueous layer was 7.68.

Without separating the layers, an additional 0.69 mL (0.69 mmol, 12.19 mmol total) of 1 N NaOH was added and the mixture was stirred at 50° C. HPLC analysis indicated the organic layer contained 99.0% MSP, 0.07% DSP, and 0.9% probucol, and the aqueous layer contained 68% MSP and 31% DSP. The pH of the aqueous layer was 7.85.

The layers were cut. The organic solution was transferred to a 1 L round bottom flask equipped with a $N_2$ bubbler and then completely acidified by adding 3.31 mL of 4 N HCl and 100 mL of water. After stirring for 15 min at 50° C., the aqueous phase was removed (pH of the aqueous layer was 1.34) and the organic layer at 50° C. was washed with 100 mL water (pH of the aqueous layer was 3.18). The organic phase was concentrated at 70° C. under 350 mmHg to ½ volume. Heptanes was then added to obtain a 12 wt % MSP solution (91.95 mmol). GC analysis indicated that the ethyl acetate and acetone concentrations were less than 1 wt % relative to heptanes.

The mixture was then cooled to 5° C. over 1 hour and held at 5° C. for 1.5 hours. The resulting suspension was filtered and rinsed twice with 75 mL of cold heptanes to yield 50.39 g (53%) MSP as a white crystalline solid (151° C. mp). HPLC analysis indicated the solid contained 99.8% MSP, 0.08% DSP, and 0.1% probucol.

Example 38

Ex-38A: A 1 L 2-neck round bottom flask equipped with an addition funnel, temperature probe and $N_2$ bubbler was charged with 80.0 g (155 mmol) probucol and 160 mL of anhydrous THF. To this solution was added 155 mL (310 mmol, 2.0 eq) of 2.0 M isopropylmagnesium chloride in THF at such a rate that the temperature was kept between 40-50° C. After the addition was complete, the temperature of the mixture was adjusted to 41° C. and a solution of 16.3 g (163 mmol, 1.05 eq) succinic anhydride in 163 g anhydrous THF was added over 30 min. The temperature over the addition was maintained between 40-45° C. After the addition was complete the reaction mixture was allowed to stir for 45 min. Analysis by HPLC indicated 59.8% MSP, 13.5% DSP and 24.2% probucol.

The reaction was quenched by the slow addition of 98.4 g (370 mmol) of 4 N HCl and 152.0 g of water at 40-50° C. After the quench, the reaction mixture was cooled to 20° C. and the phases were separated. The organic layer was washed with 152.0 g of 3% brine. The organic layer was washed a second time with 152.0 g of 3% brine and then treated with 40.4 mL (202 mmol) of 5 N NaOH and 200 mL of 10% brine. The reaction mixture was stirred at 20° C. for 45 min and the layers were separated (aqueous layer pH was 13.0).

The organic layer was concentrated to 251.0 g by distillation at 90° C. After charging 259.0 g of heptanes, the organic layer was concentrated to 253.2 g by distillation at 90° C. An additional 260.0 g of heptanes was added at 90° C. and the resulting slurry was slowly cooled to 20° C. and stirred for an additional 1 hour. The slurry was filtered and then washed with 81.0 g of heptanes. The wetcake was washed a second time with 74.2 g of heptanes. A total of 145.1 g of wetcake was collected. Analysis by HPLC indicated 80.4% MSP, 18.4% DSP and 0.6% probucol. Analysis by HPLC of the filtrate indicated 99.2% probucol.

Ex-38B: A 1 L round bottom flask equipped with a stir bar and a $N_2$ bubbler was charged with 144.88 g of MSP/DSP sodium salt wetcake (containing water and heptanes) obtained from Ex-38A. Ethyl acetate (370.69 g) was then added and the resulting slurry was heated to 70° C. for about 1 hour. The mixture was cooled to 25° C. and held for 1 hour. The slurry was filtered and then rinsed with 40 mL of ethyl acetate. The composition of the wetcake by HPLC was 0.7% MSP and 99.1% DSP. The composition of the combined mother liquor and rinse was 95.5% MSP, 3.4% DSP, and 0.6% probucol.

The estimated weight of MSP in the filtrate was 57.24 g (92.79 mmol), assuming a 59.8% yield of MSP from probucol, up to this point in the process. The mixture was then completely acidified by adding 25.5 mL of 4 N HCl and 76.6 mL of water. After stirring for 15 min at 25° C., the aqueous phase was removed (pH of the aqueous layer was 1.69). The organic phase was washed twice with 100 mL of water (pH of the aqueous layer following second wash was 3.36). The composition of the final organic phase by HPLC was 95.4% MSP, 3.5% DSP, and 0.6% probucol.

The organic phase was charged to a 1 L round bottom flask and about ⅔ of the solvent was removed by vacuum distillation at 350 mmHg. The mixture was diluted to the original volume with fresh heptanes and the distillation was repeated Heptanes was then added to obtain a 12 wt % MSP solution (92.79 mmol). GC analysis indicated that the ethyl acetate concentration was about 7 wt % relative to heptanes.

The MSP free acid/heptanes solution was then transferred to a 2 L round bottom flask and the solution was heated to 50° C. To the solution were added 132 g of acetone, 166 g of 0.5% brine, and 5.57 mL (5.57 mmol) of 1 N NaOH. After 10 min the mixture was allowed to settle and the layers were analyzed. HPLC analysis indicated the organic layer contained 96.5% MSP, 2.3% DSP, and 0.6% probucol, and the aqueous layer contained 11.1% MSP and 88.6% DSP. The pH of the aqueous layer was 7.43.

Without separating the layers, an additional 3.71 mL (3.71 mmol, 9.28 mmol total) of 1 N NaOH was added while the mixture was stirred at 50° C. HPLC analysis indicated the organic layer contained 97.9% MSP, 0.9% DSP, and 0.6% probucol, and the aqueous layer contained 14.4% MSP and 85.0% DSP. The pH of the aqueous layer was 7.67.

The layers were cut. To the organic solution at 50° C. were added 132 g of acetone and 166 g of 0.5% brine. HPLC analysis indicated the organic layer contained 98.6% MSP, 0.4% DSP, and 0.5% probucol, and the aqueous layer contained 37% MSP and 63% DSP. The pH of the aqueous layer was 7.56.

Without separating the layers, an additional 0.93 mL (0.93 mmol, 10.21 mmol total) of 1 N NaOH was added while the mixture was stirred at 50° C. HPLC analysis indicated the organic layer contained 98.6% MSP, 0.2% DSP, and 0.6% probucol, and the aqueous layer contained 41% MSP and 57% DSP. The pH of the aqueous layer was 7.90.

The layers were cut. To the organic solution at 50° C. were added 132 g of acetone and 166 g of 0.5% brine. HPLC analysis indicated the organic layer contained 98.1% MSP, 0.1% DSP, and 0.5% probucol, and the aqueous layer contained 80% MSP and 18% DSP. The pH of the aqueous layer was 7.44.

Without separating the layers, an additional 0.93 mL (0.93 mmol, 11.14 mmol total) of 1 N NaOH was added while the mixture was stirred at 50° C. HPLC analysis indicated the organic layer contained 99.0% MSP, 0.06% DSP, and 0.5% probucol, and the aqueous layer contained 83% MSP and 15% DSP. The pH of the aqueous layer was 7.74.

The layers were cut. The organic solution was transferred to a 1 L round bottom flask equipped with a $N_2$ bubbler and then completely acidified by adding 3.02 mL of 4 N HCl and 100 mL of water. After stirring for 15 min at 50° C., the aqueous phase was removed (pH of the aqueous layer was 1.33) and the organic layer at 50° C. was washed with 100 mL water (pH of the aqueous layer was 3.63). The organic phase was concentrated at 70° C. under 350 mmHg to ½ volume. Heptanes was then added to obtain a 12 wt % MSP solution (92.79 mmol). GC analysis indicated that the ethyl acetate and acetone concentrations were less than 1 wt % relative to heptanes.

The mixture was then cooled to 5° C. over 1 hour and held at 5° C. for 1.5 hours. The resulting suspension was filtered and rinsed three times with 100 mL of cold heptanes. HPLC analysis indicated the solid contained 99.2% MSP, 0.06% DSP, and 0.18% probucol. The composition of the combined mother liquor and rinses was 52% MSP and 48% probucol. The resulting solid was charged to a 1 L round bottom flask and 200 mL of heptanes was added. The reaction mixture stirred at 70° C. for 2 hours and then cooled to ambient temperature. After 2 hours the resulting suspension was filtered and rinsed with 100 mL of heptanes to yield 51.18 g (54%) MSP as a white crystalline solid (151° C. mp). HPLC analysis indicated the solid contained 99.4% MSP, 0.06% DSP, and 0.1% probucol.

Example 39

Ex-39A: A 1 L 2-neck round bottom flask equipped with an addition funnel, temperature probe and $N_2$ bubbler was charged with 80.0 g (155 mmol) probucol and 210 mL of anhydrous THF. To this solution was added 105 mL (313 mmol, 2.02 eq) of 3.0 M methylmagnesium chloride in THF at such a rate that the temperature was kept between 40-50° C. After the addition was complete, the temperature of the mixture was adjusted to 41° C. and a solution of 17.1 g (171 mmol, 1.1 eq) succinic anhydride in 173 g anhydrous THF was added over 30 min. The temperature over the addition was maintained between 40-45° C.

After the addition was complete the reaction mixture was allowed to stir for 45 min. Analysis by HPLC indicated 59.5% MSP, 21.6% DSP and 17.6% probucol. The reaction was quenched by the slow addition of 100.3 g (377 mmol) of 4 N HCl and 151.9 g of water at 40-50° C. After the quench, the reaction mixture was cooled to 20° C. and the phases were separated. The organic layer was washed with 148.5 g of 3% brine. The organic layer was washed a second time with 149.5 g of 3% brine and then treated with 48.0 mL (240 mmol) of 5 N NaOH and 200 mL of 10% brine. The reaction mixture was stirred at 20° C. for 1 hour and the layers were separated (aqueous layer pH was 13.1).

The organic layer was concentrated to 251.3 g by distillation at 90° C. After charging 251.2 g of heptanes, the organic layer was concentrated to 234.0 g by distillation at 90° C. An additional 246.7 g of heptanes was added at 90° C. and the resulting slurry was slowly cooled to 20° C. and stirred for an additional 1 hour. The slurry was filtered and then washed with 75.3 g of heptanes. The wetcake was washed a second time with 76.9 g of heptanes. A total of 173.4 g of wetcake was collected. Analysis by HPLC indicated 73.2% MSP, 26.4% DSP and 0.4% probucol. Analysis by HPLC of the filtrate indicated 0.2% MSP, 0.1% DSP and 99.5% probucol.

Ex-39B: A 1 L round bottom flask equipped with a stir bar and a $N_2$ bubbler was charged with 172.52 g of MSP/DSP sodium salt wetcake (containing water and heptanes) obtained from Ex-39A. Ethyl acetate (405.91 g) was then added and the resulting slurry was heated to 70° C. for about 1 hour. The mixture was cooled to 25° C. and held for 1 hour. The slurry was filtered and then rinsed with 40 mL of ethyl acetate. The composition of the wetcake by HPLC was 2.0% MSP and 98% DSP. The composition of the combined mother liquor and rinse was 97.2% MSP, 2.1% DSP, and 0.6% probucol.

The estimated weight of MSP in the filtrate was 56.84 g (92.14 mmol), assuming a 59.5% yield of MSP from probucol, up to this point in the process. The mixture was then completely acidified by adding 25.3 mL of 4 N HCl and 76.5 mL of water. After stirring for 15 min at 25° C., the aqueous phase was removed (pH of the aqueous layer was 1.64). The organic phase was washed twice with 100 mL of water (pH of the aqueous layer following second wash was 3.10). The composition of the final organic phase by HPLC was 96.0% MSP, 3.2% DSP, and 0.6% probucol.

The organic phase was charged to a 1 L round bottom flask and about ⅔ of the solvent was removed by vacuum distillation at 60° C. (350 mmHg). The mixture was diluted to the original volume with fresh heptanes and the distillation was repeated Heptanes was then added to obtain a 12 wt % MSP solution (92.14 mmol). GC analysis indicated that the ethyl acetate concentration was about 7 wt % relative to heptanes.

The MSP free acid/heptanes solution was then transferred to a 2 L round bottom flask and the solution was heated to 50° C. To the solution were added 131 g of acetone, 165 g of 0.5% brine, and 5.53 mL (5.53 mmol) of 1 N NaOH. After 15 min the mixture was allowed to settle and the layers were analyzed. HPLC analysis indicated the organic layer contained 2.9% MSP, 96.4% DSP, and 0.6% probucol, and the aqueous layer contained 21% MSP and 79.0% DSP. The pH of the aqueous layer was 7.08.

Without separating the layers, an additional 3.68 mL (3.68 mmol, 9.21 mmol total) of 1 N NaOH was added while the mixture was stirred at 50° C. HPLC analysis indicated the organic layer contained 98.1% MSP, 1.3% DSP, and 0.5% probucol, and the aqueous layer contained 11% MSP and 89% DSP. The pH of the aqueous layer was 7.66.

The layers were cut. To the organic solution at 50° C. were added 131 g of acetone and 165 g of 0.5% brine. HPLC analysis indicated the organic layer contained 98.6% MSP, 0.8% DSP, and 0.5% probucol, and the aqueous layer contained 29% MSP and 71% DSP. The pH of the aqueous layer was 7.40.

Without separating the layers, an additional 1.84 mL (1.84 mmol, 11.05 mmol total) of 1 N NaOH was added and the mixture was stirred at 50° C. HPLC analysis indicated the organic layer contained 99.0% MSP, 0.3% DSP, and 0.6% probucol, and the aqueous layer contained 36% MSP and 63% DSP. The pH of the aqueous layer was 7.82.

The layers were cut. To the organic solution at 50° C. were added 131 g of acetone and 165 g of 0.5% brine. HPLC analysis indicated the organic layer contained 98.2% MSP, 0.13% DSP, and 0.6% probucol, and the aqueous layer contained 77% MSP and 23% DSP. The pH of the aqueous layer was 7.53.

Without separating the layers, an additional 0.23 mL (0.23 mmol, 11.28 mmol total) of 1 N NaOH was added and the mixture was stirred at 50° C. HPLC analysis indicated the organic layer contained 99.0% MSP, 0.1% DSP, and 0.7% probucol, and the aqueous layer contained 77% MSP and 23% DSP. The pH of the aqueous layer was 7.55.

The layers were cut. The organic solution was transferred to a 1 L round bottom flask equipped with a $N_2$ bubbler and then completely acidified by adding 3.06 mL of 4 N HCl and 100 mL of water. After stirring for 15 min at 50° C., the aqueous phase was removed (pH of the aqueous layer was 1.25) and the organic layer at 50° C. was washed with 100 mL water (pH of the aqueous layer was 3.44). The organic phase was concentrated at 70° C. under 350 mmHg to ½ volume.

Heptanes was then added to obtain a 12 wt % MSP solution (92.14 mmol). GC analysis indicated that the ethyl acetate and acetone concentrations were less than 1 wt % relative to heptanes.

The mixture was then cooled to 5° C. over 1 hour and held at 5° C. for 1.5 hours. The resulting suspension was filtered and rinsed twice with 100 mL of cold heptanes to yield 50.07 g (52%) MSP as a white crystalline solid (151° C. mp). HPLC analysis indicated the solid contained 99.7% MSP, 0.1% DSP, and 0.1% probucol.

Example 40

Ex-40: A 250 mL round bottom flask equipped with a stir bar and a $N_2$ bubbler was charged with 5 g of MSP, 50 mg of DSP, 50 mg of probucol, 45 g of heptanes and 18 g of acetone. HPLC analysis of the resulting solution indicated 97.7% MSP, 0.8% DSP, and 1.5% probucol. The solution was then charged with 20 mL of 0.5% brine and heated to 50° C. To the mixture were added 0.275 mL (0.275 mmol) of 1 N NaOH. After 30 min the mixture was allowed to settle and the layers were analyzed. HPLC analysis indicated the organic layer contained 98.2% MSP, 0.2% DSP, and 1.6% probucol, and the aqueous layer contained 27% MSP and 73% DSP.

The layers were cut. To the organic solution at 50° C. were added 9 g of acetone and 20 mL of water. HPLC analysis indicated the organic layer contained 98.4% MSP and 1.6% probucol, and the aqueous layer contained 75% MSP and 25% DSP.

Example 41

Ex-41: A 250 mL round bottom flask equipped with a stir bar and a $N_2$ bubbler was charged with 5 g of MSP, 50 mg of DSP, 50 mg of probucol, 45 g of heptanes and 18 g of acetone. HPLC analysis of the resulting solution indicated 97.8% MSP, 0.8% DSP, and 1.4% probucol. The solution was then charged with 20 mL of 0.13% brine and heated to 50° C. To the mixture were added 0.275 mL (0.275 mmol) of 1 N NaOH. After 30 min the mixture was allowed to settle and the layers were analyzed. HPLC analysis indicated the organic layer contained 98.5% MSP and 1.5% probucol, and the aqueous layer contained 38% MSP and 62% DSP.

The layers were cut. To the organic solution at 50° C. were added 9 g of acetone and 20 mL of water. HPLC analysis indicated the organic layer contained 98.6% MSP, and 1.4% probucol, and the aqueous layer contained 88% MSP and 12% DSP.

Example 42

Ex-42: A 250 mL round bottom flask equipped with a stir bar and a $N_2$ bubbler was charged with 5 g of MSP, 50 mg of DSP, 50 mg of probucol, 45 g of heptanes and 18 g of acetone. HPLC analysis of the resulting solution indicated 98.4% MSP, 0.8% DSP, and 0.8% probucol. The solution was then charged with 20 mL of 0.5% brine and heated to 50° C. To the mixture were added 0.275 mL (0.275 mmol) of 1 N NaOH. After 30 min the mixture was allowed to settle and the layers were analyzed. HPLC analysis indicated the organic layer contained 98.3% MSP, 0.2% DSP, and 1.6% probucol, and the aqueous layer contained 28.5% MSP and 71.4% DSP.

The layers were cut. To the organic solution at 50° C. were added 9 g of acetone and 20 mL of 0.5% brine. HPLC analysis indicated the organic layer contained 98.8% MSP, 0.04% DSP, and 1.2% probucol, and the aqueous layer contained 88.1% MSP and 11.9% DSP. The layers were cut. To the organic solution at 50° C. were added 9 g of acetone, 20 mL of water, and 0.275 mL (0.275 mL) of 1N HCl. After 30 min the layers were cut and the organic solution at 50° C. was washed with 20 mL of water. HPLC analysis indicated the organic layer contained 98.4% MSP, 0.05% DSP, and 1.5% probucol.

Acetone was distilled from the organic phase at 75° C. The mixture was then cooled to 0° C. over 1 hour and held at 0° C. for 1 hour. The resulting suspension was filtered and rinsed with 20 g of cold heptanes to yield 4.59 g (92%) MSP as a white crystalline solid. HPLC analysis indicated the solid contained 99.8% MSP, 0.04% DSP, and 0.11% probucol.

Example 43

Ex-43: A 250 mL round bottom flask equipped with a stir bar and a $N_2$ bubbler was charged with 5 g of MSP, 50 mg of DSP, 50 mg of probucol, 40 g of heptanes, 5 g of ethyl acetate and 18 g of acetone. HPLC analysis of the resulting solution indicated 97.9% MSP, 1.1% DSP, and 0.8% probucol. The solution was then charged with 20 mL of 0.5% brine and stirred for 1 hour. HPLC analysis indicated the organic layer contained 97.7% MSP, 1.2% DSP, and 0.9% probucol, and the aqueous layer contained 100% MSP. To the mixture was added 0.275 mL (0.275 mmol) of 1 N NaOH and heated to 50° C. After 30 min the mixture was allowed to settle and the layers were analyzed. HPLC analysis indicated the organic layer contained 98.2% MSP, 0.3% DSP, and 1.3% probucol, and the aqueous layer contained 22% MSP and 78% DSP.

The layers were cut. To the organic solution at 50° C. were added 9 g of acetone and 20 mL of 0.5% brine. HPLC analysis indicated the organic layer contained 98.3% MSP, 0.10% DSP, and 1.3% probucol, and the aqueous layer contained 53% MSP and 47% DSP. The layers were cut. To the organic solution at 50° C. were added 9 g of acetone, 20 mL of water, and 0.275 mL (0.275 mL) of 1N HCl. After 30 min the layers were cut and the organic solution at 50° C. was washed with 20 mL of water. HPLC analysis indicated the organic layer contained 98.3% MSP, 0.11% DSP, and 1.4% probucol.

The layers were cut. Acetone was distilled from the organic phase at 75° C. The mixture was then cooled to 0° C. over 45 min and held at 0° C. for 1 hour. The resulting suspension was filtered and rinsed twice with 20 g of cold heptanes. HPLC analysis indicated the solid contained 99.7% MSP, 0.12% DSP, and 0.14% probucol.

Example 44

Ex-44: A 250 mL round bottom flask equipped with a stir bar and a $N_2$ bubbler was charged with 5 g of MSP, 50 mg of DSP, 50 mg of probucol, 35 g of heptanes, 10 g of ethyl acetate and 18 g of acetone. HPLC analysis of the resulting solution indicated 97.6% MSP, 0.9% DSP, and 1.2% probucol. The solution was heated to 50° C. and held for 1 hour. HPLC analysis indicated the organic layer contained 97.7% MSP, 1.2% DSP, and 0.9% probucol. The solution was then charged with 20 mL of 0.5% brine and stirred for 1 hour. HPLC analysis indicated the organic layer contained 97.5% MSP, 1.2% DSP, and 1.1% probucol, and the aqueous layer contained 100% MSP. To the mixture was added 0.275 mL (0.275 mmol) of 1 N NaOH. After 30 min the mixture was allowed to settle and the layers were analyzed. HPLC analysis indicated the organic layer contained 98.4% MSP, 0.2% DSP, and 1.3% probucol, and the aqueous layer contained 37% MSP and 63% DSP.

The layers were cut. To the organic solution at 50° C. were added 9 g of acetone and 20 mL of 0.5% brine. HPLC analysis indicated the organic layer contained 98.4% MSP, 0.1% DSP, and 1.3% probucol, and the aqueous layer contained 66% MSP and 34% DSP.

The layers were cut. To the organic solution at 50° C. were added 9 g of acetone, 20 mL of water, and 0.275 mL (0.275 mL) of 1N HCl. After 1.5 hours the layers were cut and the organic solution at 50° C. was washed with 20 mL of water. HPLC analysis indicated the organic layer contained 98.4% MSP, 0.1% DSP, and 1.3% probucol.

Example 45

Ex-45: A 250 mL round bottom flask equipped with a stir bar and a $N_2$ bubbler was charged with 5 g of MSP, 50 mg of DSP, 50 mg of probucol, 22.5 g of heptanes, 22.5 g of ethyl acetate and 18 g of acetone. HPLC analysis of the resulting solution indicated 97.2% MSP, 1.1% DSP, and 1.4% probucol. The solution was heated to 50° C. and held for 1 hour. HPLC analysis indicated the organic layer contained 97.1% MSP, 1.1% DSP, and 1.5% probucol. The solution was then charged with 20 mL of 0.5% brine and stirred for 1 hour. HPLC analysis indicated the organic layer contained 97.5% MSP, 1.2% DSP, and 1.1% probucol, and the aqueous layer contained 100% MSP. To the mixture was added 0.275 mL (0.275 mmol) of 1 N NaOH. After 30 min the mixture was allowed to settle and the layers were analyzed. HPLC analysis indicated the organic layer contained 97.9% MSP, 0.4% DSP, and 1.4% probucol, and the aqueous layer contained 16% MSP and 84% DSP.

The layers were cut. To the organic solution at 50° C. were added 9 g of acetone and 20 mL of 0.5% brine. HPLC analysis indicated the organic layer contained 98.0% MSP, 0.2% DSP, and 1.5% probucol, and the aqueous layer contained 39% MSP and 61% DSP. The layers were cut. To the organic solution at 50° C. were added 9 g of acetone, 20 mL of water, and 0.275 mL (0.275 mL) of 1N HCl. After 30 min, HPLC analysis indicated the organic layer contained 98.0% MSP, 0.2% DSP, and 1.5% probucol.

Example 46

Ex-46: A 250 mL round bottom flask equipped with a stir bar and a $N_2$ bubbler was charged with 5 g of MSP, 50 mg of DSP, 50 mg of probucol, 10 g of heptanes, 35 g of ethyl acetate and 18 g of acetone. HPLC analysis of the resulting solution indicated 97.0% MSP, 1.2% DSP, and 1.5% probucol. The solution was heated to 50° C. and held for 1 hour. HPLC analysis indicated the organic layer contained 97.0% MSP, 1.2% DSP, and 1.5% probucol. The solution was then charged with 20 mL of 0.5% brine and stirred for 1 hour. HPLC analysis indicated the organic layer contained 97.0% MSP, 1.2% DSP, and 1.5% probucol, and the aqueous layer contained 100% MSP. To the mixture was added 0.275 mL (0.275 mmol) of 1 N NaOH. After 30 min the mixture was allowed to settle and the layers were analyzed. HPLC analysis indicated the organic layer contained 97.4% MSP, 0.8% DSP, and 1.5% probucol, and the aqueous layer contained 14% MSP and 86% DSP.

The layers were cut. To the organic solution at 50° C. were added 9 g of acetone and 20 mL of 0.5% brine. HPLC analysis indicated the organic layer contained 97.6% MSP, 0.6% DSP, and 1.5% probucol, and the aqueous layer contained 32% MSP and 68% DSP. The layers were cut. To the organic solution at 50° C. were added 9 g of acetone, 20 mL of water, and 0.275 mL (0.275 mL) of 1N HCl. After 30 min, HPLC analysis indicated the organic layer contained 97.6% MSP, 0.6% DSP, and 1.5% probucol.

Example 47

Ex-47A: A 500 mL 2-neck round bottom flask equipped with an addition funnel, temperature probe and $N_2$ bubbler was charged with 40.0 g (77.4 mmol) probucol and 80 mL of anhydrous THF. To this solution was added 78.8 mL (156 mmol, 2.02 eq) of 2.0 M benzylmagnesium chloride in THF at such a rate that the temperature was kept between 40-50° C. After the addition was complete, the temperature of the mixture was adjusted to 41° C. and a solution of 8.5 g (85.1 mmol, 1.1 eq) succinic anhydride in 85.9 g anhydrous THF was added over 30 min. The temperature over the addition was maintained between 40-45° C. After the addition was complete the reaction mixture was allowed to stir for 37 min. Analysis by HPLC indicated 58.4% MSP, 11.8% DSP and 27.5% probucol.

The reaction was quenched by the slow addition of 50 g (184 mmol) of 4 N HCl and 74.2 g of water at 40-50° C. After the quench, the reaction mixture was cooled to 20° C. and the phases were separated. The organic layer was washed with 80 g of 3% brine. The organic layer was washed a second time with 81.7 g of 3% brine and then treated with 19.0 mL (95.1 mmol) of 5 N NaOH and 100 mL of 10% brine. The reaction mixture was stirred at 20° C. for 30 min and the layers were separated (aqueous layer pH was 12.4).

The organic layer was concentrated to 110.3 g by distillation at 90° C. After charging 115.8 g of heptanes, the organic layer was concentrated to 99.5 g by distillation at 90° C. An additional 129.0 g of heptanes was added at 90° C. and the resulting slurry was slowly cooled to 20° C. and stirred for an additional 1 hour. The slurry was filtered and then washed with 50 g of heptanes. The wetcake was washed a second time with 50 g of heptanes. A total of 57.4 g of wetcake was collected. Analysis by HPLC indicated 81.9% MSP, 16.3% DSP and 0.7% probucol. Analysis by HPLC of the filtrate indicated 0.1% MSP and 99.7% probucol.

Ex-47B: A 1 L round bottom flask equipped with a stir bar and a $N_2$ bubbler was charged with 57.4 g of MSP/DSP sodium salt wetcake (containing water and heptanes) obtained from Ex-47A. Ethyl acetate (206.6 g) was then added and the resulting slurry was heated to 70° C. for about 1 hour. The mixture was cooled to 25° C. and held for 1 hour. The slurry was filtered and then rinsed with 30 mL of ethyl acetate. The composition of the wetcake by HPLC was 5.8% MSP and 94.2% DSP. The composition of the combined mother liquor and rinse was 97.7% MSP, 1.0% DSP, and 1.3% probucol.

The estimated weight of MSP in the filtrate was 28.0 g (45.1 mmol), assuming a 58.4% yield of MSP from probucol, up to this point in the process. The mixture was then completely acidified by adding 13.48 g of 4 N HCl and 42 mL of water. After stirring for 15 min at 25° C., the aqueous phase was removed (pH of the aqueous layer was between 1 and 2). The organic phase was washed with 53 mL of water (pH of the aqueous layer was between 2 and 3). Analysis by HPLC of the final organic phase indicated 97.0% MSP, 1.0% DSP, and 1.8% probucol.

Ex-47C, 81.88 g of the organic solution (containing 9.24 g MSP) obtained from Ex-47B was charged to a 250 mL round bottom flask and about ⅔ of the solvent was removed by vacuum distillation at 60° C. (350 mmHg). The mixture was diluted to the original volume with fresh heptanes and the distillation was repeated Heptanes was then added to obtain a 12 wt % MSP solution (15.0 mmol). GC analysis indicated that the ethyl acetate concentration was about 6 wt % relative to heptanes.

The MSP free acid/heptanes solution was then heated to 50° C. To the solution were added 26.4 g of acetone, 33 g of 0.5% brine, and 0.62 mL (0.62 mmol) of 1 N NaOH. After 15 min the mixture was allowed to settle and the layers were analyzed. HPLC analysis indicated the organic layer contained 97.0% MSP, 0.99% DSP, and 1.8% probucol, and the aqueous layer contained 73% MSP and 27% DSP. The pH of the aqueous layer was 6.14.

Without separating the layers, an additional 0.413 mL (0.413 mmol, 1.03 mmol total) of 1 N NaOH was added while the mixture was stirred at 50° C. HPLC analysis indicated the organic layer contained 97.1% MSP, 0.90% DSP, and 1.8% probucol, and the aqueous layer contained 51% MSP and 42% DSP. The pH of the aqueous layer was 6.82.

Without separating the layers, an additional 0.62 mL (0.62 mmol, 1.65 mmol total) of 1 N NaOH was added while the mixture was stirred at 50° C. HPLC analysis indicated the organic layer contained 97.9% MSP, 0.31% DSP, and 1.8% probucol, and the aqueous layer contained 24.5% MSP and 67.6% DSP. The pH of the aqueous layer was 7.58.

The layers were cut. To the organic solution at 50° C. were added 13.2 g of acetone and 33 g of 0.5% brine. HPLC analysis indicated the organic layer contained 98.0% MSP, 0.2% DSP, and 1.8% probucol, and the aqueous layer contained 44% MSP, 51% DSP, and 0% probucol. The pH of the aqueous layer was 7.32.

Without separating the layers, an additional 0.10 mL (0.10 mmol, 1.75 mmol total) of 1 N NaOH was added and the mixture was stirred at 50° C. HPLC analysis indicated the organic layer contained 98.1% MSP, 0.14% DSP, and 1.81% probucol, and the aqueous layer contained 39% MSP, 56% DSP, and 0% probucol. The pH of the aqueous layer was 7.61.

Without separating the layers, an additional 0.413 mL (0.413 mmol, 2.16 mmol total) of 1 N NaOH was added and the mixture was stirred at 50° C. HPLC analysis indicated the organic layer contained 98.6% MSP, 0.05% DSP, and 1.36% probucol, and the aqueous layer contained 39% MSP and 56% DSP.

Example 48

Ex-48: 86.91 g of the organic solution (containing 9.8 g MSP) obtained from Ex-47B was washed with 19 g of water. The layers were cut. The organic phase was then charged to a 250 mL round bottom flask and about ⅔ of the solvent was removed by vacuum distillation at 60° C. (350 mmHg). The mixture was diluted to the original volume with fresh heptanes and the distillation was repeated Heptanes was then added to obtain a 12 wt % MSP solution (15.91 mmol). GC analysis indicated that the ethyl acetate concentration was about 5 wt % relative to heptanes.

The MSP free acid/heptanes solution was then heated to 50° C. To the solution were added 28 g of acetone, 35 g of 0.5% brine, and 0.62 mL (0.62 mmol) of 1 N NaOH. After 15 min the mixture was allowed to settle and the layers were analyzed. HPLC analysis indicated the organic layer contained 97.2% MSP, 0.99% DSP, and 1.6% probucol, and the aqueous layer contained 65% MSP and 35% DSP. The pH of the aqueous layer was 6.14. Without separating the layers, an additional 0.62 mL (0.62 mmol, 1.24 mmol total) of 1 N NaOH was added while the mixture was stirred at 50° C. HPLC analysis indicated the organic layer contained 97.7% MSP, 0.79% DSP, and 1.40% probucol. The pH of the aqueous layer was 7.04.

Without separating the layers, an additional 0.207 mL (0.207 mmol, 1.45 mmol total) of 1 N NaOH was added while the mixture was stirred at 50° C. HPLC analysis indicated the organic layer contained 97.5% MSP, 0.52% DSP, and 1.85% probucol, and the aqueous layer contained 17.2% MSP and 72.9% DSP. The pH of the aqueous layer was 7.34.

Without separating the layers, an additional 0.413 mL (0.413 mmol, 1.86 mmol total) of 1 N NaOH was added while the mixture was stirred at 50° C. HPLC analysis indicated the organic layer contained 98.1% MSP, 0.18% DSP, and 1.66% probucol, and the aqueous layer contained 29.70% MSP and 63.18% DSP. The pH of the aqueous layer was 7.73.

The layers were cut. To the organic solution at 50° C. were added 14 g of acetone and 35 g of 0.5% brine. HPLC analysis indicated the organic layer contained 98.0% MSP, 0.07% DSP, and 1.87% probucol, and the aqueous layer contained 55% MSP and 41% DSP. The pH of the aqueous layer was 7.69.

Example 49

Ex-49: 77.75 g of the organic solution (containing 8.78 g MSP) obtained from Ex-47B was washed with 17 g of 3% brine. The layers were cut. The organic solution was then charged to a 250 mL round bottom flask and about ⅔ of the solvent was removed by vacuum distillation at 60° C. (350 mmHg). The mixture was diluted to the original volume with fresh heptanes and the distillation was repeated Heptanes was then added to obtain a 12 wt % MSP solution (14.27 mmol). GC analysis indicated that the ethyl acetate concentration was about 3 wt % relative to heptanes.

The MSP free acid/heptanes solution was then heated to 50° C. To the solution were added 25 g of acetone, 31.4 g of 0.5% brine, and 0.62 mL (0.62 mmol) of 1 N NaOH. After 15 min the mixture was allowed to settle and the layers were analyzed. HPLC analysis indicated the organic layer contained 97.1% MSP, 0.98% DSP, and 1.76% probucol, and the aqueous layer contained 83% MSP and 17% DSP. The pH of the aqueous layer was 6.27.

Without separating the layers, an additional 0.62 mL (0.62 mmol, 1.24 mmol total) of 1 N NaOH was added while the mixture was stirred at 50° C. HPLC analysis indicated the organic layer contained 97.7% MSP, 0.51% DSP, and 1.67% probucol, and the aqueous layer contained 30% MSP and 62% DSP. The pH of the aqueous layer was 7.25.

Without separating the layers, an additional 0.413 mL (0.413 mmol, 1.65 mmol total) of 1 N NaOH was added while the mixture was stirred at 50° C. HPLC analysis indicated the organic layer contained 98.1% MSP, 0.15% DSP, and 1.72% probucol, and the aqueous layer contained 32% MSP and 60% DSP. The pH of the aqueous layer was 7.69.

Without separating the layers, an additional 0.413 mL (0.413 mmol, 2.06 mmol total) of 1 N NaOH was added while the mixture was stirred at 50° C. HPLC analysis indicated the organic layer contained 98.0% MSP, 0.10% DSP, and 1.86% probucol, and the aqueous layer contained 59% MSP and 36% DSP. The pH of the aqueous layer was 7.89.

Without separating the layers, an additional 0.413 mL (0.413 mmol, 2.48 mmol total) of 1 N NaOH was added while the mixture was stirred at 50° C. HPLC analysis indicated the organic layer contained 98.1% MSP, 0.08% DSP, and 1.77% probucol, and the aqueous layer contained 82% MSP and 16% DSP. The pH of the aqueous layer was 7.93.

Example 50

Ex-50A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 175 g anhydrous THF was added over 30 min. The temperature over the addition was maintained between 40-45° C. After the addition was complete the reaction mixture was allowed to stir for 45 min. Analysis by HPLC indicated 58.4% MSP, 13.8% DSP and 27.1% probucol.

The reaction was quenched by the slow addition of 98.2 g (370 mmol) of 4 N HCl and 148.2 g of water at 40-50° C. After the quench, the reaction mixture was cooled to 20° C. and the phases were separated. The organic layer was washed with 160 g of water. The organic layer was washed a second time with 160 g of water. Analysis by HPLC of the organic phase (420.3 g) indicated 57.4% MSP, 12.4% DSP, and 27.7% probucol.

Ex-50B: 119.72 g of the organic solution obtained from Ex-50A was charged to a 250 mL round bottom flask and then treated with 8.55 g (36.24 mmol) of 5 N NaOH and 45 mL of 10% brine. HPLC analysis indicated the organic layer contained 58% MSP, 11.9% DSP, and 27% probucol, and the aqueous layer contained 15% MSP and 82% DSP. The pH of the aqueous layer was 7.69

Example 51

Ex-51: 110.81 g of the organic solution obtained from Ex-50A was charged to a 250 mL round bottom flask and then treated with 11.9 g (50.32 mmol) of 5 N NaOH and 45 mL of 10% brine. HPLC analysis indicated the organic layer contained 58.5% MSP, 12.2% DSP, and 28.2% probucol, and the aqueous layer contained 39.4% MSP, 44.0% DSP, and 14.7% probucol. The pH of the aqueous layer was 12.93.

Example 52

Ex-52: 112.03 g of the organic solution obtained from Ex-50A was charged to a 250 mL round bottom flask and then treated with 16.0 g (67.83 mmol) of 5 N NaOH and 45 mL of 10% brine. HPLC analysis indicated the organic layer contained 58.5% MSP, 12.2% DSP, and 28.2% probucol, and the aqueous layer contained 57.5% MSP, 16.4% DSP, and 24.5% probucol. The pH of the aqueous layer was 13.35.

Example 53

Ex-53: 63.6 g of the organic solution obtained from Ex-50A was concentrated via distillation at 70° C. to remove the tetrahydrofuran and then diluted with heptanes to the original volume. The resulting solution was again concentrated to ⅓ volume at 70° C. and diluted to the original volume with heptanes. The resulting slurry was cooled to 50° C. and filtered. Analysis by HPLC of the wetcake indicated 42% MSP, 38% DSP, and 17% probucol, and the filtrate contained 64% MSP, 1.5% DSP, and 31% probucol. The wetcake was suspended in fresh heptanes at 50° C. for 1 hour and filtered. Analysis by HPLC of the wetcake indicated 22% MSP, 71% DSP, and 6% probucol, and the filtrate contained 65% MSP, 0.4% DSP, and 33% probucol. The wetcake was suspended in fresh heptanes at 50° C. for 1 hour and filtered. Analysis by HPLC of the wetcake indicated 16% MSP, and 84% DSP. The filtrates were combined and cooled to 5° C. with stirring. After 1 hour the suspension was filtered. Analysis by HPLC of the wetcake indicated 86.0% MSP, 1.8% DSP, and 9.3% probucol, and the filtrate contained 16% MSP, 0.4% DSP, and 84% probucol.

Example 54

Ex-54: ⅓ of the organic solution obtained from Ex-50B was concentrated by distillation at 90° C. and then diluted to the original volume with toluene. After aging at 50° C. for 1 hour the resulting slurry was filtered. Analysis of the wetcake by HPLC indicated 1.5% MSP, 98.3% DSP and 0.16% probucol. Analysis by HPLC of the filtrate indicated 65.5% MSP, 1.7% DSP and 31.4% probucol.

Example 55

Ex-55: ⅓ of the organic solution obtained from Ex-51 was concentrated by distillation at 90° C. and then diluted to the original volume with toluene. After aging at 50° C. for 1 hour the resulting slurry was filtered. Analysis of the wetcake by HPLC indicated 2.7% MSP, 97.0% DSP and 0.4% probucol. Analysis by HPLC of the filtrate indicated 64.6% MSP, 3.3% DSP and 31.8% probucol.

Example 56

Ex-56: ⅓ of the organic solution obtained from Ex-52 was concentrated by distillation at 90° C. and then diluted to the original volume with toluene. After aging at 50° C. for 1 hour the resulting slurry was filtered. Analysis of the wetcake by HPLC indicated 1.4% MSP and 98.6% DSP. Analysis by HPLC of the filtrate indicated 66.2% MSP, 1.4% DSP and 32.2% probucol.

Example 57

Ex-57A: ⅓ of the organic solution obtained from Ex-50B was concentrated by distillation at 90° C. and then diluted to the original volume with heptane. After aging at 0° C. for 1 hour the resulting slurry was filtered. Analysis of the wetcake by HPLC indicated 76% MSP, 19.8% DSP and 1.5% probucol. Analysis by HPLC of the filtrate indicated 32.0% MSP, 0.13% DSP and 67.6% probucol.

Ex-57B: 2 g of the wetcake obtained from Ex-57A was added to 10 mL toluene and the resulting suspension was heated to 50° C. After 1 hour the suspension was filtered. Analysis of the wetcake by HPLC indicated 17% MSP, 82% DSP, and 0.3% probucol. Analysis by HPLC of the filtrate indicated 93% MSP, 2.4% DSP, and 2.1% probucol.

Example 58

Ex-58A: ⅓ of the organic solution obtained from Ex-51 was concentrated by distillation at 90° C. and then diluted to the original volume with heptane. After aging at 0° C. for 1 hour the resulting slurry was filtered. Analysis of the wetcake by HPLC indicated 82.0% MSP, 17.0% DSP and 0.5% probucol. Analysis by HPLC of the filtrate indicated 0.16% MSP and 99.7% probucol.

Ex-58B: 2 g of the wetcake obtained from Ex-58A was added to 10 mL toluene and the resulting suspension was heated to 50° C. After 1 hour the suspension was filtered. Analysis of the wetcake by HPLC indicated 33.3% MSP, 66.6% DSP, and 0.1% probucol. Analysis by HPLC of the filtrate indicated 97.7% MSP, 1.6% DSP, and 0.5% probucol.

Example 59

Ex-59A: ⅓ of the organic solution obtained from Ex-52 was concentrated by distillation at 90° C. and then diluted to the original volume with heptane. After aging at 0° C. for 1 hour the resulting slurry was filtered. Analysis of the wetcake by HPLC indicated 83.0% MSP, 16.9% DSP, and 0.14% probucol. Analysis by HPLC of the filtrate indicated 99.7% probucol.

Ex-59B: 2 g of the wetcake obtained from Ex-59A was added to 10 mL toluene and the resulting suspension was heated to 50° C. After 1 hour the suspension was filtered. Analysis of the wetcake by HPLC indicated 12.5% MSP and 87.5% DSP. Analysis by HPLC of the filtrate indicated 96.7% MSP, 2.9% DSP, and 0.3% probucol.

Example 60

Ex-60: ⅓ of the organic solution obtained from Ex-50B was concentrated by distillation at 90° C. and then diluted to the original volume with isopropyl acetate. After aging at 25° C. for 1 hour the resulting slurry was filtered. Analysis of the wetcake by HPLC indicated 0.8% MSP, 98.9% DSP and 0.2% probucol. Analysis by HPLC of the filtrate indicated 66.0% MSP, 1.3% DSP and 32.0% probucol.

Example 61

Ex-61: ⅓ of the organic solution obtained from Ex-51 was concentrated by distillation at 90° C. and then diluted to the original volume with isopropyl acetate. After aging at 25° C. for 1 hour the resulting slurry was filtered. Analysis of the wetcake by HPLC indicated 0.7% MSP, 99.0% DSP and 0.2% probucol. Analysis by HPLC of the filtrate indicated 66.5% MSP, 0.5% DSP and 32.7% probucol.

Example 62

Ex-62: ⅓ of the organic solution obtained from Ex-52 was concentrated by distillation at 90° C. and then diluted to the original volume with isopropyl acetate. After aging at 25° C. for 1 hour the resulting slurry was filtered. Analysis of the wetcake by HPLC indicated 2.7% MSP, 96.8% DSP, and 0.4% probucol. Analysis by HPLC of the filtrate indicated 66.8% MSP, 0.4% DSP, and 32.6% probucol.

Example 63

Ex-63: 2 g of the wetcake obtained from Ex-57A was added to 10 mL isopropyl acetate and the resulting suspension was heated to 80° C. After 1 hour the suspension was cooled to 25° C., aged 1 hour and filtered. Analysis of the wetcake by HPLC indicated 18.8% MSP, 80.7% DSP, and 0.5% probucol. Analysis by HPLC of the filtrate indicated 94% MSP, 1.0% DSP, and 2.9% probucol.

Example 64

Ex-64: 2 g of the wetcake obtained from Ex-58A was added to 10 mL isopropyl acetate and the resulting suspension was heated to 80° C. After 1 hour the suspension was cooled to 25° C., aged 1 hour and filtered. Analysis of the wetcake by HPLC indicated 3.8% MSP and 96.2% DSP. Analysis by HPLC of the filtrate indicated 98.0% MSP, 0.5% DSP, and 0.5% probucol.

Example 65

Ex-65: 2 g of the wetcake obtained from Ex-59A was added to 10 mL isopropyl acetate and the resulting suspension was heated to 80° C. After 1 hour the suspension was cooled to 25° C., aged 1 hour and filtered. Analysis of the wetcake by HPLC indicated 5.8% MSP and 94.1% DSP. Analysis by HPLC of the filtrate indicated 99.0% MSP, 0.6% DSP, and 0.2% probucol.

Example 66

Ex-66A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 181 g anhydrous THF was added over 30 min. The temperature over the addition was maintained between 40-45° C. After the addition was complete the reaction mixture was allowed to stir for 20 min. Analysis by HPLC indicated 57.8% MSP, 11.3% DSP and 28.6% probucol.

The reaction was quenched by the slow addition of 98.2 g (370 mmol) of 4 N HCl and 148.2 g of water at 40-50° C. After the quench, the reaction mixture was cooled to 20° C. and the phases were separated. The organic layer was washed with 160 g of water. The organic layer was washed a second time with 160 g of water. Analysis by HPLC of the organic phase (423.79 g) indicated 57.7% MSP, 11.4% DSP, and 28.6% probucol.

Ex-66B: 197.97 g of the organic solution obtained from Ex-66A was charged to a 500 mL round bottom flask and then treated with 16.6 g (70.12 mmol) of 5 N NaOH and 100 mL of 10% brine. HPLC analysis indicated the organic layer contained 58.0% MSP, 11.2% DSP, and 28.6% probucol, and the aqueous layer contained 22.7% MSP, 67.6% DSP, and 7.6% probucol. The pH of the aqueous layer was 7.86.

Ex-66C: ½ of the organic phase obtained from Ex-66B was charged to a 500 mL round bottom flask and about ⅔ of the solvent was removed by vacuum distillation at 90° C. The mixture was diluted to the original volume with fresh isopropyl acetate and the distillation was repeated. Isopropyl acetate was added and the mixture was then cooled to 25° C. and held for 1 hour, and then filtered. HPLC analysis indicated the wetcake contained 9.3% MSP, 89.4% DSP, and 1.1% probucol, and the mother liquor contained 64.7% MSP and 0.55% DSP, and 33.8% probucol.

Example 67

Ex-67A: ½ of the organic phase obtained from Ex-66B was charged to a 500 mL round bottom flask and about ⅔ of the solvent was removed by vacuum distillation at 90° C. The mixture was diluted to the original volume with fresh heptanes and the distillation was repeated. Heptanes was added and the mixture was then cooled to 5° C. over 1 hour and held at 5° C. for 1 hour, and then filtered. HPLC analysis indicated the wetcake contained 76% MSP, 19.8% DSP, and 1.5% probucol, and the mother liquor contained 6.9% MSP and 92.7% probucol.

Ex-67B: The wetcake obtained from Ex-67A was heated in isopropyl acetate at 80° C. for 1 hour. After cooling to 25° C. and aging 2 hours the suspension was filtered. HPLC analysis indicated the wetcake contained 28% MSP, 71% DSP, and 0.8% probucol, and the mother liquor contained 96% MSP and 0.7% DSP, and 3% probucol.

Example 68

Ex-68: 216.18 g of the organic solution obtained from Ex-66A was charged to a 500 mL round bottom flask and then treated with 37.64 g (159.51 mmol) of 5 N NaOH and 100 mL of 10% brine. HPLC analysis indicated the organic layer contained 58.7% MSP, 11.5% DSP, and 28.5% probucol, and the aqueous layer contained 60.9% MSP and 2.2% DSP, and 5.7% probucol. The pH of the aqueous layer was 13.69.

Example 69

Ex-69A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 181 g anhydrous THF was added over 30 min. The temperature over the addition was maintained between 40-45° C. After the addition was complete the reaction mixture was allowed to stir for 1 hour. Analysis by HPLC indicated 56.6% MSP, 10.7% DSP and 30.1% probucol.

The reaction was quenched by the slow addition of 98.1 g (370 mmol) of 4 N HCl and 148.3 g of water at 40-50° C. After the quench, the reaction mixture was cooled to 20° C. and the phases were separated. The organic layer was washed with 160 g of water. The organic layer was washed a second time with 160 g of water. Analysis by HPLC of the organic phase (431.25 g) indicated 56.6% MSP, 10.7% DSP, and 30.0% probucol.

Ex-69B: 215.33 g of the organic solution obtained from Ex-69A was charged to a 500 mL round bottom flask and then treated with 24.4 g (103.69 mmol) of 5 N NaOH and 100 mL of 10% brine. HPLC analysis indicated the organic layer contained 56.8% MSP, 10.6% DSP, and 31.1% probucol, and the aqueous layer contained 30.6% MSP and 65.0% DSP. The pH of the aqueous layer was 12.95.

The layers were cut and the organic phase was charged to a 500 mL round bottom flask and about ⅔ of the solvent was removed by vacuum distillation at 90° C. The mixture was diluted to the original volume with fresh heptanes and the distillation was repeated. Heptanes was added to a final weight of 310 g. After slowly cooling to ambient temperature and then 5° C. the resulting precipitant was aged for 1 hour and filtered. HPLC analysis indicated the wetcake contained 83.7% MSP, 15.5% DSP, and 0.6% probucol, and the filtrate contained 0.1% MSP and 99.6% probucol.

Example 70

Ex-70A: 215.92 g of the organic solution obtained from Ex-69A was charged to a 500 mL round bottom flask and then treated with 21 g (89.13 mmol) of 5 N NaOH and 100 mL of 10% brine. HPLC analysis indicated the organic layer contained 56.8% MSP, 10.6% DSP, and 30.6% probucol, and the aqueous layer contained 23.4% MSP and 74.1% DSP. The pH of the aqueous layer was 11.67.

The layers were cut and the organic phase was charged to a 500 mL round bottom flask and about ⅔ of the solvent was removed by vacuum distillation at 90° C. The mixture was diluted to the original volume with fresh heptanes and the distillation was repeated. Heptanes was added and the mixture was then cooled to 5° C. over 1 hour and held at 5° C. for 2 hours. The resulting suspension was filtered and rinsed with 200 mL of heptanes to yield 60 g of MSP/DSP salt wetcake. HPLC analysis indicated the solid contained 81.4% MSP, 14.9% DSP, and 2.9% probucol, and the filtrate contained 0.2% MSP and 99.6% probucol.

Ex-70B: 44.77 g of the MSP/DSP wetcake (containing heptanes and water) obtained from Ex-70A and 225 mL of ethyl acetate were charged to 500 mL round bottom flask and heated to 70° C. and held for 30 min. The mixture stirred to 25° C. and was held for 1.75 hours and then filtered. HPLC analysis indicated the wetcake contained 15.8% MSP, 83.9% DSP, and 0.2% probucol, and the filtrate contained 97.7% MSP, 0.6% DSP, and 1.3% probucol.

Example 71

Ex-71: A 250 mL 2-neck round bottom flask equipped with an addition funnel, temperature probe and $N_2$ bubbler was charged with 20.0 g (38.7 mmol) probucol and 50 mL of anhydrous THF. To this solution was added 25.8 mL (77.4 mmol, 2.0 eq) of 3.0 M methylmagnesium chloride in THF at such a rate that the temperature was kept between 40-50° C. After the addition was complete, the temperature of the mixture was adjusted to 41° C. and a solution of 3.68 g (36.8 mmol, 0.95 eq) succinic anhydride in 37.2 g anhydrous THF was added over 30 min. The temperature during the addition was maintained between 40-45° C. After the addition was complete the reaction mixture was allowed to stir for 60 min at 45° C. HPLC analysis indicated 57.7% MSP, 15.1% DSP and 26.1% probucol.

The reaction was quenched by the slow addition of 24.6 g (98.4 mmol) of 4 N HCl and 43.9 g of water at 40-50° C. After the quench, the reaction mixture was cooled to 20° C. and the phases were separated. The organic layer was washed with 40.5 g of 3% brine. The organic layer was washed a second time with 39.7 g of 3% brine. The organic layer was diluted with 82 g of EtOAc and concentrated under reduced pressure at 90° C. until about ½ of the solvent was removed. An additional 106 g of EtOAc was added and the organic solution was concentrated under reduced pressure at 90° C. until about ½ of the solvent was removed. The mixture was diluted with 80 g heptanes and the distillation was repeated Heptanes was added to obtain a 12 wt % MSP solution (22.4 mmol).

The heptanes solution was transferred to a 500 mL round bottom flask and heated to 50° C. The solution was treated with 46.1 g of acetone, 41.1 g of 0.5% brine, and 2.50 mL (12.5 mmol) of 5 N NaOH. After stirring for 15 min, the mixture was allowed to settle and the layers were analyzed. HPLC analysis indicated the organic layer contained 77.1% MSP, 2.1% DSP, and 20.6% probucol, and the aqueous layer contained 21.4% MSP and 73.5% DSP. The layers were cut. The organic solution was treated with were added 35.1 g of acetone, 41.5 g of 0.5% brine, and 0.22 mL (1.1 mmol, 13.6 mmol total) of 5 N NaOH. After stirring for 15 min at 50° C., the mixture was allowed to settle and the layers were analyzed. HPLC analysis indicated the organic layer contained 67.4% MSP, 0.15% DSP, and 32.3% probucol, and the aqueous layer contained 37.7% MSP and 60.6% DSP.

The layers were cut. The organic solution was treated with 35.4 g of acetone, 41.1 g of 0.5% brine, and 0.22 mL (0.22 mmol, 13.82 mmol total) of 1 N NaOH. After stirring for 15 min at 50° C., the mixture was allowed to settle and the layers were analyzed. HPLC analysis indicated the organic layer contained 67.1% MSP, 0.0% DSP, and 32.8% probucol, and the aqueous layer contained 83.0% MSP and 9.8% DSP.

The layers were cut. The organic solution was transferred to a 500 mL round bottom flask and acidified by adding 3.4 mL of 4 N HCl (13.7 mmol) and 25.4 mL of water. After stirring for 15 min at 50° C., the layers were separated and the organic layer was concentrated at 70° C. under 350 mmHg to ½ volume. Heptanes was added to obtain an 8 wt % MSP solution. The mixture was then cooled to ambient temperature and stirred overnight. The resulting suspension was filtered to yield 12.2 g MSP. HPLC analysis indicated the solid contained 97.3% MSP, 0.03% DSP, and 2.6% probucol.

Example 72

Ex-72: A 250 mL 2-neck round bottom flask equipped with an addition funnel, temperature probe and $N_2$ bubbler was charged with 20.0 g (38.7 mmol) probucol and 50 mL of anhydrous THF. To this solution was added 25.8 mL (77.4 mmol, 2.0 eq) of 3.0 M methylmagnesium chloride in THF at such a rate that the temperature was kept between 40-50° C. After the addition was complete, the temperature of the mixture was adjusted to 41° C. and a solution of 3.68 g (36.8 mmol, 0.95 eq) succinic anhydride in 37.2 g anhydrous THF was added over 30 min. The temperature over the addition was maintained between 40-45° C. After the addition was complete the reaction mixture was allowed to stir for 45 min. Analysis by HPLC indicated 54.8% MSP, 12.9% DSP and 31.2% probucol.

The reaction was quenched by the slow addition of 24.6 g (98.4 mmol) of 4 N HCl and 39.6 g of water at 40-50° C. After the quench, the reaction mixture was cooled to 20° C. and the phases were separated. The organic layer was washed with 41.5 g of 3% brine. The organic layer was washed a second time with 38.7 g of 3% brine. The organic layer was concentrated until about ⅔ of the solvent was removed by vacuum distillation at 90° C. The mixture was diluted with 75 g of EtOAc and 50% of the solvent was removed under reduced pressure at 90° C. An additional 75 g of EtOAc was charged and the organic solution was concentrated under reduced pressure at 90° C. The mixture was diluted to the original volume with fresh heptanes and the distillation was repeated Heptanes was then added to obtain a 12 wt % MSP solution (21.1 mmol).

The heptanes solution was transferred to 500 mL round bottom flask and heated to 50° C. The solution was treated with 35.6 g of acetone, 40.6 g of 0.5% brine, and 2.33 mL (11.7 mmol) of 5 N NaOH. After stirring for 15 min at 50° C., the mixture was allowed to settle and the layers were analyzed. HPLC analysis indicated the organic layer contained 63.1% MSP, 3.3% DSP, and 33.4% probucol, and the aqueous layer contained 17.8% MSP and 76.4% DSP.

The layers were cut. The organic solution was treated with 20.3 g of acetone, 41.3 g of 0.5% brine, and 0.21 mL (1.05 mmol, 12.75 mmol total) of 5 N NaOH. After stirring for 15 min at 50° C., the mixture was allowed to settle and the layers were analyzed. HPLC analysis indicated the organic layer contained 62.7% MSP, 0.77% DSP, and 36.42% probucol, and the aqueous layer contained 12.7% MSP and 85.0% DSP.

The layers were cut. The organic solution was treated with 18.0 g of acetone, 40.4 g of 0.5% brine, and 0.21 mL (0.21 mmol, 12.96 mmol total) of 1 N NaOH. After stirring for 15 min at 50° C., the mixture was allowed to settle and the layers were analyzed. HPLC analysis indicated the organic layer contained 63.41% MSP, 0.21% DSP, and 36.3% probucol, and the aqueous layer contained 30.2% MSP and 68.2% DSP.

The layers were cut. The organic solution was transferred to a 500 mL round bottom flask, heated to 50° C. and acidified by adding 3.2 mL of 4 N HCl (12.9 mmol) and 25.6 mL of water. After stirring for 15 min at 50° C., the aqueous phase was removed (pH of the aqueous layer was 1.25) and the organic layer was washed with 18.0 g acetone and 26.0 g water. Heptanes (100 g) was added to the organic solution and then concentrated at 70° C. under 350 mmHg to ½ volume. The solution was diluted with heptanes to obtain an 8 wt % MSP solution (21.3 mmol). GC analysis indicated that the acetone concentration was less than 1 wt % relative to heptanes.

The mixture was then cooled to ambient temperature and stirred 18 hours. The resulting suspension was filtered to yield 11.5 g MSP as a white crystalline solid (146-148° C. mp). HPLC analysis indicated the solid contained 96.9% MSP, 0.4% DSP, and 2.7% probucol.

Example 73

Ex-73: A 250 mL 2-neck round bottom flask equipped with an addition funnel, temperature probe and $N_2$ bubbler was charged with 20.0 g (38.7 mmol) probucol and 50 mL of anhydrous THF. To this solution was added 25.8 mL (77.4 mmol, 2.0 eq) of 3.0 M methylmagnesium chloride in THF at such a rate that the temperature was kept between 40-50° C. After the addition was complete, the temperature of the mixture was adjusted to 41° C. and a solution of 3.68 g (36.8 mmol, 0.95 eq) succinic anhydride in 37.2 g anhydrous THF was added over 30 min. The temperature during the addition was maintained between 40-45° C. After the addition was complete the reaction mixture was allowed to stir for 60 min at 45° C. The reaction was quenched by the slow addition of 24.6 g (98.4 mmol) of 4 N HCl and 43.9 g of water at 40-50° C. After the quench, the reaction mixture was cooled to 20° C. and the phases were separated. The organic layer was washed with 40.5 g of 3 wt % brine. The organic layer was washed a second time with 39.7 g of 3 wt % brine. HPLC analysis of the organic layer indicated the presence of 53.9% MSP, 12.3% DSP and 32.9% probucol. The organic layer was diluted with 95 g of heptanes and concentrated at 90° C. until about ½ of the solvent was removed. An additional 100 g of heptanes was charged and the organic solution was concentrated at 90° C. until about ½ of the solvent was removed. Heptanes was added to obtain a 12 wt % MSP solution (20.9 mmol). GC analysis indicated the concentration of THF was 5.8 wt % relative to heptanes.

The heptanes solution was transferred to 500 mL round bottom flask and heated to 50° C. The solution was treated with 35.2 g of acetone, 39.8 g of 0.5% brine, and 2.30 mL (11.5 mmol) of 5 N NaOH. After stirring for 30 min at 50° C., the mixture was allowed to separate and the layers were analyzed. HPLC analysis indicated the organic layer contained 66.7% MSP, 3.35% DSP, and 29.7% probucol, and the aqueous layer contained 15.5% MSP, 78.5% DSP and 0.32% probucol.

The layers were cut. The organic solution was treated with 19.5 g of acetone, 40.0 g of 0.5% brine, and 1.00 mL (1.00 mmol, 12.5 mmol total) of 1 N NaOH. After stirring for 30 min at 50° C., the mixture was allowed to separate and the layers were analyzed. HPLC analysis indicated the organic layer contained 66.6% MSP, 0.86% DSP, and 32.4% probucol, and the aqueous layer contained 12.7% MSP, 83.7% DSP and 1.6% probucol.

The layers were cut. The organic solution was treated with 19.5 g of acetone, 39.7 g of 0.5% brine, and 1.21 mL (1.21 mmol, 13.71 mmol total) of 1 N NaOH. After stirring for 30 min at 50° C., the mixture was allowed to separate and the layers were analyzed. HPLC analysis indicated the organic layer contained 62.8% MSP, 0.03% DSP, and 37.0% probucol, and the aqueous layer contained 41.1% MSP, 56.3% DSP and 1.4% probucol.

The layers were cut and the organic solution was concentrated under reduced pressure at 90° C. The residue was dissolved in 30.0 g of THF and 48.4 g of 10 wt % brine was added. To this solution, 6.3 mL (31.4 mmol, 1.5 equiv) of 5 N NaOH was charged and the resulting mixture was stirred at 25° C. for 30 min. The reaction mixture was treated with 4 g of sodium chloride and stirred for 15 min at 25° C.

The layers were cut and the organic solution was concentrated under reduced pressure at 90° C. The residue was slurried in 12 wt % solution of heptanes and aged for 18 hours. The precipitate was collected by filtration and HPLC analysis of the MSP salt indicated the presence of 98.8% MSP, 0.19% DSP, and 0.94% probucol.

Example 74

Ex-74A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.00 eq) of 2.0 M benzylmagnesium chloride in THF at such a rate that the temperature range was 41-51° C. After the addition was complete, the temperature of the mixture was adjusted to 41° C. and a solution of 17.1 g (171 mmol, 1.1 eq) succinic anhydride in 173 g THF was added over approximately 30 min. The temperature over the addition was maintained at 40-45° C. After the addition was complete the reaction mixture was allowed to stir for 45 min at approx. 41° C. HPLC analysis indicated the presence of 12.9% DSP, 59.5% MSP and 25.5% probucol The reaction was quenched by the slow addition of 99.2 g (377 mmol) of 4 N HCl and 150.1 g of water at 40-50° C. After the quench, the reaction mixture was cooled to 20° C. and the phases were separated. The organic layer was washed with 152.1 g of 3% brine. The organic layer was washed a second time with 146.1 g of 3% brine and the organic layer was treated with 41.2 mL (206 mmol. 1.5 equiv) of 5 N NaOH and 200 mL of 10% brine. The reaction mixture was stirred at 20° C. for 30 min and the layers were separated (aqueous layer pH was 12.5). The organic layer was concentrated to 222.5 g by distillation at 90° C. at atmospheric pressure. After charging 255.5 g of heptanes, the organic layer was concentrated to 216.2 g by distillation at 90° C. at atmospheric pressure. An additional 245.5 g of heptanes was added at 90° C. and the slurry was cooled to 20° C. with stirring. After 1 hour, the slurry was filtered and washed with 78 g of heptanes. The wetcake was washed a second time with 65.8 g of heptanes. A total of 143 g of MSP/DSP sodium salt wetcake was collected; HPLC analysis indicated 17.9% DSP, 81.5% MSP and 0.51% probucol.

Ex-74B: A 100 mL round bottom flask was charged with 10.0 g of MSP/DSP sodium salt wetcake (containing water and heptanes) obtained from Ex-74A, 33.4 g of heptanes, 9.2 g of acetone and 10.4 g of acetone. The resulting mixture was treated with 1.3 mL (5.2 mmol) of 4 N HCl, stirred at 50° C. for 30 min. The mixture was allowed to settle and the layers were analyzed. HPLC analysis of the organic layer indicated 97.8% MSP, 1.47% DSP and 0.72% probucol and the aqueous layer contained 59.7% MSP and 40.2% DSP.

Example 75

Ex-75: A 100 mL round bottom flask was charged with 10.0 g of MSP/DSP sodium salt wetcake (containing water and heptanes) obtained from Ex-74A and 15.0 mL of THF. This solution was treated with 6.3 g of water, 2.6 mL of 4 N HCl (10.4 mmol) and stirred at ambient temperature for 1 hour. The layers were cut and the organic solution was washed twice with 8.0 g of 10% brine. HPLC analysis of the organic layer indicated 81.6% MSP, 18.0% DSP and 0.4% probucol.

The organic solution was diluted with 38.2 g of heptanes and ⅔ of the solvent was distilled under reduced pressure at 90° C. The mixture was diluted to the original volume with fresh heptanes and the distillation was repeated two additional times. Heptanes was added to obtain a 9 wt % MSP solution (6.49 mmol). GC analysis indicated that the THF concentration was about 5.9 wt % relative to heptanes. The organic solution was distilled under reduced pressure at 90° C. until ¼ of the solvent was removed. Heptanes was added to obtain a 9 wt % MSP solution (6.49 mmol) and GC analysis indicated that the THF concentration was about 1.1 wt % relative to heptanes.

The heptanes solution was transferred to a 200 mL round bottom flask and heated to 50° C. The solution was treated with 9.2 g of acetone, 12.4 g of 0.5% brine, and 0.58 mL (2.92 mmol) of 5 N NaOH. After stirring for 15 min, the mixture was allowed to settle and the layers were analyzed. HPLC analysis indicated the organic layer contained 96.5% MSP, 2.8% DSP, and 0.5% probucol, and the aqueous layer contained 20.6% MSP and 79.1% DSP. The reaction mixture was treated with an additional 0.65 mL (0.56 mmol, 3.48 mmol total) of 1 N NaOH. After stirring for 15 min at 50° C., the mixture was allowed to settle and the layers were analyzed. HPLC analysis indicated the organic layer contained 98.1% MSP, 1.2% DSP, and 0.5% probucol, and the aqueous layer contained 38.3% MSP and 61.3% DSP.

The layers were cut. The organic solution was treated with 5.0 g of acetone, 12.5 g of 0.5% brine, and 0.32 mL (0.32 mmol, 3.80 mmol total) of 1 N NaOH. After stirring for 15 min at 50° C., the mixture was allowed to settle and the layers were analyzed. HPLC analysis indicated the organic layer contained 99.2% MSP, 0.12% DSP, and 0.57% probucol, and the aqueous layer contained 69.6% MSP and 29.9% DSP.

The layers were cut. The organic solution was treated with 5.0 g of acetone and 12.5 g of 0.5% brine. After stirring for 15 min at 50° C., the mixture was allowed to settle and the layers were analyzed. HPLC analysis indicated the organic layer contained 99.3% MSP and 0.59% probucol, and the aqueous layer contained 78.5% MSP and 20.1% DSP.

Example 76

Ex-76A: A 1 L round bottom flask was charged with 70 g of MSP/DSP sodium salt wetcake (containing water and heptanes) obtained from Ex-74A and 110 mL of THF. The solution was treated with 43.3 g of water, 37 mL (148 mmol) of 4N HCl, 60 g of 10% brine, and the mixture was stirred at 25° C. for 1 hour.

The layers were cut and the organic solution was washed twice with 60 g of 10% brine. HPLC analysis of the organic layer (157 g) indicated the presence of 81.4% MSP, 18.0% DSP and 0.37% probucol.

Ex-76B: 31.5 g of the organic solution obtained from Ex-76A was concentrated under reduced pressure at 80° C. The clear yellow oil was taken up in 50 g of acetone, concentrated under reduced pressure at 80° C. and repeated. GC analysis indicated no residual THF present. The residue was diluted with heptanes to yield a 12 wt % MSP solution (11.7 mmol). The heptanes solution was treated with 16.8 g of acetone, 22.4 g of 0.5% brine and heated to 50° C. The reaction mixture was treated with 0.59 mL (2.90 mmol) of 5 N NaOH. After stirring 15 min at 50° C., the mixture was allowed to settle and the layers were analyzed. HPLC analysis indicated the organic layer contained 93.3% MSP, 6.12% DSP, and 0.40% probucol, and the aqueous layer contained 9.4% MSP and 90.5% DSP.

An additional 0.23 mL (1.17 mmol, 4.07 mmol total) of 5 N NaOH was added to the reaction mixture. After stirring 15 min at 50° C., the mixture was allowed to settle and the layers were analyzed. HPLC analysis indicated the organic layer contained 95.6% MSP, 3.83% DSP, and 0.44% probucol, and the aqueous layer contained 13.5% MSP and 86.3% DSP.

An additional 0.23 mL (1.17 mmol, 5.24 mmol total) of 5 N NaOH was added to the reaction mixture. After stirring 15 min at 50° C., the mixture was allowed to settle and the layers were analyzed. HPLC analysis indicated the organic layer contained 98.1% MSP, 1.24% DSP, and 0.51% probucol, and the aqueous layer contained 36.5% MSP and 63.2% DSP.

An additional 0.23 mL (1.17 mmol, 6.41 mmol total) of 5 N NaOH was added to the reaction mixture. After stirring 15 min at 50° C., the mixture was allowed to settle and the layers were analyzed. HPLC analysis indicated the organic layer contained 98.6% MSP, 0.66% DSP, and 0.60% probucol, and the aqueous layer contained 55.9% MSP and 43.7% DSP.

Example 77

Ex-77: 31.0 g of the organic solution obtained from Ex-76A was concentrated under reduced pressure at 80° C. The clear yellow oil was taken up in 50 g of acetone, concentrated under reduced pressure at 80° C. and repeated. GC analysis indicated no residual THF present. The residue was diluted with heptanes to yield an 11 wt % MSP solution (11.5 mmol). The heptanes solution was treated with 16.2 g of acetone, 22.5 g of 3% brine and heated to 50° C. The reaction mixture was treated with 0.70 mL (3.5 mmol) of 5 N NaOH. After stirring 15 min at 50° C., the mixture was allowed to settle and the layers were analyzed. HPLC analysis indicated the organic layer contained 94.0% MSP, 5.34% DSP, and 0.44% probucol, and the aqueous layer contained 26.8% MSP and 72.9% DSP.

The layers were cut and the organic solution was treated with 20.9 g of 3% brine, 10.1 g of acetone and 0.35 mL (0.35 mmol, 3.85 mmol total) of 1 N NaOH. After stirring 20 min at 50° C., the mixture was allowed to settle and the layers were analyzed. HPLC analysis indicated the organic layer contained 96.5% MSP, 2.87% DSP, and 0.39% probucol, and the aqueous layer contained 9.8% MSP and 90.2% DSP.

The layers were cut and the organic solution was treated with 22.1 g of 3% brine, 10.0 g of acetone and 0.35 mL (0.35 mmol, 4.2 mmol total) of 1 N NaOH. After stirring 20 min at 50° C., the mixture was allowed to settle and the layers were analyzed. HPLC analysis indicated the organic layer contained 98.2% MSP, 1.18% DSP, and 0.43% probucol, and the aqueous layer contained 11.8% MSP and 87.9% DSP.

The layers were cut and the organic solution was treated with 20.0 g of 3% brine and 10.0 g of acetone. The mixture was stirred for 20 min at 50° C., allowed to settle and the layers were analyzed. HPLC analysis indicated the organic layer contained 98.5% MSP, 0.81% DSP, and 0.46% probucol, and the aqueous layer contained 62.5% MSP and 37.0% DSP.

The reaction mixture was treated with 0.15 mL (0.15 mmol, 4.35 mmol total) of 1 N NaOH, stirred at 50° C. for 15 min, allowed to settle and the layers were analyzed. HPLC analysis indicated the organic layer contained 98.8% MSP, 0.50% DSP, and 0.47% probucol, and the aqueous layer contained 19.9% MSP and 79.4% DSP.

The layers were cut. The organic solution was treated with 23.3 g of water, 2.9 mL (11.5 mmol) of 4 N HCl and stirred for 30 min at 50° C. The layers were cut and the organic layer washed with 22 g of water and concentrated under reduced pressure at 80° C. The residue was diluted with heptanes to yield a 12 wt % MSP solution and stirred at ambient temperature for 18 hours. The slurry was cooled using an ice bath and stirred for an additional 3 hours. The precipitate was collected by vacuum filtration and washed with cold heptanes. HPLC analysis of the precipitate indicated the presence of 99.2% MSP, 0.55% DSP and 0.08% probucol.

Example 78

Ex-78: 28.5 g of the organic solution obtained from Ex-76A was concentrated under reduced pressure at 80° C. The clear yellow oil was taken up in 50 g of acetone, concentrated under reduced pressure at 80° C. and repeated. GC analysis indicated no residual THF present. The residue was diluted with heptanes to yield an 11 wt % MSP solution (10.6 mmol). The heptanes solution was treated with 15.2 g of acetone, 21.2 g of water and heated to 50° C. The mixture was treated with 0.75 mL (3.7 mmol) of 5 N NaOH. After stirring for 15 min at 50° C., the mixture was allowed to settle and the layers were analyzed. HPLC analysis indicated the organic layer contained 94.2% MSP, 5.08% DSP, and 0.43% probucol, and the aqueous layer contained 16.8% MSP and 82.9% DSP.

The layers were cut and the organic solution was treated with 20.6 g of water, 10.1 g of acetone and 1.00 mL (1.00 mmol, 4.8 mmol total) of 1 N NaOH. The mixture was stirred for 20 min at 50° C., allowed to settle and the layers were analyzed. HPLC analysis indicated the organic layer contained 98.9% MSP, 0.41% DSP, and 0.46% probucol, and the aqueous layer contained 24.3% MSP and 75.1% DSP.

The layers were cut and the organic solution was treated with 20.2 g water, 10.0 g of acetone, 16 g of 0.5% brine and 0.50 mL (0.50 mmol, 5.30 mmol total) of 1 N NaOH. The mixture was stirred for 20 min at 50° C., allowed to settle and the layers were cut. The organic solution was heated to 50° C. and then treated with 20.3 g of water, 10.0 g of acetone, 2.0 mL (8.0 mmol) of 4 N HCl. After stirring for 30 min at 50° C., the mixture was allowed to settle and the layers were cut. The organic layer washed with 20.6 g of water and concentrated under reduced pressure at 80° C. The residue was diluted with heptanes to yield a 12 wt % MSP solution (10.6 mmol) and ¼ of the solvent was distilled under reduced pressure at 90° C. The mixture was diluted with fresh heptanes to yield a 12 wt % MSP solution. GC analysis indicated no residual acetone. The mixture was stirred at ambient temperature for 18 hours, cooled using an ice bath and stirred for an additional 3 hours. The precipitate was collected by vacuum filtration and washed with cold heptanes. HPLC analysis of the precipitate indicated the presence of 99.84% MSP and 0.04% DSP.

Example 79

Ex-79A: A 1 L 2-neck round bottom flask equipped with an addition funnel, temperature probe and $N_2$ bubbler was charged with 80.0 g (155 mmol) probucol and 160 mL of anhydrous THF. To this solution was added 157 mL (313 mmol, 2.02 eq) of 2.0 M benzylmagnesium chloride in THF at such a rate that the temperature was kept between 40-51° C. After the addition was complete, the temperature of the mixture was adjusted to 41° C. and a solution of 17.0 g (170 mmol, 1.1 eq) succinic anhydride in 181 g anhydrous THF was added over 30 min. The temperature over the addition was maintained between 40-45° C. After the addition was complete the reaction mixture was allowed to stir for 30 min. Analysis by HPLC indicated 58.1% MSP, 12.2% DSP and 27.1% probucol.

The reaction was quenched by the slow addition of 98.2 g (370 mmol) of 4 N HCl and 148.2 g of water at 40-50° C. After the quench, the reaction mixture was cooled to 20° C. and the phases were separated. The organic layer was washed with 160 g of water. The organic layer was washed a second time with 160 g of water. Analysis by HPLC of the organic phase (395.33 g) indicated 58.0% MSP, 12.2% DSP, and 27.3% probucol.

Ex-79B: 99.14 g of the organic solution obtained from Ex-79A was charged to a 250 mL round bottom flask and then treated with 49.0 g of 6% aqueous sodium bicarbonate solution and 2.45 g of NaCl. After stirring 15 min HPLC analysis indicated the organic layer contained 58.4% MSP, 11.2% DSP, and 27.7% probucol, and the aqueous layer contained 26.0% MSP, 65.4% DSP, and 1.8% probucol. The pH of the aqueous layer was 7.49.

The layers were cut. The organic phase was treated with another 49.0 g of 6% aqueous sodium bicarbonate solution and 2.45 g of NaCl. After stirring 15 min HPLC analysis indicated the organic layer contained 58.5% MSP, 11.1% DSP, and 27.8% probucol, and the aqueous layer contained 15.6% MSP and 81.7% DSP. The pH of the aqueous layer was 7.81. The organic layer was solvent switched to heptanes at 70° C. and then cooled to 0° C. and filtered. HPLC analysis indicated the wetcake contained 80.6% MSP and 16.2% DSP, and the filtrate contained 18.3% MSP, 0.08% DSP, and 81.2% probucol.

Example 80

Ex-80: 1 g of the MSP/DSP wetcake (containing heptanes and water) obtained from Ex-70B, 7 mL of heptanes and 3 mL THF were charged to 20 mL vial and heated to 50° C. The mixture cooled to 25° C. and filtered. HPLC analysis indicated the wetcake contained 16.5% MSP, 83.3% DSP, and 0.2% probucol, and the filtrate contained 97.0% MSP, 1.4% DSP, and 0.79% probucol.

Example 81

Ex-81: 1 g of the MSP/DSP wetcake (containing heptanes and water) obtained from Ex-70B, 8 mL of heptanes and 2 mL THF were charged to 20 mL vial and heated to 50° C. The mixture cooled to 25° C. and filtered. HPLC analysis indicated the wetcake contained 20.6% MSP and 79.4% DSP, and the filtrate contained 97.1% MSP, 1.0% DSP, and 1.1% probucol.

Example 82

Ex-82A: A 250 mL round bottom flask equipped with a stir bar and a $N_2$ bubbler was charged with 10 g of MSP, 100 mg of DSP, 100 mg of probucol, 45 g of hexanes, 45 g of ethyl acetate and 18 g of acetone. HPLC analysis of the resulting solution indicated 97.5% MSP, 1.1% DSP, and 1.4% probucol.

Ex-82B: To 9.15 g of the MSP solution obtained from Ex-82A were added 3.5 mL water, 1.5 mL acetone and 45 uL 1 N NaOH. After stirring for 1 min at ambient temperature the layers were allowed to settle. HPLC analysis indicated the organic layer contained 98.4% MSP, 0.18% DSP, and 1.4% probucol, and the aqueous layer contained 54% MSP and 46% DSP.

Example 83

Ex-83: To 9.15 g of the MSP solution obtained from Ex-82A were added 3.5 mL water, 3 mL acetone and 45 uL 1 N NaOH. After stirring for 1 min at ambient temperature the layers were allowed to settle. HPLC analysis indicated the organic layer contained 98.3% MSP, 0.15% DSP, and 1.5% probucol, and the aqueous layer contained 70% MSP, 29% DSP and 1.0% probucol.

Example 84

Ex-84: To 9.15 g of the MSP solution obtained from Ex-82A were added 3.5 mL water, 4.5 mL acetone and 45 uL 1 N NaOH. After stirring for 1 min at ambient temperature the layers were allowed to settle. HPLC analysis indicated the organic layer contained 98.4% MSP, 0.14% DSP, and 1.4% probucol, and the aqueous layer contained 64% MSP, 35% DSP and 0.8% probucol.

Example 85

Ex-85: To 9.15 g of the MSP solution obtained from Ex-82A were added 3.5 mL water, 6 mL acetone and 45 uL 1 N NaOH. After stirring for 1 min at ambient temperature the layers were allowed to settle. HPLC analysis indicated the organic layer contained 98.4% MSP, 0.19% DSP, and 1.5% probucol, and the aqueous layer contained 70% MSP and 30% DSP.

Example 86

Ex-86: To 9.15 g of the MSP solution obtained from Ex-82A were added 3.5 mL 1% brine, 3 mL acetone and 45 uL 1 N NaOH. After stirring for 1 min at ambient temperature the layers were allowed to settle. HPLC analysis indicated the organic layer contained 97.4% MSP, 0.9% DSP, and 1.7% probucol, and the aqueous layer contained 85% MSP, 14% DSP and 1.3% probucol.

Example 87

Ex-87: To 9.15 g of the MSP solution obtained from Ex-82A were added 3.5 mL 0.5% brine, 3 mL acetone and 45 uL 1 N NaOH. After stirring for 1 min at ambient temperature the layers were allowed to settle. HPLC analysis indicated the organic layer contained 97.8% MSP, 0.73% DSP, and 1.4% probucol, and the aqueous layer contained 66.9% MSP, 31.7% DSP and 1.3% probucol.

Example 88

Ex-88A: A 250 mL round bottom flask equipped with a stir bar and a $N_2$ bubbler was charged with 10 g of MSP, 100 mg of DSP, 100 mg of probucol, 22.5 g of heptanes, 67.5 g of ethyl acetate and 20 g of acetone. HPLC analysis of the resulting solution indicated 97.4% MSP, 1.14% DSP, and 1.5% probucol.

Ex-88B: To 12.0 g of the MSP solution obtained from Ex-88A were added 4.0 mL water and 50 uL 1 N NaOH. After stirring for 1 min at ambient temperature the layers were allowed to settle. HPLC analysis indicated the organic layer contained 98.3% MSP, 0.18% DSP, and 1.6% probucol, and the aqueous layer contained 60.2% MSP, 39% DSP and 0.9% probucol.

Example 89

Ex-89: To 12.0 g of the MSP solution obtained from Ex-88A were added 4.0 mL 0.5% brine and 50 uL 1 N NaOH. After stirring for 1 min at ambient temperature the layers were allowed to settle. HPLC analysis indicated the organic layer contained 97.6% MSP, 0.85% DSP, and 1.5% probucol, and the aqueous layer contained 86% MSP, 12% DSP and 1.5% probucol.

Example 90

Ex-90: To 12.0 g of the MSP solution obtained from Ex-88A were added 4.0 mL 0.13% brine and 50 uL 1 N NaOH. After stirring for 1 min at ambient temperature the layers were allowed to settle. HPLC analysis indicated the organic layer contained 97.9% MSP, 0.5% DSP, and 1.6% probucol, and the aqueous layer contained 74.2% MSP, 24.6% DSP and 1.3% probucol.

Example 91

Ex-91A: A 250 mL round bottom flask equipped with a stir bar and a $N_2$ bubbler was charged with 10 g of MSP, 100 mg of DSP, 100 mg of probucol, 45 g of heptanes, 45 g of ethyl acetate and 20 g of acetone. HPLC analysis of the resulting solution indicated 97.6% MSP, 1.12% DSP, and 1.3% probucol.

Ex-91B: To 12.0 g of the MSP solution obtained from Ex-91A were added 4.0 mL water and 50 uL 1 N NaOH. After stirring for 1 min at ambient temperature the layers were allowed to settle. HPLC analysis indicated the organic layer contained 98.3% MSP, 0.18% DSP, and 1.6% probucol, and the aqueous layer contained 85% MSP, 13.5% DSP and 1.34% probucol.

Example 92

Ex-92: To 12.0 g of the MSP solution obtained from Ex-91A were added 4.0 mL 0.5% brine and 50 uL 1 N NaOH. After stirring for 1 min at ambient temperature the layers were allowed to settle. HPLC analysis indicated the organic layer contained 97.7% MSP, 0.69% DSP, and 1.5% probucol, and the aqueous layer contained 90.1% MSP, 7.7% DSP and 1.5% probucol.

Example 93

Ex-93: To 12.0 g of the MSP solution obtained from Ex-91A were added 4.0 mL 0.13% brine and 50 uL 1 N NaOH. After stirring for 1 min at ambient temperature the layers were allowed to settle. HPLC analysis indicated the organic layer contained 98.1% MSP, 0.37% DSP, and 1.6% probucol, and the aqueous layer contained 75.2% MSP, 23.7% DSP and 1.1% probucol.

Example 94

Ex-94A: A 250 mL round bottom flask equipped with a stir bar and a $N_2$ bubbler was charged with 10 g of MSP, 100 mg of DSP, 100 mg of probucol, 67.5 g of heptanes, 22.5 g of ethyl acetate and 20 g of acetone. HPLC analysis of the resulting solution indicated 97.6% MSP, 0.96% DSP, and 1.5% probucol.

Ex-94B: To 12.0 g of the MSP solution obtained from Ex-94A were added 4.0 mL water and 50 uL 1 N NaOH. After stirring for 1 min at ambient temperature the layers were allowed to settle. HPLC analysis indicated the organic layer contained 98.3% MSP, 0.13% DSP, and 1.6% probucol, and the aqueous layer contained 68% MSP, 31% DSP and 1.4% probucol.

Example 95

Ex-95: To 12.0 g of the MSP solution obtained from Ex-94A were added 4.0 mL 0.5% brine and 50 uL 1 N NaOH. After stirring for 1 min at ambient temperature the layers were allowed to settle. HPLC analysis indicated the organic layer contained 97.8% MSP, 0.64% DSP, and 1.6% probucol, and the aqueous layer contained 89.7% MSP, 8.9% DSP and 1.4% probucol.

Example 96

Ex-96: To 12.0 g of the MSP solution obtained from Ex-94A were added 4.0 mL 0.13% brine and 50 uL 1 N NaOH. After stirring for 1 min at ambient temperature the layers were allowed to settle. HPLC analysis indicated the organic layer contained 98.2% MSP, 0.32% DSP, and 1.5% probucol, and the aqueous layer contained 86% MSP, 13% DSP and 1.3% probucol.

Example 97

Ex-97A: To 12.0 g of the MSP solution obtained from Ex-94A were added 4.0 mL 0.5% brine, 2 mL acetone and 50 uL 1 N NaOH. After stirring for 1 min at ambient temperature the layers were allowed to settle. HPLC analysis indicated the organic layer contained 97.9% MSP, 0.55% DSP, and 1.5% probucol, and the aqueous layer contained 68% MSP, 31% DSP and 1.4% probucol.

Ex-97B: Without cutting the layers the biphasic mixture obtained from Ex-97A was heated to 50° C. for 5 min and then held at 50° C. for the layers to separate. HPLC analysis indicated the organic layer contained 97.9% MSP, 0.57% DSP, and 1.5% probucol.

Example 98

Ex-98A: To 12.0 g of the MSP solution obtained from Ex-94A were added 4.0 mL 0.5% brine and 50 uL 1 N LiOH. After stirring for 1 min at ambient temperature the layers were allowed to settle. HPLC analysis indicated the organic layer contained 97.9% MSP, 0.52% DSP, and 1.6% probucol, and the aqueous layer contained 92% MSP, 6.5% DSP and 1.4% probucol.

Ex-98B: Without cutting the layers the biphasic mixture obtained from Ex-98A was heated to 50° C. for 5 min and then held at 50° C. for the layers to separate. HPLC analysis indicated the organic layer contained 97.9% MSP, 0.57% DSP, and 1.6% probucol.

Example 99

Ex-99A: To 12.0 g of the MSP solution obtained from Ex-94A were added 4.0 mL 0.5% brine and 50 uL 1 N KOH. After stirring for 1 min at ambient temperature the layers were allowed to settle. HPLC analysis indicated the organic layer contained 97.9% MSP, 0.5% DSP, and 1.5% probucol, and the aqueous layer contained 85.6% MSP, 13% DSP and 1.3% probucol.

Ex-99B: Without cutting the layers the biphasic mixture obtained from Ex-99A was heated to 50° C. for 5 min and then held at 50° C. for the layers to separate. HPLC analysis indicated the organic layer contained 97.9% MSP, 0.51% DSP, and 1.6% probucol.

Example 100

Ex-100A: A 250 mL round bottom flask equipped with a stir bar and a $N_2$ bubbler was charged with 10 g of MSP, 100 mg of DSP, 100 mg of probucol, 90 g of heptanes and 36 g of acetone. HPLC analysis of the resulting solution indicated 97.5% MSP, 0.9% DSP, and 1.7% probucol.

Ex-100B: To 12.0 g of the MSP solution obtained from Ex-100A were added 4.0 mL 0.5% brine and 50 uL 1 N NaOH. After stirring for 1 min at ambient temperature the layers were allowed to settle. HPLC analysis indicated the organic layer contained 98.4% MSP, 0.3% DSP, and 1.3% probucol, and the aqueous layer contained 92.1% MSP, 6.5% DSP and 1.5% probucol.

Ex-100C: Without cutting the layers the biphasic mixture obtained from Ex-100B was heated to 50° C. for 5 min and then held at 50° C. for the layers to separate. HPLC analysis indicated the organic layer contained 98.3% MSP, 0.17% DSP, and 1.5% probucol, and the aqueous layer contained 31% MSP and 69% DSP.

Example 101

Ex-101A: To 12.0 g of the MSP solution obtained from Ex-100A were added 4.0 mL 0.5% brine and 50 uL 1 N LiOH. After stirring for 1 min at ambient temperature the layers were allowed to settle. HPLC analysis indicated the organic layer contained 98.3% MSP, 0.3% DSP, and 1.4% probucol, and the aqueous layer contained 86.9% MSP, 11.7% DSP and 1.4% probucol.

Ex-101B: Without cutting the layers the biphasic mixture obtained from Ex-101A was heated to 50° C. for 5 min and then held at 50° C. for the layers to separate. HPLC analysis indicated the organic layer contained 98.3% MSP, 0.19% DSP, and 1.5% probucol, and the aqueous layer contained 66.7% MSP, 32.3% DSP, and 0.96% probucol.

Example 102

Ex-102A: To 12.0 g of the MSP solution obtained from Ex-100A were added 4.0 mL 0.5% brine and 50 uL 1 N KOH. After stirring for 1 min at ambient temperature the layers were allowed to settle. HPLC analysis indicated the organic layer contained 98.2% MSP, 0.3% DSP, and 1.5% probucol, and the aqueous layer contained 86% MSP, 13% DSP and 1.3% probucol.

Ex-102B: Without cutting the layers the biphasic mixture obtained from Ex-102A was heated to 50° C. for 5 min and then held at 50° C. for the layers to separate. HPLC analysis indicated the organic layer contained 98.3% MSP, 0.15% DSP, and 1.5% probucol, and the aqueous layer contained 57.7% MSP and 42.3% DSP.

Example 103

Ex-103A: To 12.0 g of the MSP solution obtained from Ex-100A were added 4.0 mL 0.13% brine and 50 uL 1 N NaOH. After stirring for 1 min at ambient temperature the layers were allowed to settle. HPLC analysis indicated the organic layer contained 98.5% MSP, 0.12% DSP, and 1.4% probucol, and the aqueous layer contained 77.9% MSP, 21% DSP and 1.0% probucol.

Ex-103B: Without cutting the layers the biphasic mixture obtained from Ex-103A was heated to 50° C. for 5 min and then held at 50° C. for the layers to separate. HPLC analysis indicated the organic layer contained 98.4% MSP, 0.07% DSP, and 1.5% probucol, and the aqueous layer contained 53.5% MSP and 46.5% DSP.

Example 104

Ex-104A: A 250 mL round bottom flask equipped with a stir bar and a $N_2$ bubbler was charged with 10 g of MSP, 100 mg of DSP, 100 mg of probucol, 90 g of heptanes and 20 g of ethyl alcohol. HPLC analysis of the resulting solution indicated 97.3% MSP, 1.1% DSP, and 1.6% probucol.

Ex-104B: To 12.0 g of the MSP solution obtained from Ex-104A were added 4.0 mL 0.5% brine and 50 uL 1 N NaOH. After stirring for 1 min at ambient temperature the layers were allowed to settle. HPLC analysis indicated the organic layer contained 97.8% MSP, 0.61% DSP, and 1.6% probucol, and the aqueous layer contained 92.4% MSP, 6% DSP and 1.4% probucol.

Example 105

Ex-105: To 12.0 g of the MSP solution obtained from Ex-104A were added 4.0 mL 0.13% brine and 50 uL 1 N NaOH. After stirring for 1 min at ambient temperature the layers were allowed to settle. HPLC analysis indicated the organic layer contained 98.1% MSP, 0.37% DSP, and 1.6% probucol, and the aqueous layer contained 50% MSP and 50% DSP.

Example 106

Ex-106: To 12.0 g of the MSP solution obtained from Ex-104A were added 4.0 mL water and 50 uL 1 N NaOH. After stirring for 1 min at ambient temperature the layers were allowed to settle. HPLC analysis indicated the organic layer contained 98.1% MSP, 0.3% DSP, and 1.6% probucol, and the aqueous layer contained 73% MSP and 27% DSP.

Example 107

Ex-107: To 12.0 g of the MSP solution obtained from Ex-104A were added 4.0 mL 0.5% brine, 2 mL ethyl alcohol and 50 uL 1 N NaOH. After stirring for 5 min at 50° C. the layers were allowed to settle. HPLC analysis indicated the organic layer contained 97.5% MSP, 0.87% DSP, and 1.6% probucol, and the aqueous layer contained 90% MSP and 10% DSP.

Example 108

Ex-108: To 12.0 g of the MSP solution obtained from Ex-104A were added 4.0 mL 0.13% brine, 2 mL ethyl alcohol and 50 uL 1 N NaOH. After stirring for 5 min at 50° C. the layers were allowed to settle. HPLC analysis indicated the organic layer contained 97.6% MSP, 0.83% DSP, and 1.6% probucol, and the aqueous layer contained 90.7% MSP and 9.3% DSP.

Example 109

Ex-109: To 12.0 g of the MSP solution obtained from Ex-104A were added 4.0 mL water, 2 mL ethyl alcohol and 50 uL 1 N NaOH. After stirring for 5 min at 50° C. the layers were allowed to settle. HPLC analysis indicated the organic layer contained 97.5% MSP, 0.83% DSP, and 1.6% probucol, and the aqueous layer contained 92.9% MSP and 7.1% DSP.

Example 110

Ex-110: A 200 mL round bottom flask equipped with a stir bar and a $N_2$ bubbler was charged with 5 g of MSP, 50 mg of DSP, 50 mg of probucol, 45 g of heptanes and 10 g of ethyl alcohol. The mixture was then heated to 50° C. HPLC analysis of the resulting solution indicated 97.3% MSP, 1.2% DSP, and 1.5% probucol. Water (20 mL) and 275 uL 1 N NaOH were then added. After stirring for 5 min at 50° C. the layers were allowed to settle. HPLC analysis indicated the organic layer contained 98.3% MSP, 0.13% DSP, and 1.5% probucol, and the aqueous layer contained 46.6% MSP and 53.4% DSP.

Example 111

Ex-111: A 200 mL round bottom flask equipped with a stir bar and a $N_2$ bubbler was charged with 5 g of MSP, 50 mg of DSP, 50 mg of probucol, 45 g of heptanes and 10 g of ethyl alcohol. The mixture was then heated to 50° C. HPLC analysis of the resulting solution indicated 97.4% MSP, 1.2% DSP, and 1.4% probucol. 0.13% Brine (20 mL) and 275 uL 1 N NaOH were then added. After stirring for 5 min at 50° C. the layers were allowed to settle. HPLC analysis indicated the organic layer contained 98.3% MSP, 0.25% DSP, and 1.5% probucol, and the aqueous layer contained 39.2% MSP and 60.8% DSP. After 1 hour at 50° C. the biphasic mixture was heated to 70° C. and held. HPLC analysis indicated the organic layer contained 98.4% MSP, 0.19% DSP, and 1.4% probucol, and the aqueous layer contained 41.7% MSP and 58.3% DSP.

Example 112

Ex-112: A 200 mL round bottom flask equipped with a stir bar and a $N_2$ bubbler was charged with 5 g of MSP, 50 mg of DSP, 50 mg of probucol, 45 g of heptanes, 7.65 g of THF and 20 mL water. After heating to 65° C. the mixture was treated with 275 uL 1 N NaOH and 100 mg NaCl. After stirring for 15 min at 65° C. the layers were allowed to settle. HPLC analysis indicated the organic layer contained 98.1% MSP, 0.43% DSP, and 1.5% probucol, and the aqueous layer contained 59.8% MSP and 40.2% DSP.

Example 113

Ex-113: A 200 mL round bottom flask equipped with a stir bar and a $N_2$ bubbler was charged with 5 g of MSP, 50 mg of DSP, 50 mg of probucol, 45 g of heptanes, 9.5 g of ethyl acetate and 20 mL water. After heating to 70° C. the mixture was treated with 275 uL 1 N NaOH. After stirring for 15 min at 70° C. the layers were allowed to settle. HPLC analysis indicated the organic layer contained 98.3% MSP, 0.21% DSP, and 1.5% probucol, and the aqueous layer contained 5.65% MSP and 94.2% DSP. Without cutting the layers 100 mg NaCl was added to the mixture and aged at 70° C. for 15 min. HPLC analysis indicated the organic layer contained 97.5% MSP, 0.9% DSP, and 1.5% probucol, and the aqueous layer contained 49.6% MSP and 50.4% DSP.

We claim:

1. A process of separating a compound of Formula I and/or a salt of the compound of Formula I,

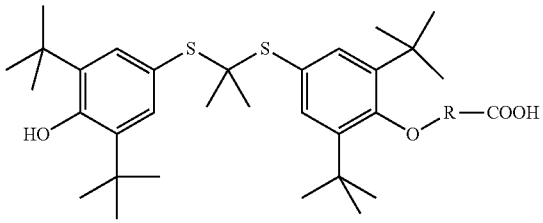

wherein R is an alkyl or —C(O)alkyl-, from a first mixture, the first mixture comprising:
  either
    the compound of Formula I;
    a compound of Formula II,

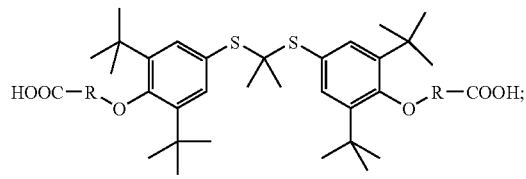

and probucol;
  or
    a salt of the compound of Formula I;
    a salt of the compound of Formula II; and
    probucol;
  the process comprising:
    (a) partially neutralizing the first mixture
    thus affording a partially neutralized second mixture, the partially neutralized second mixture comprising:
      an aqueous phase;
      an organic phase;
      the compound of Formula I;
      a salt of the compound of Formula I;
      the compound of Formula II and/or a salt of the compound of Formula II; and
      probucol;
    (b) removing from the partially neutralized second mixture
      the aqueous phase comprising:
        the compound of Formula II and/or a salt of the compound of Formula II,
      thus leaving the organic phase comprising:
        the compound of Formula I and/or a salt of the compound of Formula I; and
        probucol;
    (c) isolating the compound of Formula I and/or a salt of the compound of Formula I.

2. The process of claim 1, wherein the organic phase comprises at least a first organic solvent and a second organic solvent.

3. The process of claim 2, wherein the first organic solvent is independently a straight chain, branched or cyclic hydrocarbon that is saturated, unsaturated or partially unsaturated, and mixtures thereof.

4. The process of claim 2, wherein the first organic solvent is independently selected from the group consisting of benzene, toluene, xylene, mesitylene, naphthalene, pentane, hexane, heptane, octane, nonane, decane, undecane, dodecane, tridecane, tetradecane, pentadecane, hexadecane, heptadecane, eicosane, cyclohexane, petroleum ether, and mixtures thereof.

5. The process of claim 2, wherein the second organic solvent is independently selected from the group consisting of an ether, an ester, an alcohol, an amide, a nitrile, and a ketone, and mixtures thereof.

6. The process of claim 2, wherein the second organic solvent is independently selected from the group consisting of tetrahydrofuran, ethyl acetate, isopropyl acetate, methyl alcohol, ethyl alcohol, isopropyl alcohol, acetonitrile, dimethylformamide, acetone, 2-butanone, and mixtures thereof.

7. The process of claim 2, wherein the first organic solvent is independently hexane, heptane, or toluene, and said second organic solvent is independently tetrahydrofuran, acetone or 2-butanone.

8. The process of claim 7, wherein R is —C(O)(CH$_2$)$_2$—.

9. The process of claim 2 or 8, wherein the first mixture comprises
the compound of Formula I;
the compound of Formula II; and
probucol; and step (a) comprises adding a base.

10. The process of claim 2 or 8, wherein the first mixture comprises
a salt of the compound of Formula I;
a salt of the compound of Formula II; and
probucol; and step (a) comprises adding an acid.

11. The process of claim 9, wherein the base is sodium hydroxide, potassium hydroxide, or lithium hydroxide.

12. The process of claim 11, wherein the base is sodium hydroxide.

13. The process of claim 1 or 8, wherein the first mixture comprises
the compound of Formula I;
the compound of Formula II; and
probucol; and step (a) comprises adding sodium bicarbonate.

14. The process of claim 1 or 2, wherein steps (a) and then (b) are repeated one time prior to step (c).

15. The process of claim 14, wherein each step (a) comprises independently adding a base.

16. The process of claim 15, wherein each step (a) comprises adding sodium hydroxide.

17. The process of claim 16, wherein the repetition of step (a) further comprises adding a solvent.

18. The process of claim 17, wherein the solvent is independently tetrahydrofuran, acetone or 2-butanone.

19. The process of claim 1 or 2, wherein steps (a) and then (b) are repeated two times prior to step (c).

20. The process of claim 19, wherein each step (a) comprises independently adding a base.

21. The process of claim 20, wherein each step (a) comprises adding sodium hydroxide.

22. The process of claim 21, wherein each repetition of step (a) further comprises adding a solvent.

23. The process of claim 22, wherein the solvent is independently tetrahydrofuran, acetone or 2-butanone.

24. The process of claim 1, wherein R is —C(O)(CH$_2$)$_2$—; the organic phase comprises heptanes; steps (a) and then (b) are repeated two times prior to step (c); each partial neutralization comprises adding sodium hydroxide; and each repetition of step (a) further comprises adding acetone.

25. The process of claim 1, wherein R is —C(O)(CH$_2$)$_2$—; the organic phase comprises heptanes; steps (a) and then (b) are repeated two times prior to step (c); each partial neutralization comprises adding independently sodium hydroxide, potassium hydroxide, or lithium hydroxide; and each repetition of step (a) further comprises adding acetone.

26. A process of separating probucol monosuccinate:

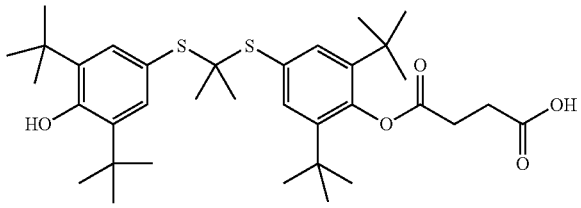

and/or a salt of probucol monosuccinate from a first mixture, wherein the first mixture comprises:
probucol monosuccinate;
probucol disuccinate:

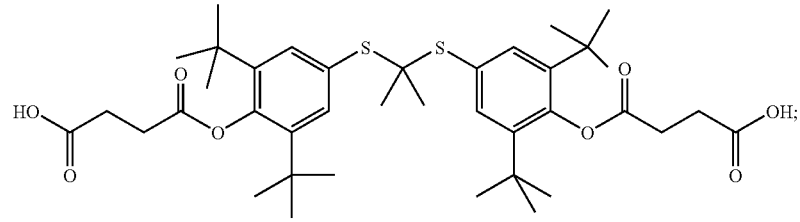

and probucol;
the process comprising:
(a) partially neutralizing the first mixture wherein the partial neutralization comprises adding sodium hydroxide to the first mixture, thus affording a partially neutralized second mixture, the partially neutralized second mixture comprising:
an aqueous phase;
an organic phase comprising heptane and tetrahydrofuran;
probucol monosuccinate;
a salt of probucol monosuccinate;
probucol disuccinate and/or a salt of probucol disuccinate; and
probucol;
(b) removing the aqueous phase from the partially neutralized second mixture, leaving the organic phase;
(c) adding acetone and sodium hydroxide to the organic phase, thus affording a partially neutralized third mixture;

(d) removing an aqueous phase from the partially neutralized third mixture, leaving an organic phase comprising probucol monosuccinate and/or a salt of probucol monosuccinate and probucol;

(e) isolating probucol monosuccinate and/or a salt of probucol monosuccinate.

27. A process of separating a compound of Formula I and/or a salt of the compound of Formula I,

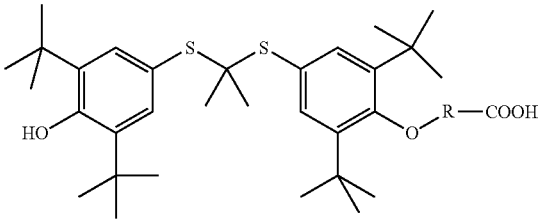

wherein R is a alkyl or —C(O)alkyl-, from a first mixture, the first mixture comprising:
either
the compound of Formula I; and
a compound of Formula II,

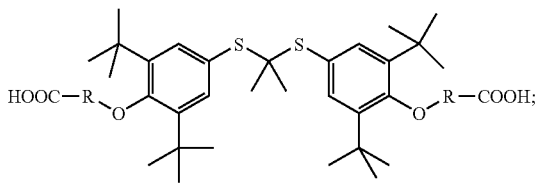

a salt of compound of Formula I; and
a salt of compound of Formula II;
the process comprising:
(a) partially neutralizing the first mixture thus affording a partially neutralized second mixture, the partially neutralized second mixture comprising:
an aqueous phase;
an organic phase;
the compound of Formula I;
a salt of a compound of Formula I; and
the compound of Formula II and/or a salt of a compound of Formula II;
(b) removing from a partially neutralized second mixture the aqueous phase comprising:
the compound of Formula II and/or a salt of the compound of Formula II,
thus leaving the organic phase comprising:
the compound of Formula I and/or a salt of the compound of Formula I;
(c) isolating the compound of Formula I and/or a salt of the compound of Formula I;
wherein steps (a) and then (b) are repeated at least one time prior to step (c).

28. The process of claim 27, wherein the organic phase comprises at least a first organic solvent and a second organic solvent.

29. The process of claim 28, wherein the first organic solvent is independently a straight chain, branched or cyclic hydrocarbon that is saturated, unsaturated or partially unsaturated, and mixtures thereof.

30. The process of claim 28, wherein the first organic solvent is independently selected from the group consisting of benzene, toluene, xylene, mesitylene, naphthalene, pentane, hexane, heptane, octane, nonane, decane, undecane, dodecane, tridecane, tetradecane, pentadecane, hexadecane, heptadecane, eicosane, cyclohexane, petroleum ether, and mixtures thereof.

31. The process of claim 28, wherein the second organic solvent is independently selected from the group consisting of an ether, an ester, an alcohol, an amide, a nitrile, a ketone, and mixtures thereof.

32. The process of claim 28, wherein the second organic solvent is independently selected from the group consisting of tetrahydrofuran, ethyl acetate, isopropyl acetate, methyl alcohol, ethyl alcohol, isopropyl alcohol, acetonitrile, dimethylformamide, acetone, 2-butanone, and mixtures thereof.

33. The process of claim 28, wherein the first organic solvent is independently hexane, heptane, or toluene, and the second organic solvent is tetrahydrofuran, acetone or 2-butanone.

34. The process of claim 33, wherein R is —C(O)(CH$_2$)$_2$—.

35. The process of claim 28 or 34, wherein the first mixture comprises
the compound of Formula I; and
the compound of Formula II;
and step (a) comprises adding a base.

36. The process of claim 28 or 34, wherein the first mixture comprises
a salt of the compound of Formula I; and
a salt of the compound of Formula II;
and step (a) comprises adding an acid.

37. The process of claim 35, wherein the base is sodium hydroxide, potassium hydroxide, or lithium hydroxide.

38. The process of claim 37, wherein the base is sodium hydroxide.

39. The process of claim 27 or 34, wherein the first mixture comprises
the compound of Formula I; and
the compound of Formula II;
and step (a) comprises adding sodium bicarbonate.

40. The process of claim 27 or 28, wherein steps (a) and then (b) are repeated one time prior to step (c).

41. The process of claim 40, wherein each step (a) comprises independently adding a base.

42. The process of claim 41, wherein each step (a) comprises adding sodium hydroxide.

43. The process of claim 42, wherein the repetition of step (a) further comprises adding a solvent.

44. The process of claim 43, wherein the solvent is independently tetrahydrofuran, acetone or 2-butanone.

45. The process of claim 27 or 28, wherein steps (a) and then (b) are repeated two times prior to step (c).

46. The process of claim 45, wherein each step (a) comprises independently adding a base.

47. The process of claim 46, wherein each step (a) comprises adding sodium hydroxide.

48. The process of claim 47, wherein each repetition of step (a) further comprises adding a solvent.

49. The process of claim 48, wherein the solvent is independently tetrahydrofuran, acetone or 2-butanone.

50. The process of claim 27, wherein R is —C(O)(CH$_2$)$_2$—; the organic phase comprises heptanes; steps (a)

and then (b) are repeated two times prior to step (c); each partial neutralization comprises adding sodium hydroxide; and each repetition of step (a) further comprises adding acetone.

51. The process of claim 27, wherein R is —C(O)(CH$_2$)$_2$—; the organic phase comprises heptanes; steps (a) and then (b) are repeated two times prior to step (c); each partial neutralization comprises adding independently sodium hydroxide, potassium hydroxide, or lithium hydroxide; and each repetition of step (a) further comprises adding acetone.

52. A process of separating probucol monosuccinate:

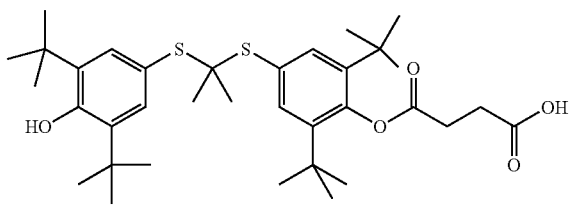

and/or a salt of probucol monosuccinate from a first mixture, wherein the first mixture comprises:
probucol monosuccinate; and
probucol disuccinate:

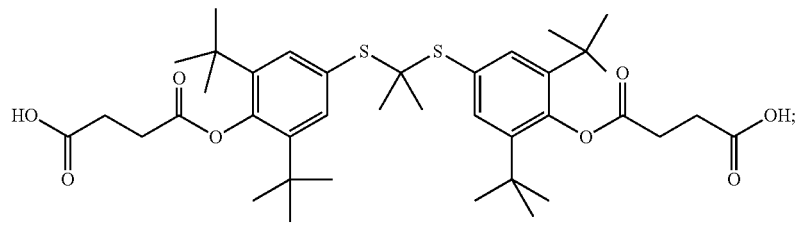

the process comprising:
(a) partially neutralizing the first mixture wherein the partial neutralization comprises adding sodium hydroxide to the first mixture, thus affording a partially neutralized second mixture, the partially neutralized second mixture comprising:
an aqueous phase;
an organic phase comprising heptane and tetrahydrofuran;
probucol monosuccinate;
a salt of probucol monosuccinate; and
probucol disuccinate and/or a salt of probucol disuccinate;
(b) removing the aqueous phase from the partially neutralized second mixture, leaving the organic phase;
(c) adding acetone and sodium hydroxide to the organic phase, thus affording a partially neutralized third mixture;
(d) removing an aqueous phase from the partially neutralized third mixture, leaving an organic phase comprising probucol monosuccinate and/or a salt of probucol monosuccinate;
(e) isolating probucol monosuccinate and/or a salt of probucol monosuccinate.

53. A process of separating a compound of Formula I and/or a salt of the compound of Formula I,

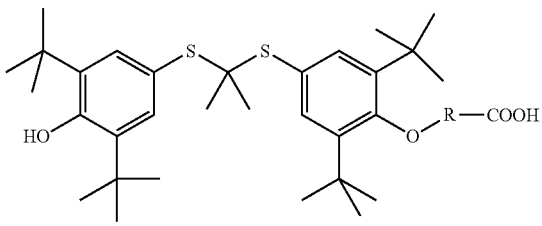

wherein R is an alkyl or —C(O)alkyl-, from a first mixture, the first mixture comprising:
either
the compound of Formula I;
a compound of Formula II,

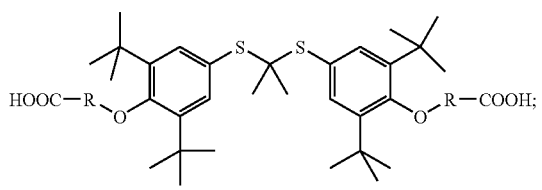

and probucol;
or
a salt of the compound of Formula I;
a salt of the compound of Formula II; and
probucol;
the process comprising:
(a) removing probucol from the first mixture to afford a second mixture
(b) partially neutralizing the second mixture; thus affording a partially neutralized third mixture comprising:
an aqueous phase;
an organic phase;
the compound of Formula I;
a salt of a compound of Formula I; and
the compound of Formula II and/or a salt of the compound of Formula II;
(c) removing from a partially neutralized third mixture the aqueous phase comprising:
the compound of Formula II and/or a salt of the compound of Formula II,
thus leaving the organic phase comprising:
the compound of Formula I and/or a salt of the compound of Formula I;
(d) isolating the compound of Formula I and/or a salt of the compound of Formula I; and
wherein steps (b) and then (c) are repeated at least one time prior to step (d).

54. The process of claim 53, wherein the organic phase comprises at least a first organic solvent and a second organic solvent.

55. The process of claim 54, wherein the first organic solvent is independently a straight chain, branched or cyclic hydrocarbon that is saturated, unsaturated or partially unsaturated, and mixtures thereof.

56. The process of claim 54, wherein the first organic solvent is independently selected from the group consisting of benzene, toluene, xylene, mesitylene, naphthalene, pentane, hexane, heptane, octane, nonane, decane, undecane, dodecane, tridecane, tetradecane, pentadecane, hexadecane, heptadecane, eicosane, cyclohexane, petroleum ether, and mixtures thereof.

57. The process of claim 54, wherein the second organic solvent is independently selected from the group consisting of an ether, an ester, an alcohol, an amide, a nitrile, a ketone, and mixtures thereof.

58. The process of claim 54, wherein the second organic solvent is independently selected from the group consisting of tetrahydrofuran, ethyl acetate, isopropyl acetate, methyl alcohol, ethyl alcohol, isopropyl alcohol, acetonitrile, dimethylformamide, acetone, 2-butanone, and mixtures thereof.

59. The process of claim 54, wherein the first organic solvent is independently hexane, heptane, or toluene, and the second organic solvent is tetrahydrofuran, acetone or 2-butanone.

60. The process of claim 59, wherein R is —C(O)(CH$_2$)$_2$—.

61. The process of claim 54 or 60, wherein the second mixture comprises
the compound of Formula I; and
the compound of Formula II;
and step (b) comprises adding a base.

62. The process of claim 54 or 60, wherein the second mixture comprises
a salt of the compound of Formula I; and
a salt of the compound of Formula II;
and step (b) comprises adding an acid.

63. The process of claim 61, wherein the base is sodium hydroxide, potassium hydroxide, or lithium hydroxide.

64. The process of claim 63, wherein the base is sodium hydroxide.

65. The process of claim 53 or 60, wherein the second mixture comprises
the compound of Formula I; and
the compound of Formula II;
and step (b) comprises adding sodium bicarbonate.

66. The process of claim 53 or 54, wherein steps (b) and then (c) are repeated one time prior to step (d).

67. The process of claim 66, wherein each step (b) comprises independently adding a base.

68. The process of claim 67, wherein each step (b) comprises adding sodium hydroxide.

69. The process of claim 68, wherein the repetition of step (b) further comprises adding a solvent.

70. The process of claim 69, wherein the solvent is independently tetrahydrofuran, acetone or 2-butanone.

71. The process of claim 53 or 54, wherein steps (b) and then (c) are repeated two times prior to step (d).

72. The process of claim 71, wherein each step (b) comprises independently adding a base.

73. The process of claim 72, wherein each step (b) comprises adding sodium hydroxide.

74. The process of claim 73, wherein each repetition of step (b) further comprises adding a solvent.

75. The process of claim 74, wherein the solvent is independently tetrahydrofuran, acetone or 2-butanone.

76. The process of claim 53, wherein R is —C(O)(CH$_2$)$_2$—; the organic phase comprises heptanes; steps (b) and then (c) are repeated two times prior to step (d); each partial neutralization comprises adding sodium hydroxide; and each repetition of step (b) further comprises adding acetone.

77. The process of claim 53, wherein R is —C(O)(CH$_2$)$_2$—; the organic phase comprises heptanes; steps (b) and then (c) are repeated two times prior to step (d); each partial neutralization comprises adding independently sodium hydroxide, potassium hydroxide, or lithium hydroxide; and each repetition of step (b) further comprises adding acetone.

78. A process of separating probucol monosuccinate:

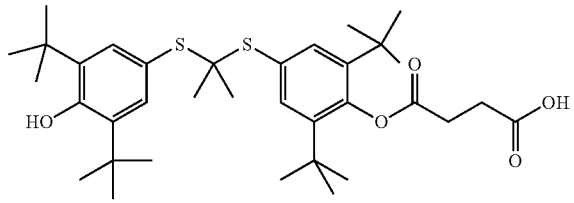

and/or a salt of probucol monosuccinate from a first mixture, wherein the first mixture comprises:
probucol monosuccinate; and
probucol disuccinate:
probucol;

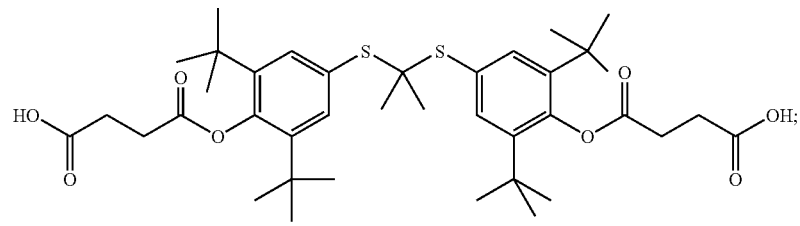

the process comprising:
(a) removing probucol from the first mixture to afford a second mixture
(b) partially neutralizing the second mixture thus affording a partially neutralized third mixture comprising:
 an aqueous phase;
 an organic phase comprising heptanes;
 probucol monosuccinate;
 a salt of probucol monosuccinate; and
 probucol disuccinate and/or a salt of probucol disuccinate;
(c) removing the aqueous phase from the partially neutralized third mixture, leaving the organic phase;
(d) adding acetone and sodium hydroxide to the organic phase, thus affording a partially neutralized fourth mixture;
(e) removing an aqueous phase from the partially neutralized fourth mixture, leaving an organic phase comprising probucol monosuccinate and/or a salt of probucol monosuccinate;
(f) isolating probucol monosuccinate and/or a salt of probucol monosuccinate.

* * * * *

UNITED STATES PATENT AND TRADEMARK OFFICE
CERTIFICATE OF CORRECTION

PATENT NO. : 7,687,659 B2  Page 1 of 1
APPLICATION NO. : 11/409539
DATED : March 30, 2010
INVENTOR(S) : M. David Weingarten et al.

It is certified that error appears in the above-identified patent and that said Letters Patent is hereby corrected as shown below:

On the Title Page, Item (60), should read

Related U.S. Application Data

Provisional application No. 60/674,001, filed <u>April 21, 2005</u>, and Provisional application No. 60/705,837, filed Aug. 5, 2005

Signed and Sealed this

Twenty-first Day of September, 2010

David J. Kappos
*Director of the United States Patent and Trademark Office*